United States Patent
Morris et al.

(10) Patent No.: US 8,532,793 B2
(45) Date of Patent: Sep. 10, 2013

(54) TECHNIQUES FOR PLACING MEDICAL LEADS FOR ELECTRICAL STIMULATION OF NERVE TISSUE

(75) Inventors: Mary M. Morris, Shoreview, MN (US); Avram Scheiner, Vadnais Heights, MN (US); Ruth N. Klepfer, St. Louis Park, MN (US); John E. Burnes, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 253 days.

(21) Appl. No.: 12/433,809

(22) Filed: Apr. 30, 2009

(65) Prior Publication Data

US 2009/0276023 A1 Nov. 5, 2009

Related U.S. Application Data

(60) Provisional application No. 61/007,542, filed on Apr. 30, 2008, provisional application No. 61/007,543, filed on Apr. 30, 2008, provisional application No. 61/190,045, filed on Apr. 30, 2008, provisional application No. 61/190,046, filed on Apr. 30, 2008.

(51) Int. Cl.
*A61N 1/00* (2006.01)

(52) U.S. Cl.
USPC .......................................... 607/130

(58) Field of Classification Search
USPC .......................................... 607/130
See application file for complete search history.

(56) References Cited

U.S. PATENT DOCUMENTS

| | | | |
|---|---|---|---|
| 3,421,511 A | | 1/1969 | Schwartz et al. |
| 3,522,811 A | | 8/1970 | Seymour et al. |
| 3,593,718 A | | 7/1971 | Krasner et al. |
| 3,645,267 A | | 2/1972 | Hagfors |
| 3,650,277 A | | 3/1972 | Sjostrand et al. |
| 3,796,221 A | | 3/1974 | Hagfors |
| 3,878,564 A | | 4/1975 | Yao et al. |
| 4,044,774 A | | 8/1977 | Corbin et al. |
| 4,136,702 A | * | 1/1979 | Trabucco ..................... 607/130 |
| 4,146,029 A | | 3/1979 | Ellinwood, Jr. |
| 4,340,063 A | | 7/1982 | Maurer |
| 4,428,378 A | | 1/1984 | Anderson et al. |
| 4,458,696 A | | 7/1984 | Larimore |
| 4,485,813 A | | 12/1984 | Anderson et al. |
| 4,535,774 A | | 8/1985 | Olson |
| 4,549,556 A | | 10/1985 | Tarjan et al. |
| 4,686,988 A | | 8/1987 | Sholder |

(Continued)

FOREIGN PATENT DOCUMENTS

| DE | 19912635 A1 | 9/2000 |
|---|---|---|
| DE | 19912635 A1 | 9/2000 |

(Continued)

OTHER PUBLICATIONS

Reply to Written Opinion from related PCT Application Serial No. PCT/US2009/042434 filed Feb. 26, 2010 (12 pgs.).

(Continued)

*Primary Examiner* — Christopher D Koharski
*Assistant Examiner* — Nadia Ahmad
(74) *Attorney, Agent, or Firm* — Carol F. Barry

(57) ABSTRACT

This disclosure is directed to extra, intra, and transvascular medical lead placement techniques for arranging medical leads and electrical stimulation and/or sensing electrodes proximate nerve tissue within a patient.

9 Claims, 26 Drawing Sheets

(56) References Cited

U.S. PATENT DOCUMENTS

| | | | |
|---|---|---|---|
| 4,694,835 A | 9/1987 | Strand | |
| 4,750,495 A | 6/1988 | Moore et al. | |
| 4,880,005 A | 11/1989 | Pless et al. | |
| 4,903,701 A | 2/1990 | Moore et al. | |
| 4,998,974 A | 3/1991 | Aker | |
| 5,031,618 A | 7/1991 | Mullett | |
| 5,058,584 A | 10/1991 | Bourgeois | |
| 5,135,004 A | 8/1992 | Adams et al. | |
| 5,149,713 A | 9/1992 | Bousquet | |
| 5,170,802 A | 12/1992 | Mehra | |
| 5,199,428 A | 4/1993 | Obel et al. | |
| 5,203,326 A | 4/1993 | Collins | |
| 5,213,098 A | 5/1993 | Bennett et al. | |
| 5,220,917 A | 6/1993 | Cammilli et al. | |
| 5,224,491 A | 7/1993 | Mehra | |
| 5,243,980 A | 9/1993 | Mehra | |
| 5,251,621 A | 10/1993 | Collins | |
| 5,255,691 A | 10/1993 | Otten | |
| 5,292,336 A | 3/1994 | Spence, Jr. et al. | |
| 5,292,338 A | 3/1994 | Bardy | |
| 5,330,505 A | 7/1994 | Cohen | |
| 5,330,507 A | 7/1994 | Schwartz | |
| 5,330,515 A | 7/1994 | Rutecki et al. | |
| 5,331,966 A | 7/1994 | Bennett et al. | |
| 5,334,221 A | 8/1994 | Bardy | |
| 5,342,409 A | 8/1994 | Mullett | |
| 5,360,441 A | 11/1994 | Otten | |
| 5,464,434 A | 11/1995 | Alt | |
| 5,496,363 A | 3/1996 | Burgio et al. | |
| 5,554,163 A * | 9/1996 | Shturman | 606/159 |
| 5,564,434 A | 10/1996 | Halperin et al. | |
| 5,584,874 A | 12/1996 | Rugland et al. | |
| 5,607,418 A | 3/1997 | Arzbaecher | |
| 5,617,854 A | 4/1997 | Munsif | |
| 5,651,378 A | 7/1997 | Matheny et al. | |
| 5,690,681 A | 11/1997 | Geddes et al. | |
| 5,700,282 A | 12/1997 | Zabara | |
| 5,702,429 A | 12/1997 | King | |
| 5,733,296 A * | 3/1998 | Rogers et al. | 606/159 |
| 5,776,170 A | 7/1998 | MacDonald et al. | |
| 5,792,187 A | 8/1998 | Adams | |
| 5,817,131 A | 10/1998 | Elsberry et al. | |
| 5,824,021 A | 10/1998 | Rise | |
| 5,824,030 A | 10/1998 | Yang et al. | |
| 5,830,222 A | 11/1998 | Makower | |
| 5,913,876 A | 6/1999 | Taylor et al. | |
| 6,006,134 A | 12/1999 | Hill et al. | |
| 6,058,331 A | 5/2000 | King | |
| 6,073,048 A | 6/2000 | Kieval et al. | |
| 6,077,217 A * | 6/2000 | Love et al. | 600/36 |
| 6,134,470 A | 10/2000 | Hartlaub | |
| 6,141,586 A | 10/2000 | Mower | |
| 6,161,029 A | 12/2000 | Spreigl et al. | |
| 6,178,349 B1 | 1/2001 | Kieval | |
| 6,272,377 B1 | 8/2001 | Sweeney et al. | |
| 6,292,695 B1 * | 9/2001 | Webster et al. | 607/14 |
| 6,473,644 B1 | 10/2002 | Terry, Jr. et al. | |
| 6,505,075 B1 | 1/2003 | Weiner | |
| 6,587,726 B2 | 7/2003 | Lurie et al. | |
| 6,709,444 B1 | 3/2004 | Makower | |
| 6,748,255 B2 * | 6/2004 | Fuimaono et al. | 600/374 |
| 6,885,888 B2 | 4/2005 | Rezai | |
| 6,934,583 B2 | 8/2005 | Weinberg et al. | |
| 6,971,393 B1 | 12/2005 | Mamo et al. | |
| 7,010,345 B2 | 3/2006 | Hill et al. | |
| 7,072,720 B2 | 7/2006 | Puskas | |
| 7,191,015 B2 | 3/2007 | Lamson et al. | |
| 7,212,867 B2 | 5/2007 | Van Venrooij et al. | |
| 7,218,964 B2 | 5/2007 | Hill et al. | |
| 7,324,852 B2 | 1/2008 | Barolat et al. | |
| 2002/0107553 A1 | 8/2002 | Hill et al. | |
| 2002/0198572 A1 | 12/2002 | Weiner | |
| 2004/0015193 A1 | 1/2004 | Lamson et al. | |
| 2004/0039371 A1 | 2/2004 | Tockman et al. | |
| 2004/0116848 A1 | 6/2004 | Gardeski et al. | |
| 2004/0138562 A1 | 7/2004 | Makower et al. | |
| 2004/0176782 A1 | 9/2004 | Hanse et al. | |
| 2005/0010237 A1 | 1/2005 | Niazi | |
| 2005/0096727 A1 | 5/2005 | Allen et al. | |
| 2006/0015164 A1 | 1/2006 | Patridge et al. | |
| 2006/0122682 A1 * | 6/2006 | Sommer et al. | 607/127 |
| 2006/0135998 A1 | 6/2006 | Libbus et al. | |
| 2006/0206166 A1 | 9/2006 | Weiner | |
| 2006/0229677 A1 | 10/2006 | Moffitt et al. | |
| 2006/0241737 A1 | 10/2006 | Tockman et al. | |
| 2006/0247750 A1 | 11/2006 | Seifert et al. | |
| 2006/0259107 A1 | 11/2006 | Caparso et al. | |
| 2006/0271115 A1 | 11/2006 | Ben-Ezra et al. | |
| 2006/0282145 A1 | 12/2006 | Caparso et al. | |
| 2007/0050005 A1 | 3/2007 | Lauro | |
| 2007/0100410 A1 | 5/2007 | Lamson et al. | |
| 2007/0135861 A1 | 6/2007 | Wallace et al. | |
| 2007/0191906 A1 | 8/2007 | Iyer et al. | |
| 2007/0282412 A1 | 12/2007 | Soltis et al. | |
| 2008/0091241 A1 | 4/2008 | Ben-Ezra et al. | |
| 2010/0023088 A1 | 1/2010 | Stack et al. | |

FOREIGN PATENT DOCUMENTS

| | | |
|---|---|---|
| DE | 10103288 A1 | 8/2002 |
| EP | 0688577 A1 | 12/1995 |
| WO | WO2005/065771 A1 | 7/2005 |
| WO | WO2006/098996 A1 | 9/2006 |
| WO | WO2006/110338 A1 | 10/2006 |

OTHER PUBLICATIONS

Bilgutay et al, "Vagal Tuning—A New Concept in the Treatment of Supraventricular Arrhythmias, Angina Pectoris, and Heart Failure," *Journal of Thoracic Cardiovascular Surgery* 56(1): 71-82, Jul. 1968.

Braunwald et al., "Carotid Sinus Nerve Stimulation in the Treatment of Angina Pectoris and Supraventricular Tachycardia," *California Medicine* 112(3): 41-50, Mar. 1970.

Armour, "Instant to Instant Reflex Cardiac Regulation," Cardiology 61: 309-328, 1976.

Schwartz et al., "Effect of dorsal root section on the arrhythmias associated with coronary occlusion," *American Journal of Physiology* 231(3): 923-928, Sep. 1976.

Blair et al., "Responses of Thoracic Spinothalamic Neurons to Intracardiac Injection of Bradykinin in the Monkey," *Circulation Research* 51(1): 83-94, Jul. 1982.

Ammons et al., "Vagal Afferent Inhibition of Spinothalamic Cell Responses to Sympathetic Afferents and Bradykinin in the Monkey," *Circulation Research* 53(5): 603612, Nov. 1983.

Blair et al., "Responses of Thoracic Spinothalamic and Spinoreticular Cells to Coronary Artery Occlusion," *Journal of Neurophysiology* 51(4): 636-648, Apr. 1984.

Ammons et al., "Effects of intracardiac bradykinin on $T_2$-$T_5$ medial spinothalamic cells," *American Journal of Physiology* 249: R147-R152, 1985.

Blair et al., "Activation of Feline Spinal Neurones by Potentiated Ventricular Contractions and Other Mechanical Cardiac Stimuli," *Journal of Physiology* 404: 649-667, 1988.

Schwartz et al., "Autonomic Mechanisms and Sudden Death—New Insights From Analysis of Baroreceptor Reflexes in Conscious Dogs With and Without a Myocardial Infarction," *Circulation* 78(4): 969-979, Oct. 1988.

Hobbs et al., "Cardiac and Abdominal Vagal Afferent Inhibition of Primate $T_9$-$S_1$ Spinothalamic Cells," *The American Physiological Socitey* 257: R889-R895, 1989.

Butler et al., "Cardiac Responses to Electrical Stimulation of Discrete Loci in Canine Atrial and Ventricular Ganglionated Plexi," *The American Physiological Society* 259: H1365-H1373, 1990.

Hull et al., "Heart Rate Variability Before and After Myocardial Infarction in Conscious Dogs at High and Low Risk of Sudden Death," *The American College of Cardiology* 16(4): 978-985, Oct. 1990.

Armour, "Intrinsic Cardiac Neurons," *Journal of Cardiovascular Electrophysiology* 2(4): 331-341, Aug. 1991.

Chandler et al., "Effects of Vagal Afferent Stimulation on Cervical Spinothalamic Tract Neurons in Monkeys," *Pain* 44: 81-87, 1991.

Linderoth et al., "Effects of Sympathectomy on Skin and Muscle Microcirculation During Dorsal Column Stimulation: Animal Studies," *Neurosurgery* 29(6): 874-879, 1991.
Vanoli et al., "Vagal Stimulation and Prevention of Sudden Death in Conscious Dogs With a Healed Myocardial Infarction," *Circulation Research* 68(5): 1471-1481, May 1991.
Cardinal et al., "Distinct Activation Patterns of Idioventricular Rhythms and Sympathetically-Induced Ventricular Tachycardias in Dogs With Atrioventricular Block," *PACE* 15: 1300-1316, Sep. 1992.
Fu et al., "Vagal Afferent Fibers Excite Upper Cervical Neurons and Inhibit Activity of Lumbar Spinal Cord Neurons in the Rat," *Pain* 51: 91-100, 1992.
Hobbs et al., "Evidence That $C_1$ and $C_2$ Propriospinal Neurons Meditate the Inhibitory Effects of Viscerosomatic Spinal Afferent Input on Primate Spinothalamic Tract Neurons," *Journal of Neurophysiology* 67(4): 852-860, Apr. 1992.
Hobbs et al., "Segmental Organization of Visceral and Somatic Input Onto $C_3$-$T_6$ Spinothalamic Tract Cells of the Monkey," *Journal of Neurophysiology* 68(5): 1575-1588, Nov. 1992.
Chandler et al., "A Mechanism of Cardiac Pain Suppression by Spinal Cord Stimulation: Implications for Patients With Angina Pectoris," *European Heart Journal* 14: 96-105, 1993.
Huang et al., "Effects of Transient Coronary Artery Occlusion on Canine Intrinsic Cardiac Neuronal Activity," *Integrative Physiological and Behavioral Science* 28(1): 5-21, Jan.-Mar. 1993.
Adamson et al., "Unexpected Interaction Between β-Adrenergic Blockade and Heart Rate Variability Before and After Myocardial Infarction—A Longitudinal Study in Dogs at High and Low Risk for Sudden Death," *Circulation* 90(2): 976-982, Aug. 1994.
Ardell, "Structure and Function of Mammalian Intrinsic Cardiac Neurons," Neurocardiology: 95-114, 1994.
Armour, "Peripheral Autonomic Neuronal Interactions in Cardiac Regulation," *Neurocardiology*: 219-244, 1994.
Foreman, "Spinal Cord Neuronal Regulation of the Cardiovascular System," *Neurocardiology*: 245-276, 1994.
Hull et al., "Exercise Training Confers Anticipatory Protection From Sudden Death During Acute Myocardial Ischemia," *Circulation* 89(2): 548-552, Feb. 1994.
Linderoth et al., "Sympathetic Mediation of Peripheral Vasodilation Induced by Spinal Cord Stimulation: Animal Studies of the Role of Cholinergic and Adrenergic Receptor Subtypes," *Neurosurgery* 35(4): 711-719, Oct. 1994.
Yuan et al., "Gross and Microscopic Anatomy of the Canine Intrinsic Cardiac Nervous System," *The Anatomical Record* 239: 75-87, 1994.
Armour, "Intrinsic Cardiac Neurons Involved in Cardiac Regulation Possess $alpha_1$, $alpha_2$, $beta_1$ and $beta_2$-Adrenoreceptors," *Can. J. Cardiol.* 13(3): 277-284, Mar. 1997.
Cardinal et al., "Reduced Capacity of Cardiac Efferent Sympathetic Neurons to Release Noradrenaline and Modify Cardiac Function in Tachycardia-Induced Canine Heart Failure," *Can. J. Physiol. Pharmacol.* 74: 1070-1078, 1996.
Chandler et al., "Vagal, Sympathetic and Somatic Sensory Inputs to Upper Cervical ($C_1$-$C_3$) Spinothalamic Tract Neurons in Monkeys," *Journal of Neurophysiology* 76(4): 2555-2567, 1996.
Zhang et al., "Thoracic Visceral Inputs Use Upper Cervical Segments to Inhibit Lumbar Spinal Neurons in Rats" *Brain Research* 709: 337-342,1996.
Armour et al., "Gross and Microscopic Anatomy of the Human Intrinsic Cardiac Nervous System," *The Anatomical Record* 247: 289-298, 1997.
Croom et al., "Cutaneous Vasodilation During Dorsal Column Stimulation Is Mediated by Dorsal Roots and CGRP," *Am. J. Physiol.* 272 (*Heart Circ. Physiol.* 41): H950-H957, 1997.
Hautvast et al., "Spinal Cord Stimulation in Chronic Intractable Angina Pectoris: A Randomized, Controlled Efficacy Study," *American Heart Journal*, 136(6): 1114-1120, 1998.
Barron et al., "Spinal Integration of Antidromic Mediated Cutaneous Vasodilation During Dorsal Spinal Cord Stimulation in The Rat," *Neuroscience Letters* 260: 173-176, 1999.
Foreman, "Mechanisms of Cardiac Pain," *Annu. Rev. Physiol.* 61: 143-167, 1999.
Linderoth et al., "Physiology of Spinal Cord Stimulation: Review and Update," *Neuromodulation* 2(3):150-164, 1999.
Qin et al., "Chemical Activation of Cervical Cell Bodies: Effects on Responses to Colorectal Distension in Lumbosacral Spinal Cord of Rats," *J Neurophysiol* 82: 3423-3433, 1999.
Chandler et al., "Intrapericardiac Injections of Algogenic Chemicals Excite Primate $C_1$-$C_2$ Spinothalamic Tract Neurons," *Am J. Physiol. Regulatory Integrative Comp. Physiol.* 279: R560-568, 2000.
Foreman et al., "Modulation of Intrinsic Cardiac Neurons by Spinal Cord Stimulation: Implications for Its Therapeutic Use in Angina Pectoris," *Cardiovascular Research* 47: 367-375, 2000.
Hopkins et al., "Pathology of Intrinsic Cardiac Neurons From Ischemic Human Hearts," *The Anatomical Record* 259: 424-436, 2000.
Kember et al., "Aperiodic Stochastic Resonance in a Hysteretic Population of Cardiac Neurons," *The American Physical Society* Physical Review E 61(2): 1816-1824, Feb. 2000.
Meyerson et al., "Spinal Cord Stimulation," *Bonica's Management of Pain*: 1857-1876, 2001.
Ardell, "Neurohumoral Control of Cardiac Function," *Heart Physiology and Pathophysiology, Fourth Edition*: 45-49, 2001.
Farrell et al., "Angiotensin II Modulates Catecholamine Release Into Interstitial Fluid of Canine Myocardium In Vivo," *Am J. Physiol. Heart Cir. Physiol.* 281: H813-H822, 2001.
Kingma, Jr. et al., "Neuromodulation Therapy Does Not Influence Blood Flow Distribution or Left-Ventricular Dynamics During Acute Myocardial Ischemia," *Autonomic Neuroscience: Basic & Clinical* 91: 47-54, 2001.
Tanaka et al., "Low Intensity Spinal Cord Stimulation May Induce Cutaneous Vasodilation via CGRP Release," *Brain Research* 896: 183-187, 2001.
Qin et al., "Responses and Afferent Pathways of Superficial and Deeper $C_1$-$C_2$ Spinal Cells to Intrapericardial Algogenic Chemicals in Rats," *J. Neurophysiol* 85:1522-1532, 2001.
Armour et al., "Long-Term Modulation of the Intrinsic Cardiac Nervous System by Spinal Cord Neurons in Normal and Ischaemic Hearts," *Autonomic Neuroscience: Basic & Clinical* 95: 71-79, 2002.
Chandler et al., "Spinal Inhibitory Effects of Cardiopulmonary Afferent Inputs in Monkeys: Neuronal Processing in High Cervical Segments," *J. Neurophysiol* 87: 1290-1302, 2002.
Cardinal et al., "Spinal Cord Activation Differentially Modulates Ischaemic Electrical Responses to Different Stressors in Canine Ventricles," *Autonomic Neuroscience: Basic & Clinical* 111: 37-47, 2004.
Ardell, "Intrathoracic Neuronal Regulation of Cardiac Function," *Basic and Clinical Neurocardiology* 118-152, 2004.
Siddons et al., "Special Considerations: Pacing in Acute Myocardial Infarction," *Cardiac Pacemakers* Chapter 11: 200-217, 1967.
Bluemel et al., "Parasympathetic Postganglionic Pathways to the Sinoatrial Node," *American Journal of Physiology* 259 (*Heart Circ. Physiol*. 28): H1504-H1510, 1990.
Cooper et al, "Neural Effects on Sinus Rate and Atrioventricular Conduction Produced by Electrical Stimulation from a Transvenous Electrode Catheter in the Canine Right Pulmonary Artery," *Circulation Research* 46(1): 48-57, Jan. 1980.
Randall et al, "Functional Anatomy of the Cardiac Efferent Innervation," *Neurocardiology* Chapter 1: 3-24, 1988.
U.S. Appl. No. 12/433,768, filed Apr. 30, 2009 entitled "Techniques for Placing Medical Leads for Electrical Stimulation of Nerve Tissue", by Burnes et al.
U.S. Appl. No. 12/433,766, filed Apr. 30, 2009 entitled "Techniques for Placing Medical Leads for Electrical Stimulation of Nerve Tissue", by Burnes et al.
U.S. Appl. No. 12/433,770, filed Apr. 30, 2009 entitled "Techniques for Placing Medical Leads for Electrical Stimulation of Nerve Tissue", by Burnes et al.
U.S. Appl. No. 12/433,773, filed Apr. 30, 2009 entitled "Techniques for Placing Medical Leads for Electrical Stimulation of Nerve Tissue", by Burnes et al.
XP-002532785, Michael A. Scherlag,et al., "Endovascular Neural Stimulation via a Novel Basket Electrode Catheter: Comparison of Electrode Configurations"; Journal of Interventional Cardiac Electrophysiology, vol. 4, 2000, (pp. 219-223).

International Search Report and Written Opinion from corresponding PCT Application Serial No. PCT/US2009/042438, mailed Jul. 23, 2009 (15 pgs).
International Search Report and Written Opinion from PCT Application Serial No. PCT/US2009/042434, mailed Jul. 3, 2009 (15 pages).
International Search Report and Written Opinion from PCT Application Serial No. PCT/US2009/042439, mailed Jul. 23, 2009 (13 pgs).
International Search Report and Written Opinion from PCT Application Serial No. PCT/US20009/042447, mailed Jul. 27, 2009 (14 pgs).
International Search Report and Written Opinion from PCT Application Serial No. PCT/US2009/042427, mailed Jul. 23, 2009, (15 pgs).

International Preliminary Report on Patentability for PCT/US2009/042438, mailed Nov. 11, 2010 (9 pp.).
Office Action from U.S. Appl. No. 12/433,768, dated Aug. 10, 2011, 7 pp.
Response to Office Action dated Aug. 10, 2011, from U.S. Appl. No. 12/433,768, filed Jan. 10, 2012, 7 pp.
Office Action from U.S. Appl. No. 12/433,770, dated May 9, 2011, 9 pp.
Office Action from U.S. Appl. No. 12/433,773, dated May 10, 2011, 11 pp.
*Ex Parte Quayle* Action from U.S. Appl. No. 12/433,768, dated Apr. 4, 2012, 4 pp.
Response to *Ex-Parte Quayle* Action dated Apr. 4, 2012, from U.S. Appl. No. 12/433,768, filed Jun. 4, 2012, 4 pp.

* cited by examiner

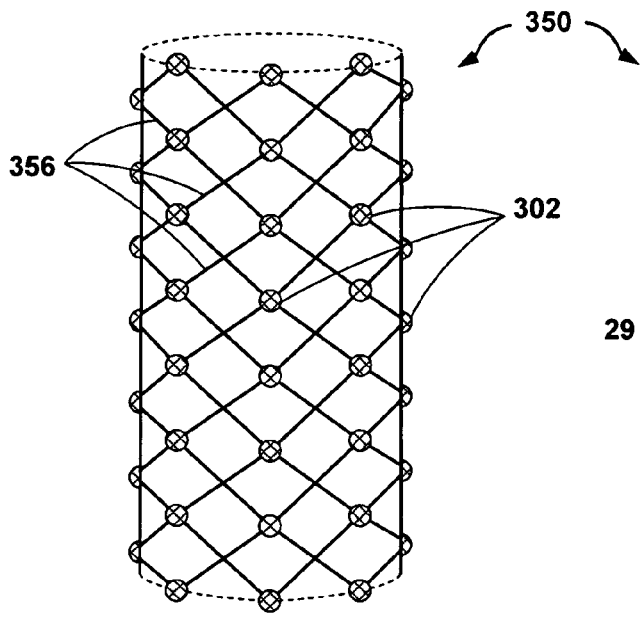
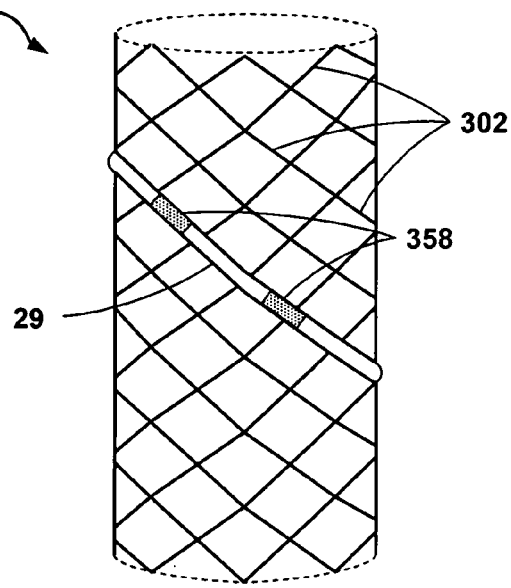
FIG. 18A  FIG. 18B
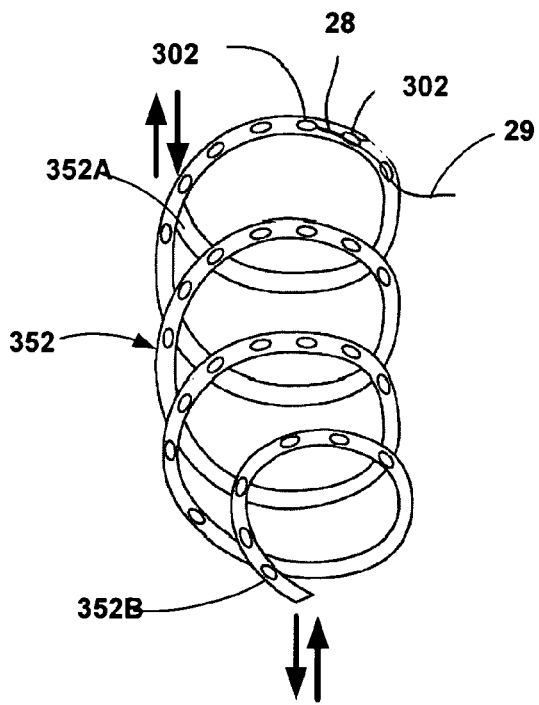
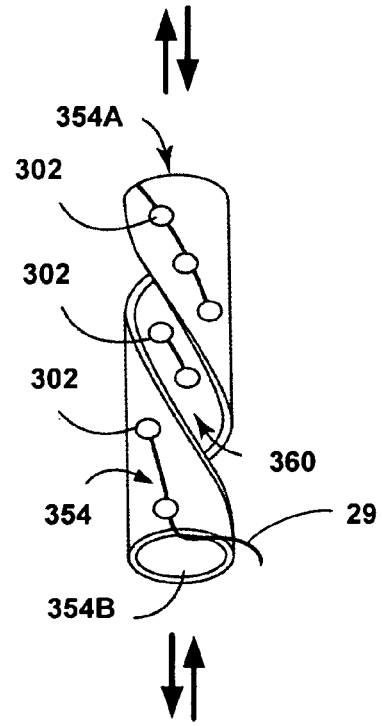
FIG. 18C  FIG. 18D

US 8,532,793 B2

TECHNIQUES FOR PLACING MEDICAL LEADS FOR ELECTRICAL STIMULATION OF NERVE TISSUE

This application claims the benefit of U.S. Provisional Application Nos. 61/007,542, 61/007,543, 61/190,045, and 61/190,046, all of which were filed Apr. 30, 2008, and the entire contents of each of which is incorporated herein by this reference.

TECHNICAL FIELD

The disclosure relates to medical devices and, more particularly, medical devices that deliver electrical stimulation therapy.

BACKGROUND

A wide variety of implantable medical devices ("IMD") that deliver therapy to or monitor a physiologic condition of a patient have been clinically implanted or proposed for clinical implantation in patients. Such devices may deliver therapy or monitor the heart, muscle, nerve, the brain, the stomach or other organs or tissues. In some cases, IMD's deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical activity or other physiological parameters. For example, electrodes or sensors may be located at a distal portion of the lead. A proximal portion of the lead is coupled to an IMD housing, which contains electronic circuitry such as stimulation generation and/or sensing circuitry. In some cases, electrodes or sensors are positioned on an IMD housing as an alternative or in addition to electrodes or sensors deployed on one or more leads.

One example IMD is an electrical stimulation device directed to nerve tissue stimulation, which is sometimes referred to as an implantable nerve stimulator or implantable neurostimulator ("INS"). One particular application of nerve tissue stimulation is vagal nerve stimulation. Vagal nerve stimulation may provide therapeutic effects for heart failure, as well as other conditions including, e.g., depression, epilepsy and various digestion conditions. Some vagal nerve stimulators, as well as nerve trunk stimulators in general, have employed cuff electrodes to surround the nerve tissue and anchor the stimulator lead and/or electrodes within a patient. Cuff electrodes have some disadvantages, however, including, that such electrodes require relatively invasive techniques for placing them within a patient. In the case of vagal nerve stimulation, cuff electrodes require an incision in the neck and dissection of the vagus from within the carotid sheath for placement around the nerve. Additionally, cuff electrodes are known to cause lesions or otherwise damage the nerve tissue, which may lead to deleterious effects on nerve function, as well as the development of scar tissue.

SUMMARY

In general, examples disclosed herein are directed to extra, intra, and transvascular medical lead placement techniques for arranging medical leads and electrical stimulation and/or sensing electrodes proximate nerve tissue within a patient.

In one example, an implantable medical lead system is configured to deliver electrical stimulation from within a lumen of a blood vessel within a patient to nerve tissue located adjacent to and outside of the blood vessel. The system includes a medical lead arranged within a lumen of the blood vessel. An electrode is connected toward a distal end of the lead adjacent the nerve tissue. An active fixation member is configured to anchor the lead to a wall of the blood vessel lumen.

In another example, a method includes deploying a lead through a lumen of a blood vessel to a target nerve tissue site. An electrode connected to the lead is arranged within the blood vessel lumen adjacent the nerve tissue. The lead is actively fixed to a wall of the blood vessel lumen.

The details of one or more examples according to this disclosure are set forth in the accompanying drawings and the description below. Other features, objects, and advantages will be apparent from the description and drawings, and from the claims.

BRIEF DESCRIPTION OF DRAWINGS

FIGS. 18A-18D are schematic illustrations of different examples of a cylindrical lead member that is expandable and contractible for deployment and redeployment within a blood vessel.

DETAILED DESCRIPTION

Figure 1A:
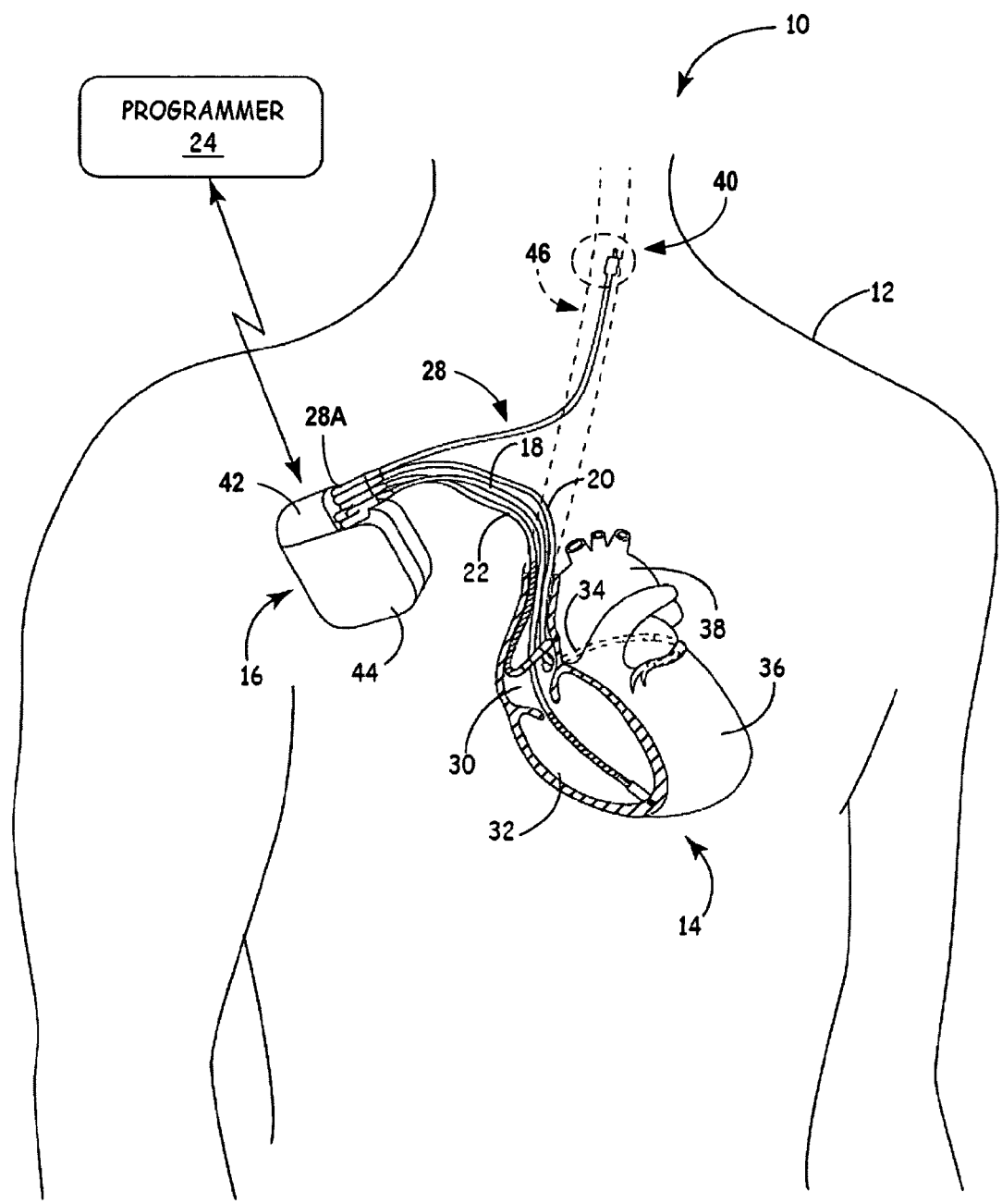
FIG. 1A is a conceptual diagram illustrating an example therapy system including an implantable medical device (IMD) that delivers cardiac and nerve tissue stimulation to a patient.

In general, this disclosure is directed toward techniques for placing medical leads proximate nerve tissue within a patient for electrical stimulation of the tissue without the use of potentially deleterious electrode configurations including e.g., cuff electrodes. Techniques disclosed herein are also generally directed to flexible placement techniques and structures that provide for one or more temporary lead placements and stimulation tests, prior to chronically placing the leads within the patient for nerve tissue stimulation. Furthermore, techniques according to this disclosure are adapted to enable minimally invasive introduction of the medical leads into the patient. Implantable electrical stimulation systems and methods in accordance with this disclosure may be used to deliver therapy to patients suffering from conditions that range from chronic pain, tremor, Parkinson's disease, and epilepsy, to urinary or fecal incontinence, sexual dysfunction, obesity, spasticity, and gastroparesis. Specific types of electrical stimulation therapies for treating such conditions include, e.g., cardiac pacing, neurostimulation, muscle stimulation, or the like.

Systems disclosed generally include one or more medical leads adapted to be placed within a patient proximate nerve tissue targeted for electrical stimulation therapy. The leads include one or more electrodes that are arranged toward a distal end of the leads. In some examples, the leads are anchored at least proximate the distal end of the leads by or according to one or more structures or techniques described in detail below. The medical leads are connected to an electrical stimulator including a processor adapted to carry out the electrical stimulation of the target nerve tissue according to, e.g., one or more therapy programs stored in non-volatile memory. The electrical stimulator may include, generally, stimulation generation and/or sensing circuitry. In some examples, the stimulator may also include circuitry for cardiac rhythm therapy, e.g., one or more of pacing, cardioversion, and/or defibrillation therapy, to a heart of a patient. The stimulator may be located at a distance from the target tissue site and coupled to a proximal end of the leads. In another example, however, the electrical stimulator may include one or more electrodes or sensors on its housing or a member, element or structure coupled to the housing, may be placed in conjunction with the electrodes or sensors proximate the target nerve tissue site, and may be powered by, e.g., battery or a remote power source. In some examples, the electrical stimulator may be powered by radio frequency pulses delivered from either an external or a subcutaneously implanted RF transmitter to a receiver unit arranged with the stimulator, lead, and/or electrodes. In other examples, some part of the stimulator, lead, or electrodes may be composed of a piezo-electric material that can generate current when excited mechanically by ultra sound waves transmitted from an external or implanted source. In yet another example, two separate implantable devices, e.g. an INS and a cardiac therapy device are individually implanted and communicatively connected to one another. Placement of the leads and electrodes proximate the nerve tissue includes extravascular, intravascular, and transvascular placement structures and techniques.

The techniques disclosed herein are described generally in the context of stimulation of one of the vagus nerves on the vagal nerve trunk in the neck of a human patient. Vagal nerve stimulation is useful in treating various conditions including, e.g., heart failure, depression, epilepsy, and various gastrointestinal conditions. However, the methods and systems disclosed are also applicable to stimulation and treatment of other nerve tissues that are located in diverse locations. For example, the disclosed techniques may be used in the stimulation of a hypoglossal nerve. In other examples, a nerve plexus that forms a node of intersecting nerves including, e.g., the cervical, brachial, lumbar, sacral, or solar plexus may be stimulated using methods and systems according to this disclosure. Additionally, the techniques may be used for stimulation of nerve ganglia including, e.g., one or more ganglia of a nerve plexus.

As an additional example, the techniques disclosed herein may be used in the stimulation of vascular baroreceptors including, e.g., carotid baroreceptors. Baroreceptors are sensors located in blood vessels that detect the pressure of blood flowing therethrough, and can send messages to the central nervous system to increase or decrease total peripheral resistance and cardiac output. The receptors function by detecting the amount a blood vessel wall stretches, and sending a signal to the nervous system in response to the detected expansion of the vessel. Baroreceptors act as part of a negative feedback system called the baroreflex that returns blood pressure to a normal level as soon as there is a deviation from a typical pressure, such as, e.g., the mean arterial blood pressure.

Prior extravascular placement techniques have involved invasive implantation procedures because the target tissue, such as a vagus nerve must be dissected to place and anchor the leads proximate the nerve tissue. Additionally, prior extravascular placement techniques commonly included lead electrode fixation at the lead distal end using, e.g., cuff electrodes, which may have deleterious effects over time including, e.g., nerve tissue necrosis. Techniques described herein provide for extravascular placement of medical leads for nerve tissue stimulation using implantation procedures with reduced invasiveness and without the need to anchor the leads at or very near their distal end. In general, the disclosed techniques include placing a portion of a medical lead having an electrode in an extravascular space within a sheath of tissue within a patient, and adjacent nerve tissue that is also within the sheath of tissue. The lead is anchored offset from the electrode at least partially outside of the sheath. As used herein, the term sheath of tissue generally refers to constraining connective tissue that holds together different biological structures within the body of a patient (e.g., a common carotid sheath).

Intra or transvascular lead placement proximate the target nerve tissue, on the other hand, generally requires minimally invasive surgical techniques because the leads may be guided to the site through a blood vessel, e.g., a vein or artery, that may be readily accessible, e.g., transcutaneously through a small incision. Intra and transvascular lead placement techniques described herein may facilitate placing the distal end of the lead in close proximity of the target nerve tissue, the relative position of which with respect to an adjacent blood vessel may vary from patient-to-patient. Additionally, guided transvascular lead placement as described herein may avoid safety risks of such procedures including, e.g., piercing adjacent vessels, such as an artery.

Some example intravascular techniques include structures and methods for deployment of one or more medical leads at a first location, testing stimulation at the first location, and, depending on the efficacy of the stimulation provided by electrodes on the leads at the first location, redeploying the leads to a second location. In one example, lead placement is improved by locating target nerve tissue with a sensor including, e.g., an intravascular ultrasound (IVUS) imaging system and/or measuring the efficacy of test electrical stimulation pulses from an electrode on the lead through a blood vessel adjacent the target tissue. After a placement location is determined, one or more leads including one or more electrodes may be deployed into the vessel and anchored to a vessel wall near the target nerve tissue. In some examples, the electrodes may be anchored with a fixation member that actively engages tissue of the blood vessel wall. In another intravascular placement example, an expandable and contractible generally cylindrical lead member is temporarily deployable for testing multiple electrode locations and combinations before deploying the member for chronic stimulation of the target nerve tissue.

Transvascular techniques generally include improving lead placement by locating target nerve tissue with a sensor including, e.g., an IVUS imaging system, through a blood vessel adjacent the target tissue. After a placement location is determined, one or more leads including one or more electrodes may be deployed through the vessel wall and anchored to the vessel wall or other tissue near the target nerve tissue.

The extra, intra, and transvascular lead placement techniques disclosed may also benefit, in some examples, from electrode pairs arranged in flanking, non-contacting relationship with the target nerve tissue. In one example, multiple leads are arranged longitudinally on opposing sides of the target nerve tissue, and include electrodes in non-contacting relationship with the target nerve tissue. In another example, one lead that includes multiple electrodes is employed such that at least two of the electrodes are arranged in flanking, non-contacting relationship with the target nerve tissue. Such flanking, non-contacting electrode arrangements may provide one or more anode and cathode electrode combinations for electrical stimulation across the target nerve tissue without the deleterious effects of tissue contacting techniques, such as may be caused by cuff electrodes.

FIG. 1A is a conceptual diagram illustrating an example therapy system 10 that provides cardiac rhythm therapy and nerve tissue stimulation therapy to patient 12. Therapy system 10 includes implantable medical device (IMD) 16, which is connected (or "coupled") to leads 18, 20, 22, 28, and programmer 24. IMD 16 may be subcutaneously or submuscularly implanted in the body of a patient 12 (e.g., in a chest cavity, lower back, lower abdomen, or buttocks of patient 12).

IMD 16 may include a cardiac therapy module (not shown in FIG. 1A) and a neurostimulation module (not shown in FIG. 1A) enclosed within outer housing 44. The cardiac therapy module may generate and deliver cardiac rhythm management therapy to heart 14 of patient 12, and may include, for example, an implantable pacemaker, cardioverter, and/or defibrillator that provide therapy to heart 14 of patient 12 via electrodes coupled to one or more of leads 18, 20, and 22. In some examples, the cardiac therapy module may deliver pacing pulses, but not cardioversion or defibrillation pulses, while in other examples, the cardiac therapy module may deliver cardioversion or defibrillation pulses, but not pacing pulses. In addition, in further examples, cardiac therapy module may deliver pacing, cardioversion, and defibrillation pulses. IMD 16 may deliver pacing that includes one or both of anti-tachycardia pacing (ATP) and cardiac resynchronization therapy (CRT).

The neurostimulation module of IMD 16 may include a signal generator that generates and delivers electrical stimulation to a tissue site of patient 12, e.g., tissue proximate a vagus nerve or other target nerve tissue of patient 12. In some examples, the tissue site may include a peripheral nerve. As previously indicated, in some examples, the tissue site may include a nerve plexus that forms a node of intersecting nerves including, e.g., the cervical, brachial, lumbar, sacral, or solar plexus. Additionally, the techniques may be used for stimulation of nerve ganglia including, e.g., one or more ganglia of a nerve plexus. As an additional example, the techniques disclosed herein may be used in the treatment of vascular baroreceptors including, e.g., carotid baroreceptors. In the example shown in FIG. 1A, electrodes of lead 28 are position to deliver electrical stimulation to target tissue site 40 proximate a vagus nerve of patient 12. The vagus nerve is primarily referred to herein as an example target nerve for neurostimulation therapy.

In some examples, delivery of electrical stimulation to a nerve tissue site may provide cardiac benefits to patient 12. For example, delivery of electrical stimulation to a peripheral nerve tissue site by IMD 16 may help treat heart failure. In addition, delivery of electrical stimulation to a nerve of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma. In addition, delivery of electrical stimulation to a nerve may complement antitachycardia pacing or provide back-up therapy to cardiac therapy delivered by IMD 16. In some examples, IMD 16 may deliver electrical stimulation therapy to a nerve of patient 12 via a lead implanted within vasculature (e.g., a blood vessel) of patient 12. In other examples, stimulation may be delivered by IMD 16 via a lead located in extravascular tissue, e.g., when lead 28 is not implanted within vasculature, such as within a vein or artery. Additional examples include transvascular placement of a lead from within a blood vessel of patient 12 adjacent the target tissue site, through the wall of the blood vessel, and into an extravascular space, where the target nerve tissue may be located.

In the example shown in FIG. 1A, the neurostimulation therapy module of IMD 16 delivers electrical stimulation therapy to a nerve of patient 12 via a lead implanted within vasculature (e.g., a blood vessel) of patient 12. In particular, lead 28 is implanted such that electrodes of lead 28 are positioned within jugular vein 46 proximate the vagus nerve (not shown). Stimulation of a parasympathetic nerve of patient 12 may help slow intrinsic rhythms of heart 14, which may complement antitachyarrhythmia therapy (e.g., antitachycardia pacing, cardioversion or defibrillation) delivered by IMD 16. In this way, neurostimulation therapy may help control a heart rate of patient 12 or otherwise control cardiac function.

In other examples, electrodes of lead 28 may be positioned to deliver electrical stimulation to any other suitable nerve (e.g., a peripheral nerve) or nerve tissue in patient 12. In some examples, the neurostimulation module of IMD 16 may deliver electrical stimulation to other sympathetic or parasympathetic nerves, baroreceptors, hypoglossal nerve, carotid sinus, or a cardiac branch of the vagal trunk of patient 12 in order to facilitate or compliment the delivery of therapy by the cardiac therapy module of IMD 16.

In FIG. 1A, leads 18, 20, and 22 extend into the heart 14 of patient 12 to sense electrical activity (electrical cardiac signals) of heart 14 and/or deliver electrical stimulation (cardiac therapy) to heart 14. In particular, right ventricular (RV) lead 18 extends through one or more veins (not shown), superior vena cava (not shown), and right atrium 30, and into right ventricle 32. Left ventricular (LV) coronary sinus lead 20 extends through one or more veins, the vena cava, right atrium 30, and into coronary sinus 34 to a region adjacent to the free wall of left ventricle 36 of heart 14. Right atrial (RA) lead 22 extends through one or more veins and the vena cava, and into right atrium 30 of heart 14. In other examples, IMD 16 is additionally or alternatively coupled to extravascular, e.g., epicardial or subcutaneous electrodes, via leads for cardiac sensing and/or stimulation.

The cardiac therapy module may sense electrical signals attendant to the depolarization and repolarization of heart 14 via electrodes (not shown in FIG. 1A) coupled to at least one of the leads 18, 20, 22. These electrical signals within heart 14 may also be referred to as cardiac signals or electrical cardiac signals. In some examples, the cardiac therapy module provides pacing pulses to heart 14 based on the electrical cardiac signals sensed within heart 14. The configurations of electrodes used by the cardiac therapy module for sensing and pacing may be unipolar or bipolar. The cardiac therapy module may also provide defibrillation therapy and/or cardioversion therapy via electrodes located on at least one of the leads 18, 20, 22 and one or more electrodes on housing 44 of IMD 16. IMD 16 may detect arrhythmia of heart 14, such as fibrillation of ventricles 32 and 36, and deliver defibrillation therapy to heart 14 in the form of electrical pulses via one or more of leads 18, 20, and 22. In some examples, the cardiac therapy module may be programmed to deliver a progression of therapies, e.g., pulses with increasing energy levels, until a fibrillation of heart 14 is stopped. IMD 16 detects fibrillation employing one or more fibrillation detection techniques known in the art.

The neurostimulation therapy module of IMD 16 may provide a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector 42 of IMD 16 either directly or indirectly (e.g., via a lead extension). In particular, conductors disposed in the lead body of lead 28 may electrically connect stimulation electrodes (and sense electrodes, if present) of lead 28 to IMD 16. In some examples, the neurostimulation therapy module of IMD 16 may be electrically coupled to more than one lead directly or indirectly (e.g., via a lead extension).

In the example of FIG. 1A, one or more electrodes of lead 28 are intravascularly implanted in patient 12 proximate to target tissue stimulation site 40, e.g., proximate to a vagus nerve (not shown). In particular, one or more neurostimulation electrodes of lead 28 are implanted within jugular vein 46. Generally speaking, implanting lead 28 near the vagus nerve of patient 12 may be useful for delivering neurostimulation therapy to the vagus nerve without requiring lead 28 to be subcutaneously implanted in patient 12. Implanting lead 28 intravascularly within jugular vein 46 may thereby be useful for reducing trauma to patient 12, e.g., because lead 28 is not tunneled through subcutaneous tissue from IMD 16 to target site 40. As described in greater detail with reference to FIGS. 4-22, in other examples according to this disclosure, lead 28 may be extravascularly or transvascularly placed proximate target tissue stimulation site 40, e.g., proximate a vagus nerve of patient 12.

The distal portion of lead 28 may include one or more electrodes (not shown) for delivering neurostimulation to target stimulation site 40. Various electrode configurations of lead 28 are described in further detail with respect to FIGS. 2 and 3. In some examples, lead 28 may also carry sense electrodes (not shown) to permit IMD 16 to sense electrical signals, such as electrical cardiac signals or electrical nerve signals from the vagus nerve or other nerve tissue at which therapy is directed. Lead 28 may also carry one or more sensors including, e.g., sense electrodes, pressure sensors, ultrasound sensors, motion sensors, acoustic sensors (heart rate), optical sensors, blood oxygen sensors, posture state sensors, respiration sensors, venous biomarker sensors, temperature sensors or other devices that may detect physiological signals of patient 12 indicative of the efficacy of neurostimulation therapy delivered to the patient by stimulation electrodes.

In some examples, IMD 16 may deliver an electrical stimulation signal via one or more of the electrodes of lead 28, and analyze a physiological signal to detect a response to the stimulation signal. In one such example, IMD 16 analyzes an electrical nerve signal to detect a response to the stimulation signal. The characteristic of the electrical nerve signal that indicates the desired response to the delivery of the electrical stimulation signal by the neurostimulation therapy module of IMD 16 may be, for example, an amplitude or frequency of the electrical signal. The target characteristic of the electrical nerve signal may be determined by a clinician at any suitable time when lead 28 is known to be in the desired location within patient 12, e.g., immediately after lead 28 is implanted within patient 12.

The electrical nerve signal may be an electrical signal generated by a nerve, such as the target nerve for the neurostimulation therapy or a branch thereof, in response to an electrical stimulation signal delivered by the electrodes of lead 28. The response to the electrical stimulation signal may indicate, for example, whether the neurostimulation signal captured the nerve, and, therefore, is within a desired distance of the nerve. In the example shown in FIG. 1A, the target nerve is a vagus nerve, however, other types of nerves are contemplated for the neurostimulation therapy. The electrical nerve signal may be sensed between two or more electrodes of lead 28. IMD 16 may analyze the electrical nerve signal for a response, for example, by measuring an amplitude of the electrical nerve signal and comparing the determined value to a threshold value. In this case, the electrical nerve signal may have a baseline amplitude value and a response to the stimulation signal may be characterized by a spike in amplitude. The nerve response may be characterized by an amplitude or other characteristics of a sensed electrical signal.

In the context of lead placement techniques disclosed herein, sensed physiological signals may be used to determine the efficacy of neurostimulation delivered by electrodes on lead 28 to target nerve tissue. In some examples, lead 28 may be intra, extra, or transvascularly placed proximate the nerve tissue and electrodes on lead 28 may deliver test stimulation pulses to the nerve tissue in order to test the placement of lead 28 within patient 12 relative to the nerve tissue. Various physiological signals may be observed to measure the efficacy of the test stimulation, and thereby the need to reposition lead 28 relative the target nerve tissue. In some examples, test treatment efficacy may be indicated by, e.g., ECG, heart rate, blood pressure, blood flow, blood oxygen content, blood biomarker content, cardiac output, and/or breathing, of patient 12. Additionally, T-wave morphology, heart rate variability, contractility, and atrioventricular (AV) intervals may be observed as an indication of test treatment efficacy. These and other physiological signals may be detected in a variety of ways including sensing the signals using sense electrodes, pressure sensors, ultrasound sensors, motion sensors or other devices. In other examples, physiological reactions of patient 12 may be observed or measured by, e.g., a clinician.

In the case one or more sensors are employed to detect physiological signals of patient 12, such devices may be arranged in a variety of locations depending on device configuration and the particular signal being detected. For example, the efficacy of electrical stimulation of a vagus nerve may be measured by an accelerometer arranged in the neck of patient 12 that determines if stimulation of neck muscles or the phrenic nerve is occurring with or instead of stimulation of a vagus nerve. In another example, a pressure sensor arranged coincident with or connected to lead 28 may measure blood pressure by detecting the pressure within a vessel in which lead 28 is placed. A pressure sensor, or other type of physiological feedback sensor, may also, in some examples, be connected to a delivery catheter configured to place lead 28 within patient 12. In still another example, a cardiac therapy module included in IMD 16 may employ one or more electrodes arranged on or within heart 14 of patient 12 to, e.g., to monitor electrical activity of heart 14 via an electrogram (EGM) or electrocardiogram (ECG) signal. In other examples, venous biomarker sensors configured to sense, e.g., inflammation markers or catecholamines may be used to measure the effect of the stimulation and provide feedback to IMD 16.

Figure 1B:
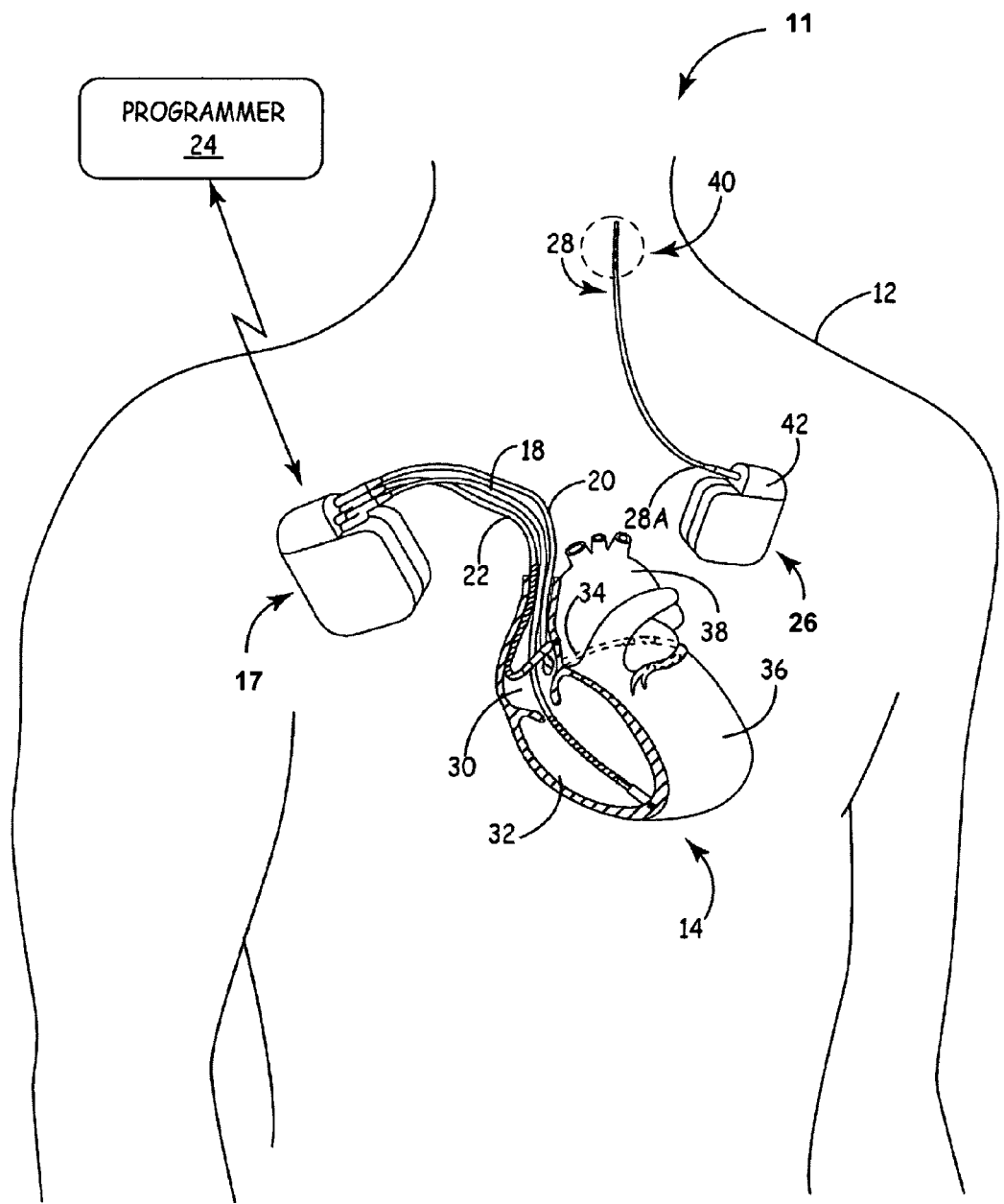
FIG. 1B is a conceptual diagram illustrating an example therapy system including an implantable cardiac device (ICD) and an implantable neurostimulator (INS).

The extra, intra, and transvascular lead placement techniques described herein are applicable for implantation of a variety of implantable therapy systems including, e.g., system 10 of FIG. 1A, as well as systems that do not deliver cardiac stimulation and/or provide cardiac sensing, or, as with the example of FIG. 1B, deliver cardiac therapy using a device that is separate from and in addition to an implantable neurostimulator.

As illustrated in FIG. 1A, system 10 may include a programmer 24. IMD 16 may transmit information to and receive information from programmer 24 related to the operation of IMD 16 and/or the delivery of therapy by IMD 16 to patient 12. Upon receiving the information, programmer 24 may upload the received information to a remote server, from which a clinician may access the data (such as a remote server of the CareLink Network available from Medtronic, Inc. of Minneapolis, Minn.). A clinician may also access the information directly by interacting with programmer 24. Furthermore, the clinician may program various aspects of the operation of IMD 16 remotely by accessing a remote server that communicates with IMD 16 via a network and programmer 24, or locally program IMD 16 by physically interacting with programmer. In some examples, the clinician may interact with programmer 24 to, e.g., program select values for operational parameters of IMD 16.

In some examples, programmer 24 may be a handheld computing device or a computer workstation. The user may use programmer 24 to program aspects of the neurostimulation module. The therapy parameters for the neurostimulation module of IMD 16 may include an electrode combination for delivering neurostimulation signals, as well as an amplitude, which may be a current or voltage amplitude, and, if the neurostimulation module delivers electrical pulses, a pulse width, and a pulse rate for stimulation signals to be delivered to patient 12. The electrode combination may include a selected subset of one or more electrodes located on implantable lead 28 coupled to IMD 16 and/or a housing of IMD 16. The electrode combination may also refer to the polarities of the electrodes in the selected subset. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset.

As another example, programmer 24 may be used by a user, e.g., a clinician while a medical lead is placed within patient in accordance with this disclosure to retrieve or view sensor feedback during the implantation of the lead. In one example, a physician uses programmer 24 to retrieve and/or view physiological signals sensed by one or more sensors in response to test electrical stimulation pulses delivered to patient 12 during the placement of lead 12 adjacent a vagus nerve. In this manner, the physician employs programmer 24 to determine the efficacy of the test stimulation delivered by lead 28, and thereby the position of lead 28 relative to the vagus nerve. In another example, the physician may also use programmer 24 to view an imaging field produced by an IVUS imaging system connected to a delivery catheter used to place lead 28, and electrodes connected thereto intra or transvascularly within patient 12. In this manner, the physician may employ programmer 24 to view, in real time, the placement of lead 28 within patient 12 relative to target nerve tissue and a blood vessel in which or through which the lead is placed.

Programmer 24 may communicate with IMD 16 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

FIG. 1B is a conceptual diagram illustrating another example therapy system 11 that includes separate implantable cardiac device (ICD) 17 and implantable electrical stimulator 26. ICD 17 is connected to leads 18, 20, and 22, and programmer 24, while electrical stimulator 26 is coupled to lead 28 and may be communicatively connected to both ICD 17 and programmer 24. ICD 17 may be, for example, a device that provides cardiac rhythm management therapy to heart 14, and may include, for example, an implantable pacemaker, cardioverter, and/or defibrillator, as described above with reference to IMD 16.

In some examples, ICD 17 may, in addition to or instead of delivering cardiac rhythm management therapy to heart 14, sense electrical cardiac signals of heart 14 and/or other physiological parameters of patient 12 (e.g., blood oxygen saturation, blood pressure, temperature, heart rate, respiratory rate, and the like), and store the electrical cardiac signals and/or other physiological parameters of patient 12 for later analysis by a clinician. In such examples, ICD 17 may be referred to as a patient monitoring device. Examples of patient monitoring devices include, but are not limited to, the Reveal Plus Insertable Loop Recorder, which is available from Medtronic, Inc.

of Minneapolis, Minn. For ease of description, ICD 17 will be referred to herein as a cardiac rhythm management therapy delivery device.

Therapy system 11 also includes implantable electrical stimulator 26, which is coupled to lead 28. Electrical stimulator 26 may also be referred to as an implantable neurostimulator ("INS") 26. INS 26 may be any suitable implantable medical device (IMD) that includes a signal generator that generates electrical stimulation signals that may be delivered via one or more electrodes on lead 28 to a nerve tissue site of patient 12, e.g., tissue proximate a vagus nerve.

In the example shown in FIG. 1B, electrodes of lead 28 are positioned outside the vasculature of patient 12 to deliver electrical stimulation to a vagus nerve (not shown) of patient 12. As described above, in other examples, stimulation may be delivered to a nerve tissue site via electrodes of an intravascular lead that is implanted within vasculature. In still other examples, stimulation may be delivered to a nerve tissue site within patient 12 via electrodes of a transvascular lead that is guided proximate the target tissue site intravascularly, i.e., through a vein, artery, or other blood vessel and then pierces a wall of the vessel to be arranged adjacent the target tissue outside of the blood vessel.

In the example shown in FIG. 1B, the components of ICD 17 and INS 26 are enclosed in separate housings, such that ICD 17 and INS 26 are physically separate devices. In contrast to the example of FIG. 1A in which the functionality of ICD 17 and INS 26 are be performed by IMD 16 that includes both a cardiac therapy module and an electrical stimulation therapy module. In applications in which cardiac and neurostimulation therapy operate cooperatively or sensing feedback is provided from heart 14 or a nerve tissue site within patient 12, ICD 17 and INS 26 of FIG. 1B may communicate with one another via one or more wireless communication techniques instead of being directly linked within the same device housing as in IMD 16 of therapy system 10 shown in FIG. 1A. For example, INS 26 may include one or more sensors that analyze an electrical nerve signal to detect a response to the stimulation signal delivered by ICD 17 and/or INS 26 to patient 12. ICD 17 and INS 26 may communicate wirelessly using, e.g., low frequency or radiofrequency (RF) telemetry.

Figure 2:
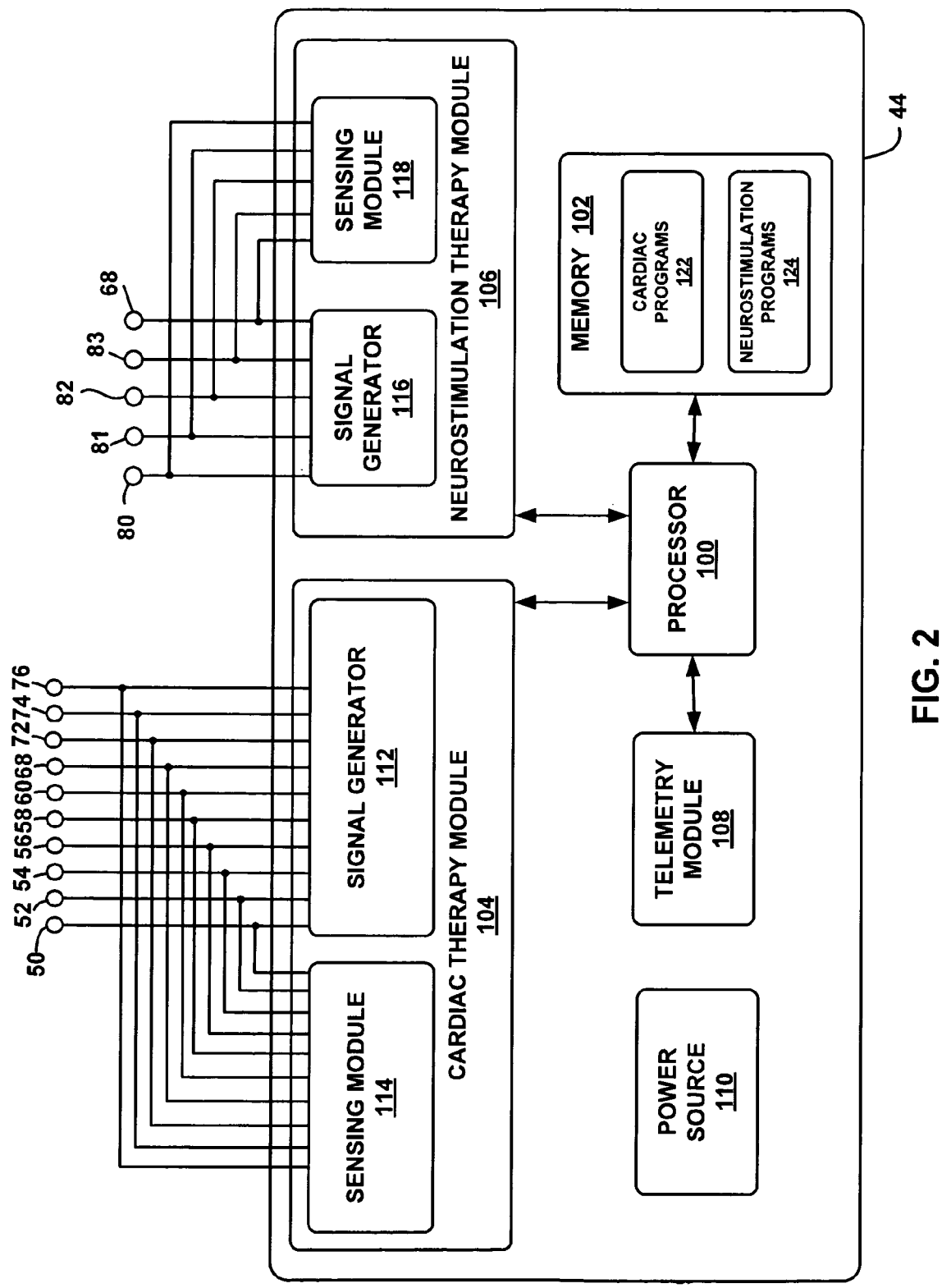
FIG. 2 is a functional block diagram of the IMD of FIG. 1A.

FIG. 2 is a functional block diagram of an example configuration of IMD 16 of FIG. 1A, which includes processor 100, memory 102, cardiac therapy module 104, neurostimulation therapy module 106, telemetry module 108, and power source 110. Cardiac therapy module 104 includes signal generator 112 and sensing module 114. Neurostimulation therapy module 106 includes signal generator 116 and sensing module 118. The components of IMD 16 shown in FIG. 2 may be substantially enclosed within a common, hermetically sealed outer housing 44 of IMD 16. In other examples including the example shown in FIG. 1B, components for carrying out the functions of cardiac therapy module 104 and neurostimulation therapy module 106 may be arranged in separate communicatively connected devices. Although cardiac therapy module 104 and neurostimulation therapy module 106 are illustrated as separate modules in FIG. 4, in some examples, cardiac therapy module 104 and neurostimulation module 106 and their respective components may share circuitry. For example, signal generators 112 and 116 may share common circuitry, e.g., a stimulation engine, charging circuitry, capacitors, and the like. Additionally, in some examples in which cardiac therapy module 104 and neurostimulation module 106 deliver stimulation in alternation, cardiac therapy module 104 and neurostimulation module 106 may share some or all stimulation generation circuitry.

Similarly, in some examples, sensing modules 114 and 118 may also share common circuitry, such as an analog-to-digital converter and the like.

Memory 102 includes computer-readable instructions that, when executed by processor 100, cause IMD 16 and processor 100 to perform various functions attributed to IMD 16 and processor 100 herein. In FIG. 2, memory 102 includes cardiac programs 122 that cardiac therapy module 104 uses for generating cardiac rhythm therapy for delivery to heart 14, and neurostimulation programs 124 that neurostimulation module 106 uses for generating neurostimulation therapy for delivery to target tissue site 40. Memory 102 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 100 may include any one or more of a microprocessor, a controller, a digital signal processor (DSP), an application specific integrated circuit (ASIC), a field-programmable gate array (FPGA), or equivalent discrete or integrated logic circuitry. In some examples, processor 100 may include multiple components, such as any combination of one or more microprocessors, one or more controllers, one or more DSPs, one or more ASICs, or one or more FPGAs, as well as other discrete or integrated logic circuitry. The functions attributed to processor 100 herein may be embodied as software, firmware, hardware or any combination thereof. Processor 100 may control cardiac therapy module 104 to deliver stimulation therapy according to a selected one or more of cardiac programs 122 stored in memory 102. In addition, processor 100 may control neurostimulation module 106 to delivering stimulation therapy according to a selected one or more of neurostimulation programs 124 stored in memory 102. Specifically, processor 100 may control cardiac therapy module 104 and/or neurostimulation module 106 to deliver electrical signals via electrode combinations with amplitudes, frequency, electrode polarities, and, in the case of stimulation pulses, pulse widths specified by the selected one or more cardiac and neurostimulation therapy programs 122, 124, respectively.

In the example shown in FIG. 2, cardiac therapy module 104 is electrically connected to electrodes 50, 52, 54, 56, 58, 60, 72, 74, and 76 of leads 18, 20, and 22 and housing electrode 68, and neurostimulation module 106 is electrically connected to electrodes 80-83 of lead 28 and housing electrode 68. In other examples, cardiac therapy module 104 and neurostimulation module 106 may be coupled to any suitable number of electrodes, which may comprise a greater number of electrodes or a fewer number of electrodes than that shown in the example of FIG. 2.

Cardiac therapy module 104 is configured to generate and deliver cardiac rhythm therapy to heart 14. For example, signal generator 112 of cardiac therapy module 104 may generate and deliver cardioversion or defibrillation shocks and/or pacing pulses to heart 14 via a selected combination of electrodes 50, 52, 54, 56, 58, 60, 72, 74, and 76 and housing electrode 68. Signal generator 112 of cardiac therapy module 104 is electrically coupled to electrodes 50, 52, 54, 56, 58, 60, 72, 74, and 76, e.g., via conductors of the respective lead 18, 20, 22, or, in the case of housing electrode 68, via an electrical conductor disposed within housing 44 of IMD 16.

Sensing module 114 monitors signals from at least one of electrodes 50, 52, 54, 56, 58, 60, 72, 74, and 76 in order to monitor electrical activity of heart 14, e.g., via an EGM or ECG signal. Sensing module 114 may also include a switching module (not shown in FIG. 4) to select a particular subset of available electrodes to sense heart activity. In this manner, sensing module 114 may detect R-waves, P-waves, or other cardiac electrical activity, and provide indications of their occurrence to processor 100. In some examples, processor may analyze a digitized the EGM or ECG to detect these or other morphological features of the EGM or ECG, to determine heart rates or intervals (e.g., R-R intervals) or sizes of features such as T-waves or QRS complexes, or provide any other known cardiac sensing and monitoring functionality.

Neurostimulation module 106 is configured to generate and deliver electrical stimulation therapy to a target site within patient 12 proximate nerve tissue, e.g., in order to modulate an autonomic nervous system or vascular tone. Example stimulation sites for neurostimulation module 106 include, but are not limited to, tissue proximate a vagus nerve or braches of a vagus nerve of patient 12. For example, signal generator 116 may generate stimulation signals that are delivered to a tissue site proximate a vagus nerve via a selected combination of electrodes 80-83 of lead 28 and/or housing electrode 68. The stimulation signals may be pulses as primarily described herein, or continuous time signals, such as sine waves.

Signal generator 116 may be a single or multi-channel signal generator. In particular, signal generator 116 may be capable of delivering, a single stimulation pulse, multiple stimulation pulses, or a continuous signal at a given time via a single electrode combination or multiple stimulation pulses at a given time via multiple electrode combinations. In some examples, however, neurostimulation therapy module 106 may be configured to deliver multiple channels on a time-interleaved basis. In this case, neurostimulation therapy module 106 may include a switching module (not shown) that serves to time division multiplex the output of the signal generator across different electrode combinations at different times to deliver multiple programs or channels of stimulation energy to patient 12.

Sensing module 118 of neurostimulation module 106 monitors signals from at least one of electrodes 80-83 of lead 28 and housing electrode 68 in order to monitor electrical activity of the target nerve tissue, e.g. nerve signals of a vagus nerve. For example, the amount of afferent and efferent signals of nerve fibers can be monitored. In one such example, the nerve signals of the left vagus nerve of patient 12 can be compared to the right vagus nerve and therapy may be delivered by neurostimulation module 106 and/or cardiac therapy module 104 as commanded by processor 100 based at least in part upon this comparison of sensed nerve tissue traffic. Conversely, in the context of lead placement techniques described herein, therapy may be delivered to a vagus nerve (e.g. left or right, or both) by one or more of electrodes 80-83 and sensing module 118 of neurostimulation module 106 and/or sensing module 114 of cardiac therapy module 104 as commanded by processor 100 may monitor afferent and efferent signals of vagal nerve fibers to measure the efficacy of the therapy.

Telemetry module 108 includes any suitable hardware, firmware, software or any combination thereof for communicating with another device, such as programmer 24 (FIG. 1). Under the control of processor 100, telemetry module 108 may receive downlink telemetry from and send uplink telemetry to programmer 24 with the aid of an antenna, which may be internal and/or external. Processor 100 may provide the data to be uplinked to programmer 24 and the control signals for the telemetry circuit within telemetry module 108, e.g., via an address/data bus. In some examples, telemetry module 108 may provide received data to processor 100 via a multiplexer.

The various components of IMD 16 are coupled to power source 100, which may include a rechargeable or non-rechargeable battery or a supercapacitor. A non-rechargeable battery may be selected to last for several years, while a rechargeable battery may be inductively charged from an external device, e.g., on a daily or weekly basis. Power source 100 may also include an external or a subcutaneously implanted RF transmitter that is configured to deliver power via radio frequency pulses to a receiver arranged with IMD 16 or one of the leads and/or electrodes of cardiac therapy module 104 and neurostimulation therapy module 106. In other examples, some part of IMD 16, or one of the leads or electrodes may be composed of a piezoelectric material that can generate current when excited mechanically by ultra sound waves transmitted from an external or implanted source.

In some examples, data generated by sensing module 114 or sensing module 118 and stored in memory 102 may be uploaded to a remote server, from which a clinician or another user may access the data to determine whether a potential sensing integrity issue exists. An example of a remote server includes the CareLink Network, available from Medtronic, Inc. of Minneapolis, Minn. An example system may include an external device, such as a server, and one or more computing devices that are coupled to IMD 16 and programmer 24 via a network.

In addition to the examples of FIGS. 1A, 1B, and 2 including cardiac therapy and neurostimulation therapy implemented in a single or separate devices, examples according to this disclosure also include a standalone INS device implanted within patient 12 and configured to function in a manner consistent with the description of neurostimulation therapy module 106 of IMD 16 or INS 26 shown in FIGS. 1A and 2, and 1B respectively.

Figure 3:
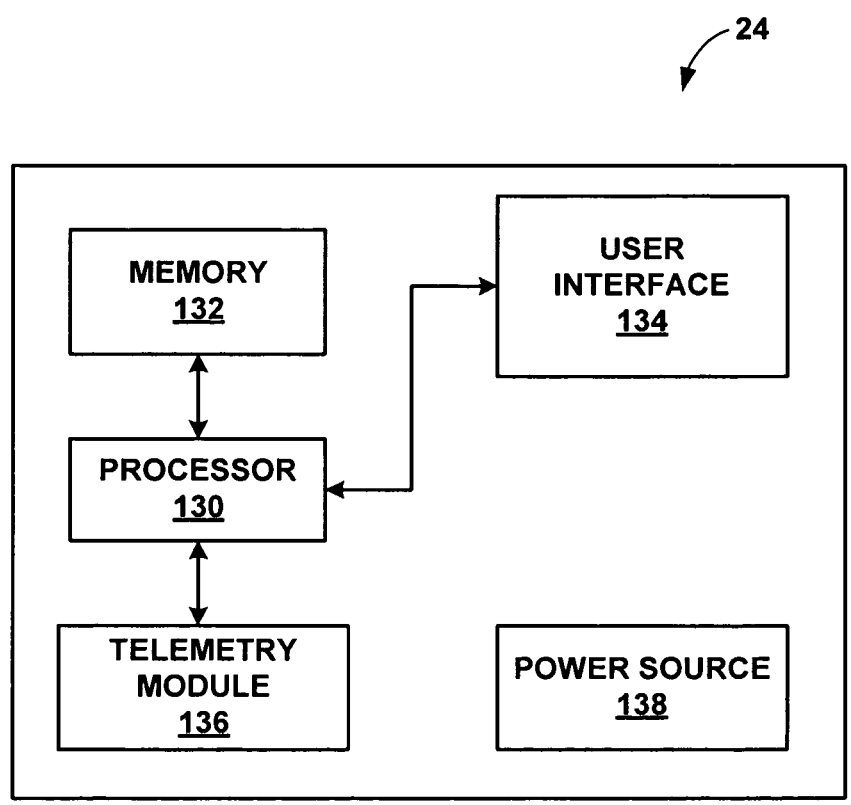
FIG. 3 is a functional block diagram of an example medical device programmer.

FIG. 3 is block diagram of example programmer 24 of FIGS. 1A and 1B. As shown in FIG. 3, programmer 24 includes processor 130, memory 132, user interface 134, telemetry module 136, and power source 138. Programmer 24 may be a dedicated hardware device with dedicated software for programming one or more of IMD 16, ICD 17, or INS 26. Alternatively, programmer 24 may be an off-the-shelf computing device running an application that enables programmer 24 to program one or more of IMD 16, ICD 17, or INS 26. For convenience and clarity, the description of FIG. 3 will be made with reference to the operation of programmer 24 with IMD 16. However, the components and functions of programmer 24 described herein are equally applicable to use with ICD 17, INS 26 or any other implantable medical device that may benefit from the functions provided by an external programming device such as programmer 24.

A user may use programmer 24 to select therapy programs (e.g., sets of stimulation parameters), generate new therapy programs, modify therapy programs through individual or global adjustments or transmit the new programs to IMD 16 (FIG. 1A). The therapy programs may be for either or both cardiac therapy module 104 and neurostimulation module 106 (FIG. 2). A clinician, e.g., may interact with programmer 24 via user interface 134, which may include a display to present a graphical user interface to a user, and a keypad or another mechanism for receiving input from a user.

Processor 130 can take the form of one or more microprocessors, DSPs, ASICs, FPGAs, programmable logic circuitry, or the like, and the functions attributed to processor 130 herein may be embodied as hardware, firmware, software or any combination thereof. Memory 132 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed proximate to the patient's body near the IMD 16 implant site, as described above with reference to FIG. 1A. Telemetry module 136 may be similar to telemetry module 108 of IMD 16 (FIG. 2).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation of programmer 24.

Figure 4:
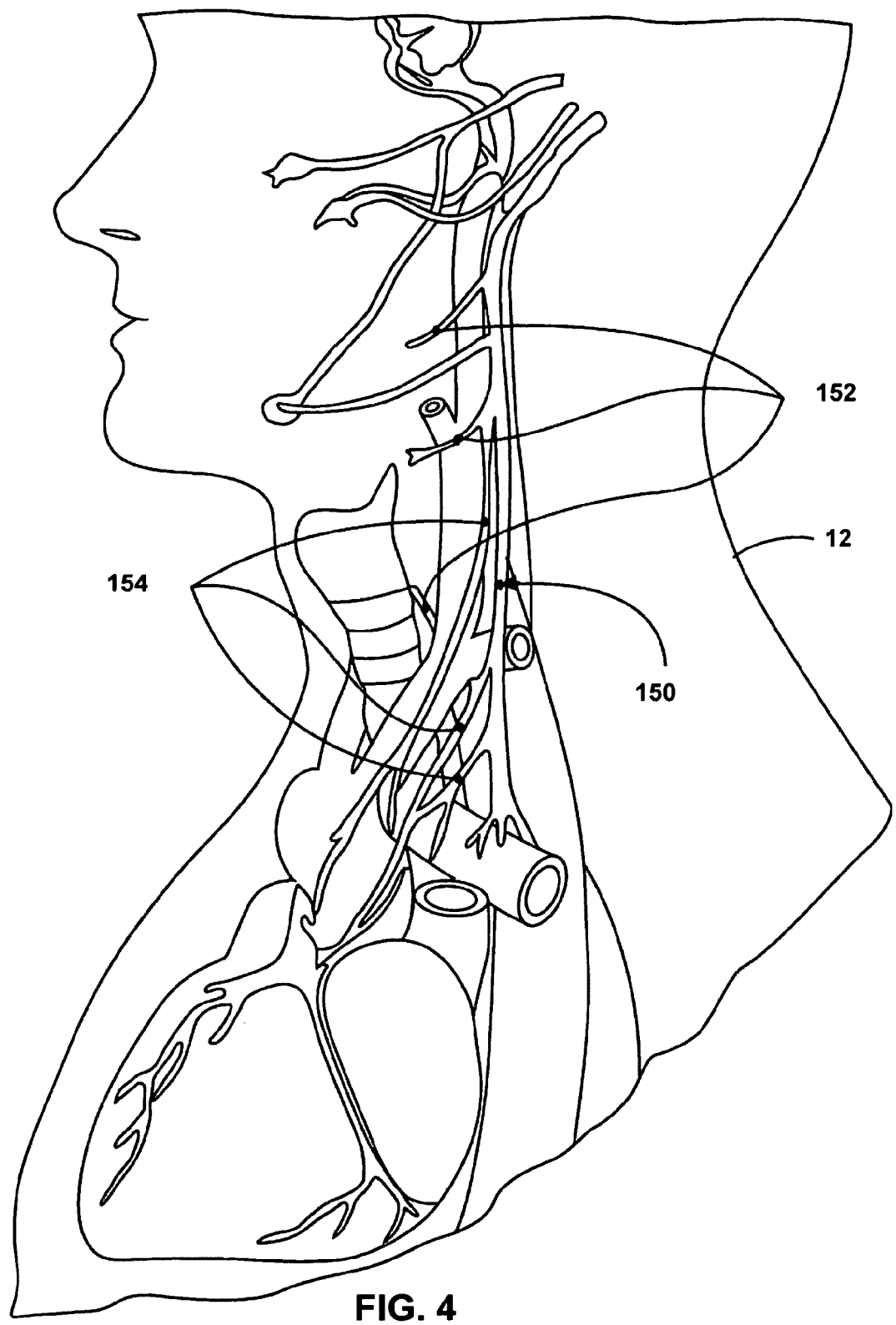
FIGS. 4 and 5 are schematic illustrations depicting relevant human anatomy for lead placement techniques described herein.
Figure 5:
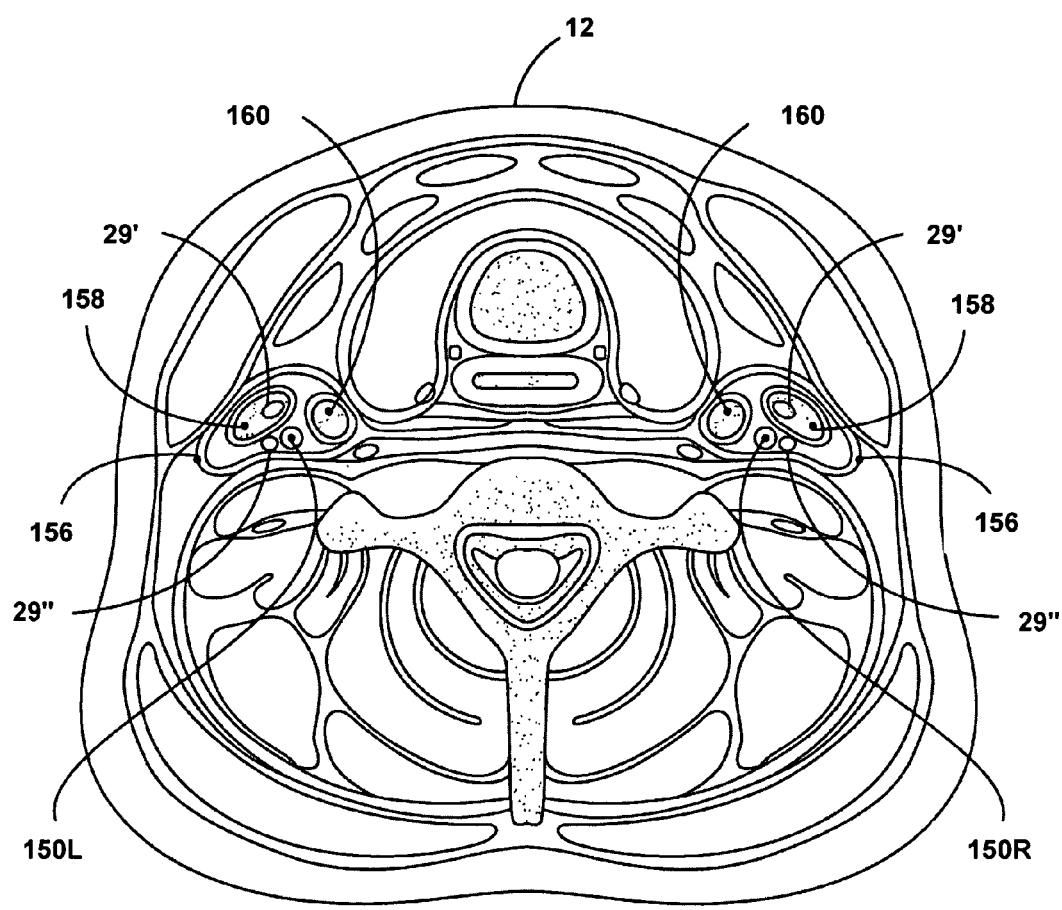

FIGS. 4 and 5 are schematic illustrations depicting relevant anatomy for lead placement techniques described herein. FIG. 4 illustrates vagus nerve 150 including many branches, such as pharyngeal and laryngeal branches 152, cardiac branches 154, as well as the gastric and pancreaticoduodenal branches (not specifically labeled in FIG. 4). The illustration of FIG. 5 is a cross section through the neck of patient 12 that shows carotid sheath 156 in which is contained internal jugular vein 158, carotid artery 160, and left and right vagus nerves 150L and 150R respectively. Vagus nerve 150 originates in the brainstem, runs in the neck through carotid sheath 156 with jugular vein 158 and common carotid artery 160, and then adjacent to the esophagus to the thoracic and abdominal viscera. Vagus nerve 150 provides the primary parasympathetic nerve to the thoracic and most of the abdominal organs. For example, vagus nerve 150 provides parasympathetic innervation to the heart, and stimulation of the nerve has been demonstrated to drive the parasympathetic nervous system and thereby overcome an accelerated sympathetic tone, which may be exhibited by patients suffering from various tachycardia conditions, as well as heart failure. In one such tachycardia application, the efferent fibers of the vagus nerve, such as one or more superior and/or inferior cardiac branches may be electrically stimulated to manage the accelerated arrhythmia. Vagal nerve stimulation may also have afferent effects that result in nerve reflex changes that affect heart rate. In addition to heart innervations, vagus nerve 150 is responsible for such varied tasks as gastrointestinal peristalsis, sweating, as well as muscle movements related to speech. Electrical stimulation of vagus nerve 150 may be useful in treating, not only heart failure and arrhythmia conditions, but also various other conditions including, e.g., depression, epilepsy, and various gastrointestinal conditions. To determine the need for and/or response to nerve tissue stimulation according to methods and systems disclosed herein, ECG, heart rate, blood pressure, blood flow, cardiac output, and/or breathing, for instance, of patient 12 can be sensed. Such patient feedback information can be gleaned from, e.g., clinician observation, as well as employing one of implantable cardiac device (ICD) 17 shown in FIG. 1B or cardiac therapy module 104 shown in FIG. 2. Again, although the techniques disclosed herein are described generally in the context of stimulation of one of the vagus nerves on the vagal nerve trunk in the neck of a human patient, the methods and systems disclosed are also applicable to stimulation and treatment of other nerve tissues that are located in diverse locations including, e.g., baroreceptors, hypoglossal nerves, and nerve plexus and ganglia.

In addition to various biological structures of patient 12, FIG. 5 shows intra and extravascularly placed leads 29' and 29" respectively. Medical lead 29 is used for purposes of describing placement techniques according to this disclosure. In general, lead 29 may correspond to lead 28 shown in FIGS. 1A and 1B above. Intravascular lead 29' is arranged within internal jugular vein 158, while extravascular lead 29" is arranged within carotid sheath 156, adjacent vagus nerve 150. In addition to intra and extravascular leads 29' and 29" shown in FIG. 5, examples according to this disclosure include transvascular placement of lead 29 such that the lead passes from within a blood vessel of patient 12 through a wall of the vessel to terminate adjacent a target nerve tissue stimulation site. For example, lead 29 may be guided proximate a target site intravascularly through internal jugular vein 158 and then pierce a wall of jugular vein 158 to be arranged adjacent vagus nerve 150. Although the examples disclosed herein are generally described in the context of stimulating vagal nerves in the neck of patient 12, lead 29 and electrodes attached thereto may also be arranged for vagal nerve stimulation in, e.g., the thorax, and/or adjacent to the esophagus.

Extravascular lead placement techniques according to this disclosure provide placement of leads for nerve tissue stimulation and/or nerve signal sensing using implantation procedures with reduced invasiveness and without the need to anchor the leads at or very near their distal end. In general, the disclosed techniques include placing a portion of a medical lead having an electrode in an extravascular space within a sheath of tissue within a patient, and adjacent nerve tissue that is also within the sheath of tissue. The lead is anchored offset from the electrode at least partially outside of the sheath.

Figure 6:
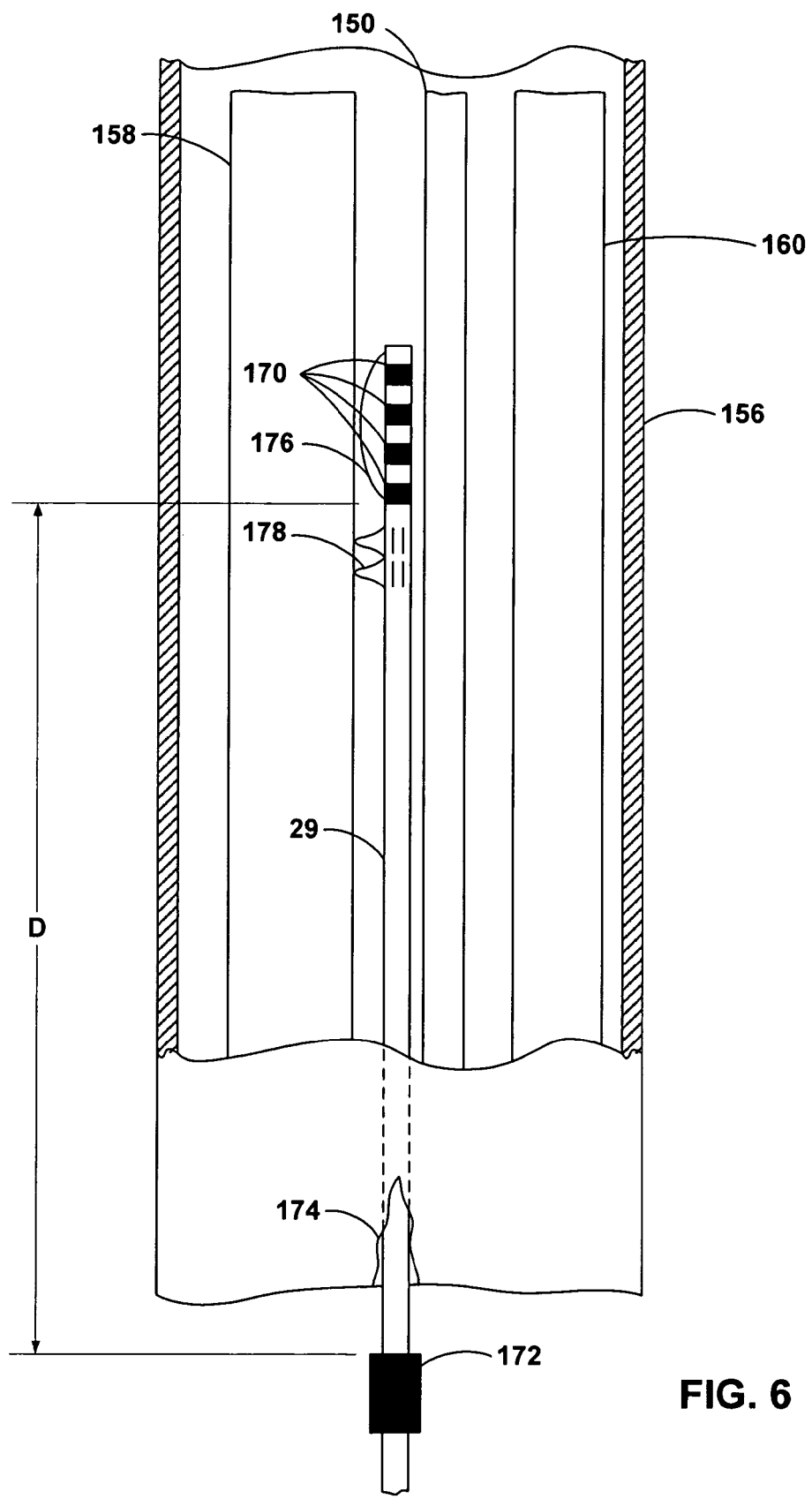
FIG. 6 is a schematic illustration depicting a medical lead placed extravascularly adjacent a vagus nerve.
Figure 7:
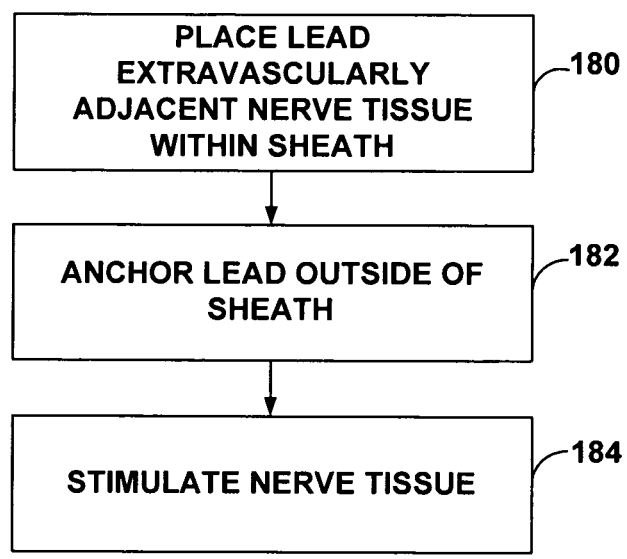
FIG. 7 is a flow chart illustrating an example extravascular lead placement method.

FIGS. 6-8 illustrate examples of extravascular lead placement techniques in the context of vagal nerve stimulation in a human patient. FIG. 6 is a schematic illustration depicting lead 29 extravascularly placed adjacent vagus nerve 150 within carotid sheath 156 in patient 12. After or during placement, lead 29 may be connected to IMD 16 or INS 26 similar to lead 28 shown in FIGS. 1A and 1B respectively. FIG. 7 is a flow chart illustrating an example method of placing lead 29 in accordance with the example of FIG. 6. The example method of FIG. 7 generally includes placing a portion of a medical lead having an electrode electrically connected thereto in an extravascular space adjacent nerve tissue within a sheath of tissue within a patient (180), anchoring the lead offset from the electrode outside of the sheath, (182), and stimulating the nerve tissue (184). One example of the method illustrated in FIG. 7 will be described in the context of the example lead placement shown in FIG. 6.

The arrangement shown in FIG. 6 includes lead 29, electrodes 170, and anchor 172. Electrodes 170 are connected to and arranged toward a distal end of lead 29. The example of FIG. 6 also includes biasing member 176 and deployable lobe member 178 connected to lead 29 to bias and/or stabilize lead 29 and electrodes 170 toward vagus nerve 150. Although the example of FIG. 6 shows four electrodes 170, other examples may include fewer or more electrodes connected to lead 29 and, in some cases, other leads in addition to lead 29. In some examples, electrodes 170 may include multiple types including, e.g., electrode pads on a paddle lead, circular (e.g., ring) electrodes surrounding the body of leads 16, conformable electrodes, segmented electrodes, or any other type of electrodes capable of forming unipolar, bipolar or multipolar electrode configurations for delivering nerve tissue stimulation therapy to patient 12. In some examples including ring electrodes, electrodes 170 may be arranged on lead 29 with part of the rings electrically insulated to limit the spread of the stimulating field so that only a portion of the electrodes and electrical stimulation may be directed at vagus nerve 150.

The distal end of lead 29 to which electrodes 170 are attached is arranged within carotid sheath 156, adjacent vagus nerve 150. Biasing member 176 and deployable lobe member 178 are arranged at the distal end of lead 29 and bias lead 29 toward vagus nerve 150 by exerting a force on surrounding tissue including, e.g., internal jugular vein 158. A proximate end of lead 29 (not shown in FIG. 6) may be connected to IMD 16 (see FIG. 1A). Anchor 172 is connected to lead 29 offset from the distal end of lead 29 outside of carotid sheath 156. Anchor 172 may be any suitable fixation element that stabilizes the placement of lead 29 and electrodes 170 within sheath 156 adjacent vagus nerve 150. For example, anchor 172 may be one of a variety of sutureless fixation elements connected to lead 29 that are configured to engage tissue of patient 12 outside of carotid sheath 156. In one example, one or more tines or barbs may protrude from lead 29 to pierce and thereby attach lead 29 to tissue of patient 12 outside of sheath 156. In addition to or instead of sutureless anchors, anchor 172 may include various fixation elements that engage lead 29 and are configured to be sutured by a clinician to the tissue of patient 12 outside of carotid sheath 156. Additionally, in some examples, anchor 172 may include a sleeve configured to receive lead 29 therethrough and tabs protruding from the sleeve that may passively engage or be sutured to tissue of patient 12. In some examples, such sleeve anchors may be used to seal a tissue access site, such as incision 174 in carotid sheath 156. Anchor 172 is offset from the most proximal of electrodes 172 by a distance D. In some examples, the offset distance D of anchor 172 from the most proximal of electrodes 172 is in the range from and including approximately 1 cm to and including approximately 15 cm. In other examples, the offset distance D may be in the range from and including approximately 1 cm to and including approximately 2 cm.

In practice, a variety of techniques may be employed to extravascularly place lead 29 within carotid sheath 156 adjacent vagus nerve 150. In the example of FIG. 6, the portion of carotid sheath 156 and surrounding tissue of patient 12 shown may be exposed by an incision in the neck of the patient. However, because lead 29 is not anchored at the distal end that is arranged within carotid sheath 156, all of or even a portion of vagus nerve 150 need not be dissected from sheath 156. Instead, lead 29 may be guided through a relatively small incision 174 in carotid sheath 156 to place the distal end of lead 29 including electrodes 170 adjacent vagus nerve 150. Lead 29 may be placed through incision 174 within carotid sheath 156 using a variety of introducer elements including, e.g., a catheter and/or a guide wire to stabilize and guide the placement of lead 29 adjacent vagus nerve 150. Lead 29 may be stiffened within carotid sheath 156 by, e.g., the guide wire or a stylus. Additionally, the distal end of lead 29 including electrodes 170 may be biased toward vagus nerve 150 using biasing member 176. Biasing member 176 may be, e.g. an inflatable or otherwise expandable structure including, e.g. a stent-like member or a balloon as schematically illustrated in FIG. 6. In other examples, biasing member 176 may be static, e.g. protruding tines, or retractable and/or deployable, e.g. one or more elongated splines or lobes that deflect away from lead 29 when placed under tension. For example, in addition to biasing member 176, the example of FIG. 6 includes deployable lobe member 178 including a plurality of deployable lobes that protrude from and are circumferentially distributed about lead 29.

An example of deployable lobe member 178 may be the Attain® StarFix™ fixation element included in the over-the-wire lead Model 4195 developed and sold by Medtronic, Inc. of Minneapolis, Minn. The design of this fixation element allows clinicians to place and stabilize elongated medical electrical leads within patients. The StarFix™ element generally includes a number of deployable lobes that are formed lengthwise on an insulating sheath that surrounds the medical lead by pairs of elongated, parallel cuts or slits. The deployable lobes are formed by the material between the elongated, substantially parallel slits. The spacing between the slits generally defines the width of the deployable lobe formed therebetween. Accordingly, the rigidity of each lobe may be increased or decreased by increasing or decreasing the distance between the parallel slits that define the lobe. The rigidity of the lobes may also be altered by using different types of materials and changing the thickness of the insulating sheath in which the slits are cut to produce the deployable lobes. The StarFix™ lobes are deployed by pushing the insulating sheath on either side of the parallel slits. The pushing action causes the sheath to become compressed, thus causing the extension of the deployable lobes outwardly. As necessary, the lobes can be relaxed to allow for acute repositioning of the lead by withdrawing a coupling member so as to reduce compression on the lobe structure. The StarFix™ lead technology provides reliable fixation of medical leads that can be readily customized to fit a variety of anatomical dimensions. Examples of deployable lobe members for biasing and/or stabilizing lead 29 within carotid sheath 156 include those described in U.S. Patent Publication No. 2004/0176782 A1, to George H. Hanse et al., filed Mar. 3, 2004, titled "METHOD AND APPARATUS FOR FIXATING AN IMPLANTABLE MEDICAL DEVICE," the entire content of which is incorporated herein by reference.

The placement of lead 29 adjacent vagus nerve 150 may be stabilized by anchor 172. As explained above, anchor 172 may be any suitable fixation element that stabilizes the placement of lead 29 and electrodes 170 within sheath 156 adjacent vagus nerve 150. In one example, anchor 172 includes one or more tines protruding from lead 29 offset from the most proximate of electrodes 170 by a distance D. The tines of anchor 172 may be angled with respect to lead 29 and flexible such that as lead 29 is guided forward through tissue of patient 12 the tines lay down against an exterior surface of the lead and do not engage the tissue of the patient. After placement, lead 29 may be backed slightly out through the tissue of patient 12 to cause the tines of anchor 172 to pull away from the lead and catch and pierce the tissue of patient 12, thereby connecting lead 29 to the tissue.

Figure 8A:
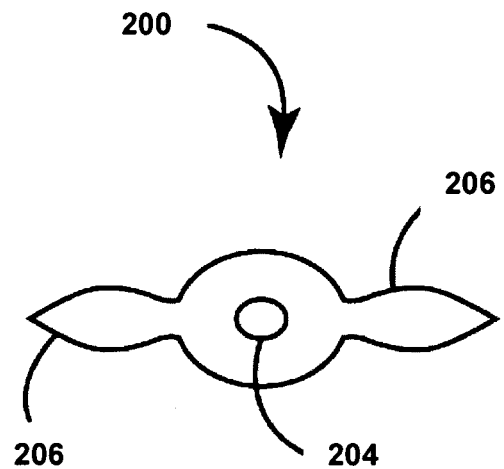
FIGS. 8A and 8B show two example sleeve anchors for use with extravascular lead placement techniques according to this disclosure.
Figure 8B:
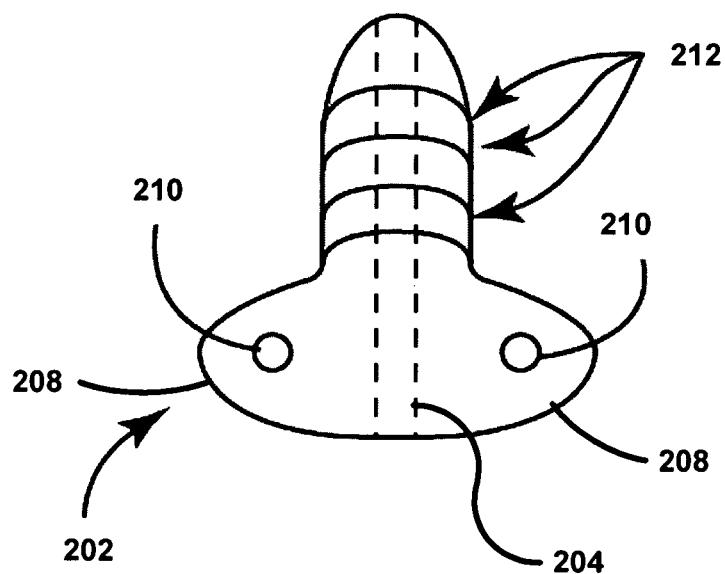

In other examples, anchor 172 may include a sleeve anchor configured to receive lead 29 therethrough and passively engage or be sutured to tissue of patient 12. FIGS. 8A-8B show two example sleeve anchors 200 and 202 respectively. Both anchors 200 and 202 have interior bore 204 that is sized to receive lead 29 therethrough. Anchors 200 and 202 also include tabs 206 and 208 respectively protruding away from bore 204. Tabs 206 of anchor 200 are configured to passively engage tissue of patient 12 to substantially fix the anchor and thereby stabilize the placement of lead 29. Tabs 208 of anchor 202, on the other hand, includes suture-receiving apertures 210 that may receive sutures to attach anchor 202 to tissue of patient 12 and thereby stabilize the placement of lead 29. Anchor 202 also includes ribs 212, which may be adapted to inhibit longitudinal movement of anchor 202 and/or lead 29 with respect to tissue of patient 12 to further stabilize the placement of lead 29. In some examples, sleeve anchors 200 and 202 may be used to seal a tissue access site, such as incision 174 in carotid sheath 156.

Figure 8C:
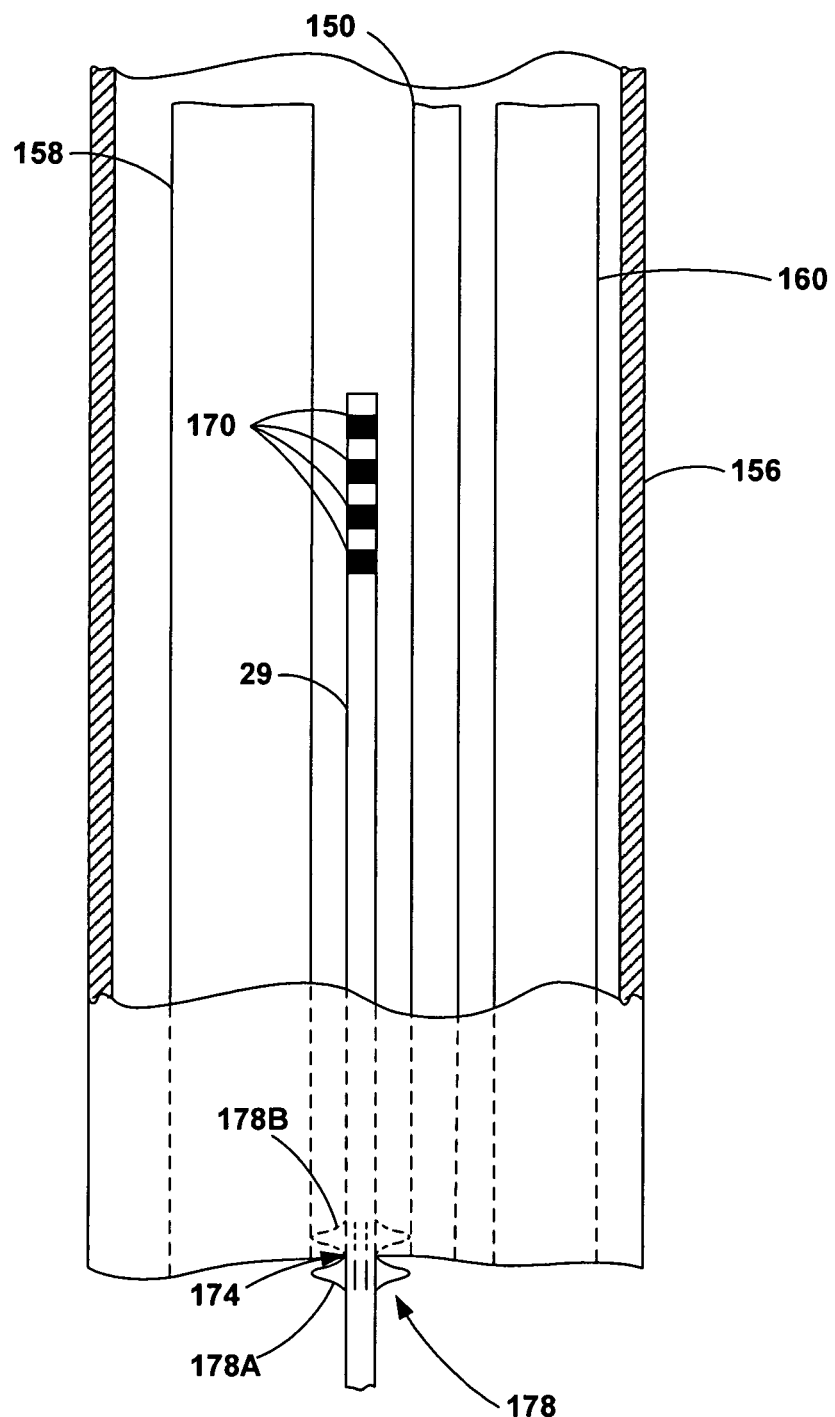
FIG. 8C shows deployable lobe member for use with extravascular lead placement techniques according to this disclosure.

In addition to the above described examples, anchor 172 may include deployable lobes that are arranged to deploy on either side of incision 174 in carotid sheath 156 to stabilize the placement of lead 29 adjacent vagus nerve 150. FIG. 8C shows deployable lobe member 178 arranged at incision 174 in carotid sheath 156 to stabilize placement of lead 29. As with the example arrangement shown in FIG. 6, deployable lobe member 178 in FIG. 8C includes a plurality of deployable lobes that protrude from and are circumferentially distributed about lead 29. In FIG. 8C, however, lobe member 178 is arranged with respect to incision 174 such that the incision in carotid sheath 156 lies between two sets of deployable lobes 178A, 178B of deployable lobe member 178. Deployable lobe set 178A lies adjacent incision 174 outside of carotid sheath 156, while set 178B lies inside the sheath. Upon deployment of lobe sets 178A and 178B on either side of incision 174, deployable lobe member 178 stabilizes the placement of lead 29 and electrodes 170 within sheath 156 adjacent vagus nerve 150. As with the example of FIG. 6, an example of deployable lobe member 178 arranged as in the example of FIG. 8C may be the Attain® StarFix™ fixation element developed and sold by Medtronic, Inc. of Minneapolis, Minn.

A portion of lead 29 extending from anchor 172 in the examples of FIGS. 6-8C may be guided to connect with IMD 16. In one example, lead 29 may be guided intravascularly to an implantation location of IMD 16 within patient 12. In other examples, lead 29 may be tunneled through tissue of patient 12 to be connected to IMD 16. Although the example of FIGS. 6 and 7 is described with reference to implanted medical device 16 arranged within patient 12, examples according to this disclosure also include lead 29 connected transcutaneously to an external medical device that is configured to deliver electrical stimulation to the target nerve tissue, e.g., vagus nerve 150. After lead 29 is placed adjacent vagus nerve 150 and connected to IMD 16, IMD 16, either automatically or as partially or completely commanded by programmer 24, may deliver electrical stimulation therapy to and/or receive sensor feedback from vagus nerve 150 through electrodes 170.

Intravascular lead placement proximate target nerve tissue within a patient generally requires minimally invasive surgical techniques because the medical leads used to deliver therapy are guided to the site through a blood vessel, e.g., a vein or artery that may be readily accessible, e.g., transcutaneously through a small incision. Intravascular lead placement techniques disclosed herein further facilitate placing the distal end of the lead in close proximity of the target nerve tissue, which can be arranged in different circumferential positions with respect to the blood vessel in which the lead is located.

Intravascular techniques described in greater detail below may include structures and methods for deployment of one or more medical leads at a first location, testing stimulation at the first location, and, depending on the efficacy of the stimulation provided by electrodes on the leads at the first location, redeploying the leads to a second location. In one example, lead placement is improved by locating target nerve tissue with a sensor including, e.g., an IVUS imaging system system and/or measuring the efficacy of test electrical stimulation pulses from an electrode on the lead through a blood vessel adjacent the target tissue. After a placement location is determined, one or more leads including one or more electrodes may be deployed into the vessel and anchored to a vessel wall near the target nerve tissue.

Figure 9:
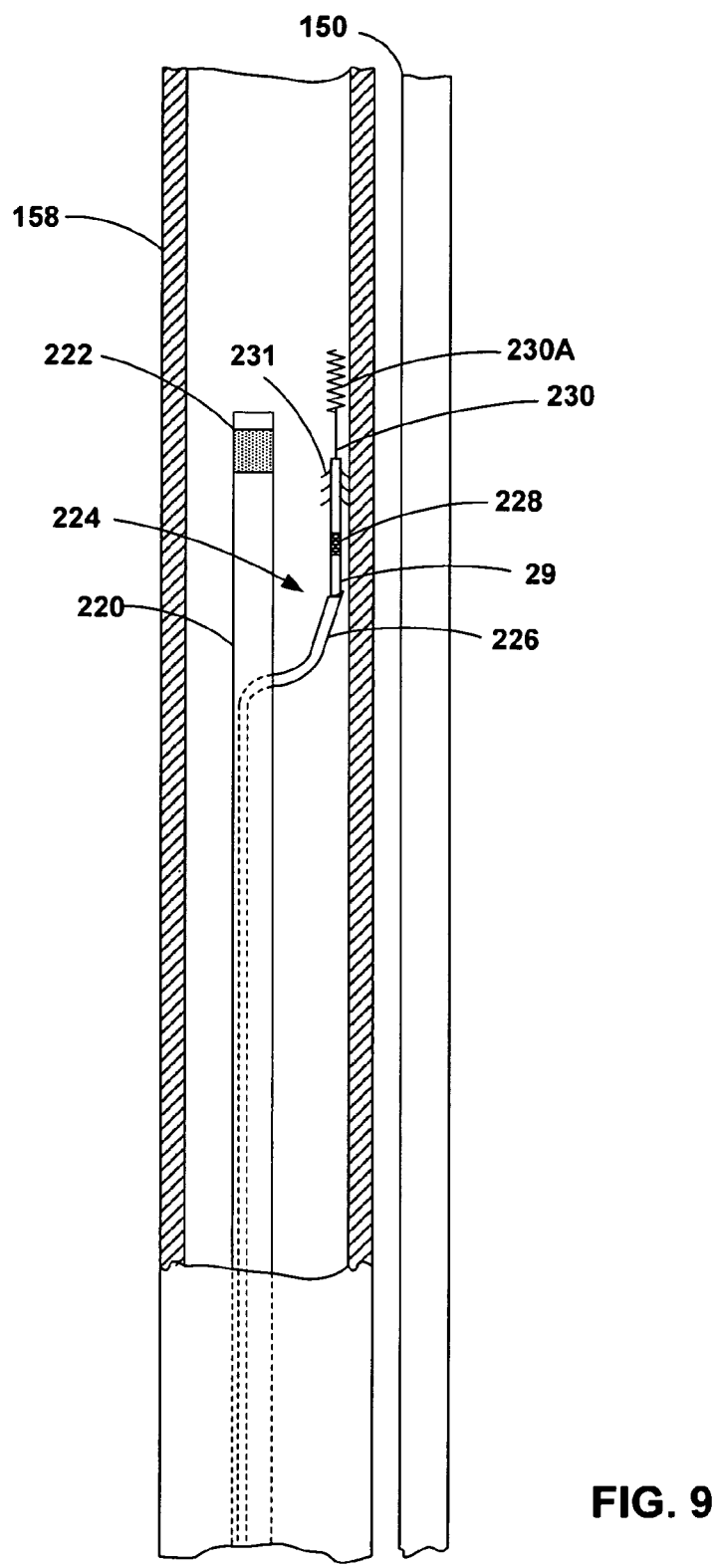
FIG. 9 is a schematic illustration depicting a medical lead placed intravascularly within the internal jugular vein adjacent a vagus nerve.
Figure 10:
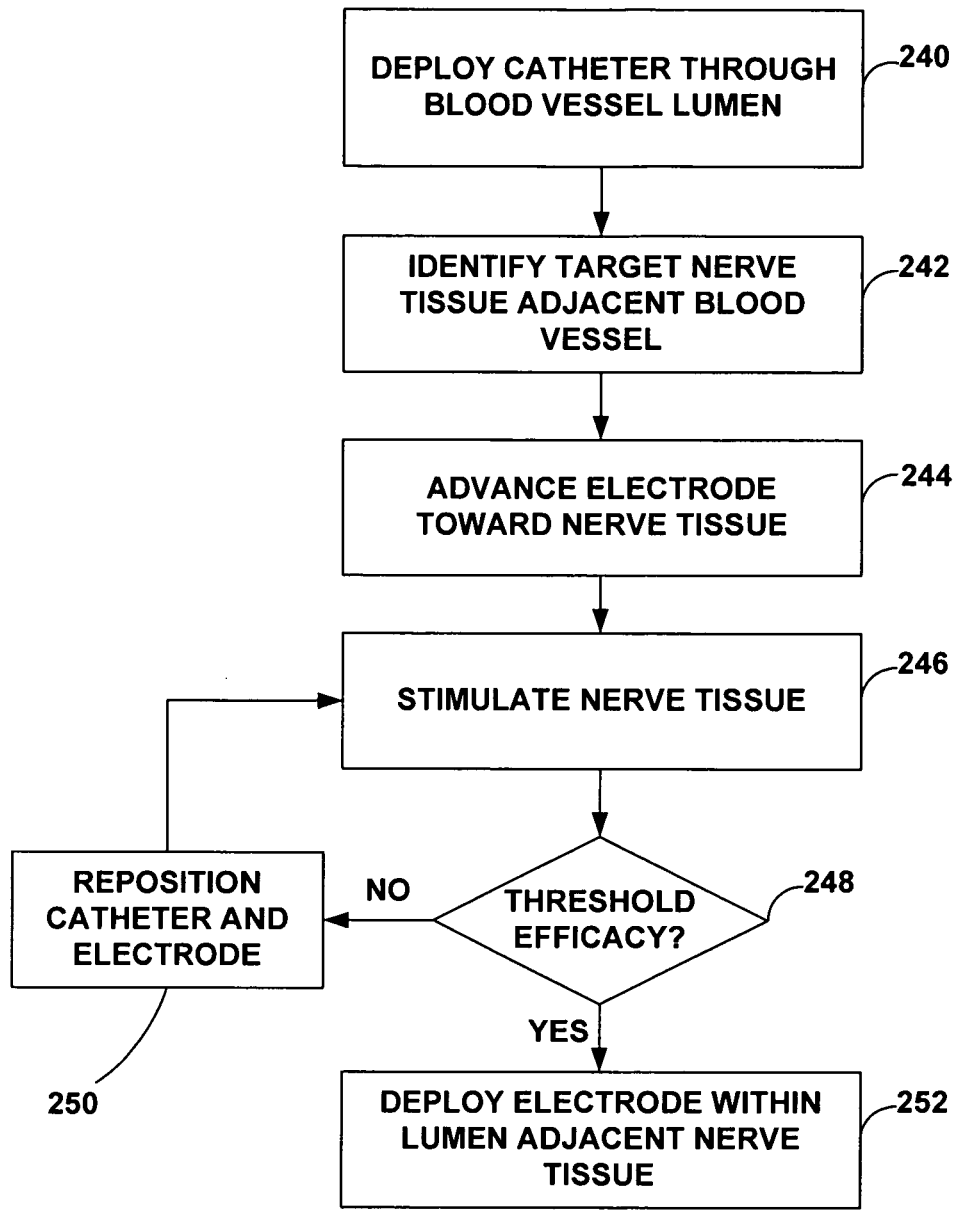
FIG. 10 is a flow chart illustrating an example intravascular lead placement method.

FIGS. 9 and 10 illustrate examples of intravascular lead placement techniques in the context of vagal nerve stimulation in a human patient. FIG. 9 is a schematic illustration depicting lead 29 intravascularly placed adjacent vagus nerve 150 within internal jugular vein 158 in patient 12. After or during placement, lead 29 may be connected to IMD 16 or INS 26 similar to lead 28 shown in FIGS. 1A and 1B respectively. FIG. 10 is a flow chart illustrating an example method of placing lead 29 in accordance with the example of FIG. 9. The example method of FIG. 10 includes deploying a delivery catheter through a lumen of a blood vessel to a target nerve tissue site (240), identifying a location of the nerve tissue with respect to the blood vessel with one or more sensors connected to the delivery catheter (242), advancing an electrical stimulation electrode from the catheter within the blood vessel lumen toward the nerve tissue (244), energizing the electrode to deliver electrical stimulation from within the blood vessel lumen to the nerve tissue (246), comparing the efficacy of the nerve tissue stimulation to a threshold efficacy (248), and repositioning the delivery catheter and the electrode within the blood vessel lumen if the efficacy of the nerve tissue stimulation does not meet or exceed the threshold efficacy (250), or chronically deploying the electrode within the blood vessel lumen adjacent the nerve tissue if the efficacy of the nerve tissue stimulation meets or exceeds the threshold efficacy (252). One example of the method illustrated in FIG. 10 will be described in the context of the example lead placement structure shown in FIG. 9.

The arrangement shown in FIG. 9 includes delivery catheter 220, sensor 222, and deployment member 224. Sensor 222 is connected to catheter 220 toward a distal end thereof. Deployment member 224 is extendable and retractable from catheter 220. Sensor 222 is arranged between the distal end of catheter 220 and the location along catheter 220 from which deployment member 224 is extendable and retractable. Deployment member 224 includes tubular member 226, lead 29, electrode 228, and guidewire 230. Guidewire 230 includes anchor portion 230A at a distal end thereof. Electrode 228 is connected toward a distal end of lead 29. Lead 29 and guidewire 230 are received within and advanceable through a lumen of tubular member 226. Lead 29 is advanceable along guidewire 230.

In FIG. 9, catheter 220 is deployed through internal jugular vein 158 of patient 12 to a target nerve tissue stimulation site. In other examples, catheter 220 may be deployed in other blood vessels within patient 12 including, e.g., carotid artery 160, or the superior or inferior vena cava. Catheter 220 can be any suitable delivery catheter capable of intravenous delivery within patient 12 and adapted to accommodate sensor 222 and deployment member 224. Sensor 222 is connected to the distal end of catheter 220 and is configured to detect the relative position of vagus nerve 150 outside of jugular vein 158, as well as electrode 228 on lead 29 within the lumen of vein 158. Sensor 222, in general, may be any suitable imaging or guidance system including, e.g., a fiberoptic endoscope, ultrasound imaging system, or any other on-board imaging system capable of assisting in the positioning of catheter 220 and electrode 228 within jugular vein 158 relative to vagus nerve 150 by providing an image of the area adjacent the location of sensor 222 on catheter 220. In some examples, sensor 222 could be an array of receivers in relationship to a transmitter that provide an image of surrounding tissue and structures including vagus nerve 150 and electrode 228. In other examples, sensor 222 may be configured to send or receive signals to or from any of a series of known signal generators including sonic, electromagnetic, light or radiation signals. In still other examples, sensor 222 may be an optical oxygen content sensor that may be used to ensure that lead 29 and electrode 228 are not directed toward, e.g., carotid artery 160 during lead placement. In some examples, sensor 222 may be employed in conjunction with one or more opaque markers viewable with fluoroscopic techniques or with an irrigated lumen that dispenses contrast media to assist in imaging the relative positions of vagus nerve 150 and electrode 228 on lead 29 within the lumen of jugular vein 158.

After the clinician identifies the location of vagus nerve 150 with respect to jugular vein 158 based on the output of sensor 222, the clinician may advance deployment member 224 including electrode 228 toward the wall of the lumen of vein 158 adjacent the nerve. Deployment member 224, in general, is extendable and retractable from catheter 220 from, e.g., an aperture formed in a sidewall thereof. Deployment member 224 includes tubular member 226, lead 29, electrode 228, and guidewire 230. Tubular member 226 may be any structure including at least one lumen through which various electrode deployment structures including, e.g., lead 29 and guidewire 230 may be advanced to place an electrode within vein 158 adjacent vagus nerve 150. In the example of FIG. 9, tubular member 226 may be a needle with a lumen in which lead 29 and guidewire 230 are received and through which the same are advanceable. Electrode 228 is connected to lead 29, which is advanceable along guidewire 230.

With the aid of sensor 222, the clinician advances deployment member 224 from catheter 220 toward vagus nerve 150. Lead 29, to which electrode 228 is connected, and guidewire 230 may be advanced through a lumen of deployment member 224 to position electrode 228 within vein 158 adjacent vagus nerve 150. Guidewire 230 includes anchor portion 230A at a distal end thereof that is configured to temporarily anchor deployment member 224, lead 29 and electrode 228, and guidewire 230 to the wall of the lumen of vein 158. In the example of FIG. 9, anchor portion 230A of guidewire 230 is formed in a spiral that is configured to be twisted into the lumen wall. Anchor portion 230A can be freed from the vessel wall by either untwisting guidewire 230, or in the case that guidewire 230 is sufficiently flexible, pulling the wire away from the spiraling anchor portion 230A to effectively unwind and release the anchor from the wall of jugular vein 158. In addition to anchor portion 230A of guidewire 230, lead 29 includes barbs 231 that are configured to engage tissue of jugular vein 158 to anchor lead 29 and electrode 228 to the wall of the vein after guidewire 230 has been retracted. In other examples, lead 29 may be anchored to the wall of vein 158 with different structures including, e.g., a helical coil or other spiral coil shapes, C-shaped members, harpoon-like structures, hooks, expandable or serrated members, and the like. In FIG. 9, deployment member 224 and electrode 228 on lead 29 are advanced such that at least lead 29 lies in the sensory field of sensor 222.

Figure 11:
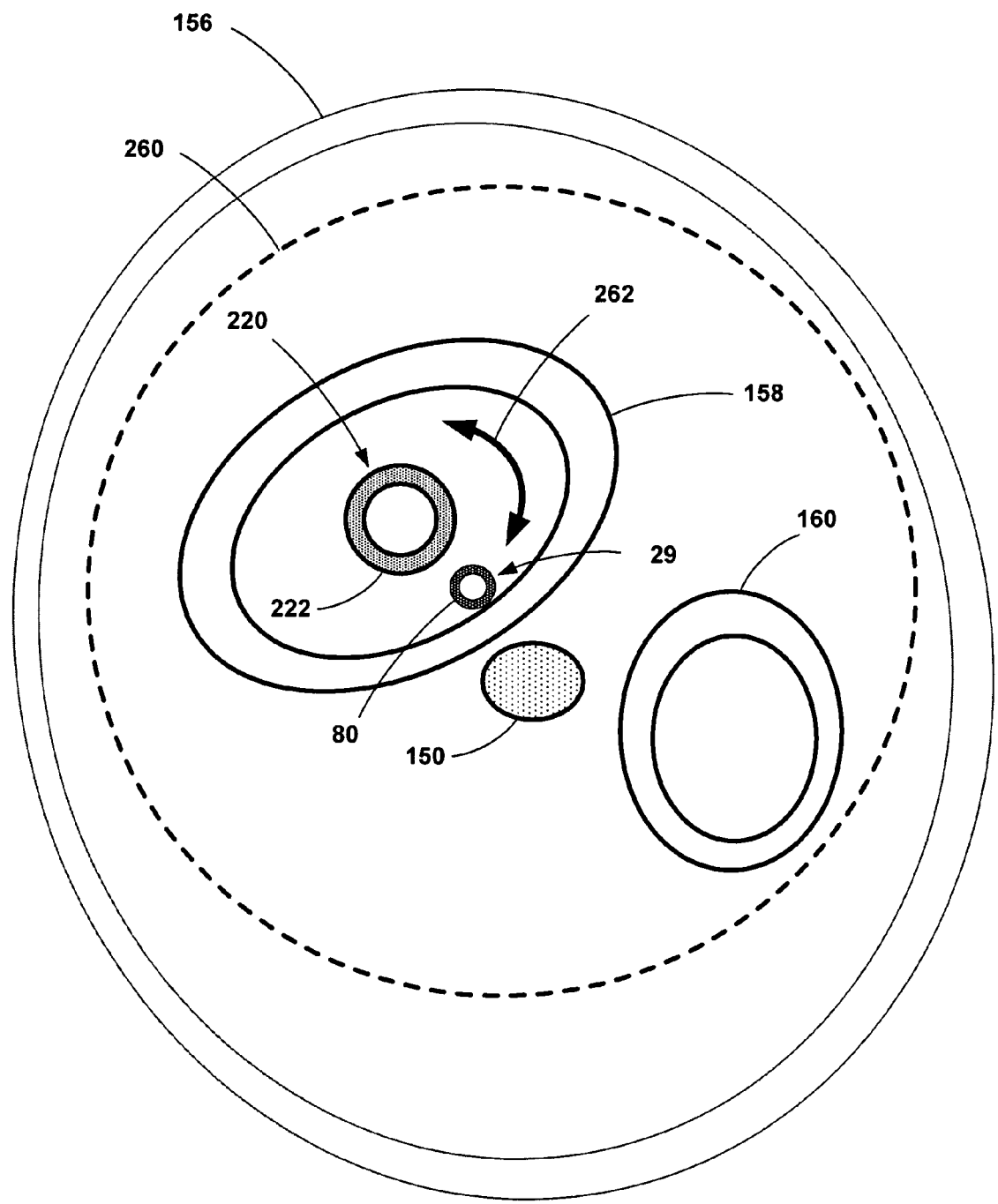
FIG. 11 is a schematic illustration of a two dimensional ultrasonic image generated by a sensor used in conjunction with the intravascular lead placement arrangement shown in FIG. 9.

In one example, sensor 222 is an intravenous ultrasound ("IVUS") imaging system that is adapted to radiate ultrasonic waves out from sensor 222 to generate a two dimensional image of the tissue and structures surrounding catheter 220 and sensor 222. FIG. 11 is a schematic illustration of an example two dimensional ultrasonic image generated by a device coupled to sensor 222 as arranged with catheter 220, lead 29 and electrode 228 of FIG. 9 located within the jugular vein 158. When activated, sensor 222 produces an imaging field 260 from ultrasonic waves produced by and radiating radially from sensor 222. The size of imaging field 260 may vary depending on the particular configuration and capabilities of sensor 222. The tissues and other structures caught within imaging field 260 of sensor 222 may be distinguished from one another and the relative positioning of the different structures may be discerned. In the example of FIG. 11, vagus nerve 150, jugular vein 158, and carotid artery 160 are located within imaging field 260, while carotid sheath 156 shown in shadow lines is not within the sensing range of sensor 222. By distinguishing different structures and displaying relative positions, sensor 222 may be used to facilitate positioning catheter 220 and electrode 228 on lead 29 within jugular vein 158 in a desired location relative to vagus nerve 150 by, e.g., rotating the catheter and electrode within the blood vessel in the directions indicated by arrow 262 in FIG. 11.

Having deployed catheter 220, detected the location of vagus nerve 150 relative to jugular vein 158, and advanced electrode 228 toward vagus nerve 150, electrical stimulation may be delivered to vagus nerve 150 through the wall of the lumen of vein 158 via electrode 228. During test stimulation of vagus nerve 150, a portion of lead 29 extending away from a distal end toward which electrode 228 is arranged may be connected, e.g., transcutaneously to an external neurostimulation device that is configured to deliver electrical stimulation to the target nerve tissue, e.g., vagus nerve 150 while lead 29 and electrode 228 are being positioned relative thereto within vein 158. After lead 29 is connected to the neurostimulator, the device, either automatically or as partially or completely commanded by a programmer, such as programmer 24, may deliver electrical stimulation therapy to and/or receive sensor feedback from vagus nerve 150 through electrode 228.

In the example of FIGS. 9 and 10, as well as other examples disclosed herein, the efficacy of the electrical stimulation delivered by electrode 228 to vagus nerve 150 may be compared to a threshold efficacy to determine whether or not electrode 228 is satisfactorily positioned with respect to nerve 150. Efficacy refers, in general, to a combination of complete or partial alleviation of symptoms alone, or in combination with a degree of undesirable side effects. Efficacy may be measured, in general, by verbal feedback from patient 12, clinician observation of various conditions of patient 12, or sensory feedback from one or more devices including, e.g., ICD 17 shown in FIG. 1A or cardiac therapy module 104 shown in FIG. 4. Various physiological signals may be observed to measure the efficacy of the test stimulation, and thereby the need to reposition lead 29 relative vagus nerve 150. For example, to determine the response to stimulation of vagus nerve 150, ECG, heart rate, blood pressure, blood flow, cardiac output, and/or breathing, of patient 12 can be sensed or observed. These and other physiological signals may be detected in a variety of ways including sensing the signals using sense electrodes, pressure sensors, ultrasound sensors, motion sensors or other devices. In other examples, physiological reactions of patient 12 may be observed or measured by, e.g., a clinician. In one example, efficacy may be measured by a sensor including, e.g., an accelerometer that determines if stimulation of the neck muscles or phrenic nerve of patient 12 is occurring with or instead of stimulation of vagus nerve 150. In another example, a pressure sensor arranged coincident with or connected to lead 29 may measure blood pressure by detecting the pressure within jugular vein 158. A pressure sensor, or other type of physiological feedback sensor, may also, in some examples, be connected to catheter 220 to measure, e.g., blood pressure within vein 158.

In the event the nerve tissue stimulation meets or exceeds the threshold efficacy, lead 29 and electrode 228 may be chronically deployed within jugular vein 158 adjacent vagus nerve 150. On the other hand, if the nerve stimulation delivered by electrode 228 does not provide the threshold level of efficacy in relieving the symptoms of patient 12, catheter 220 and electrode 228 may be repositioned within jugular vein 158 to improve the location of the components, in particular electrode 228 with respect to vagus nerve 150. Generally speaking, catheter 220 and electrode 228 may be repositioned by rotating catheter 220 within jugular vein 158 in the manner described with reference to FIG. 11 and with the assistance of, e.g., ultrasound imaging provided by sensor 222. In some examples, guidewire 230 including anchor portion 230A may be retracted along with lead 29 and electrode 228 into deployment member 224 before repositioning catheter 220 and then redeployed after the catheter has be relocated. After repositioning catheter 220 and electrode 228, the process of stimulating vagus nerve 150 and comparing the efficacy of the nerve stimulation to a threshold efficacy may be repeated until the arrangement of electrode 228 with respect to vagus nerve 150 delivers electrical stimulation therapy that meets or exceeds the threshold efficacy level.

After determining a placement location that delivers satisfactory treatment efficacy, lead 29 and electrode 228 may be chronically deployed within jugular vein 158 adjacent vagus nerve 150. After chronic deployment of lead 29 and electrode 228, a portion of lead 29 extending away from a distal end toward which electrode 228 is arranged may be guided to connect with, e.g., IMD 16. In one example, lead 29 may be guided intravascularly to an implantation location of IMD 16 within patient 12. In other examples, lead 29 may be tunneled through tissue of patient 12 to be connected to IMD 16. After lead 29 is placed adjacent vagus nerve 150 and connected to IMD 16, IMD 16, either automatically or as partially or completely commanded by programmer 24, may deliver electrical stimulation therapy to and/or receive sensor feedback from vagus nerve 150 through electrode 228.

Figure 12A:
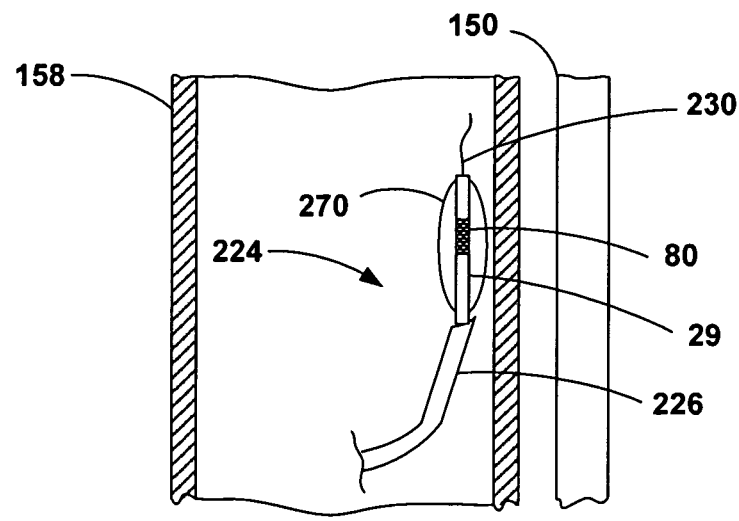
FIGS. 12A and 12B show several example deployment members for use in intravascular lead placement methods and systems according to this disclosure.
Figure 12B:
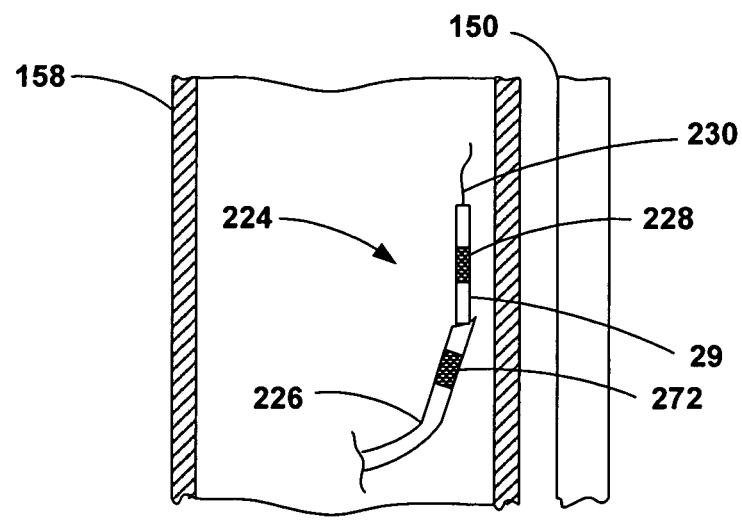

FIGS. 12A and 12B show alternative examples of deployment member 224 for use in methods and systems according to this disclosure. In general, FIGS. 12A and 12B show different arrangements and combinations of anchoring members and electrodes with respect to tubular member 226, lead 29, and guidewire 230 of deployment member 224. In the interest of simplicity, catheter 220 has been omitted from the illustrations of FIGS. 12A and 12B. In FIG. 12A, deployment member 224 is arranged within jugular vein 158 adjacent vagus nerve 150 and includes tubular member 226, lead 29, electrode 228, guidewire 230, and expandable member 270. In some examples, expandable member 270 may provide additional stabilization or biasing of lead 29 or other components of deployment member 224 within jugular vein 158. For example, expandable member 270 may push against catheter 220 (not shown in FIG. 12A) to bias lead 29 and electrode 228 toward the wall of the lumen of vein 158. In another example, expandable member 270 may further stabilize the placement of lead 29 and electrode 228 by expanding to apply force on the lumen wall and catheter 220. The expandable member 270 may, in some examples, be a balloon catheter including, e.g., an angioplasty catheter. In other examples, expandable member 270 may be a stent or deployable spline or lobe.

FIG. 12B shows deployment member 224 with additional electrode 272 connected to tubular member 226. In FIG. 12B, deployment member 224 is arranged within jugular vein 158 adjacent vagus nerve 150 and includes tubular member 226, lead 29, electrode 228, guidewire 230, and electrode 272. Although intravascular placement examples of lead 29 have been described herein with reference to a single electrode 228 for simplicity, in practice, lead 29 will commonly include a plurality of electrodes that may be employed in different anode and cathode combinations to stimulate vagus nerve 150 as, e.g., described with reference to electrodes 80-83 in FIG. 2. Additionally and as illustrated in FIG. 12B, deployment member 224 may include electrodes in addition to lead electrode 228 arranged in different locations and/or connected to different components. Electrode 272 is connected to tubular member 226 in the example of FIG. 12B. In some examples, tubular member 226 and electrode 272 may be advanced toward vagus nerve 150 prior to chronically deploying lead 29 and electrode 228. In such examples, electrode 272 may be used to deliver test stimulation pulses to vagus nerve 150 to determine the efficacy of the placement of deployment member 224 within jugular vein 158 with respect to vagus nerve 150. After determining a position of deployment member that provides a threshold efficacy in stimulating vagus nerve 150, lead 29 and guidewire 230 may be advanced through tubular member 226 and lead 29 and electrode 228 may be chronically deployed along the wall of the lumen of jugular vein 158 adjacent vagus nerve 150.

Figure 13:
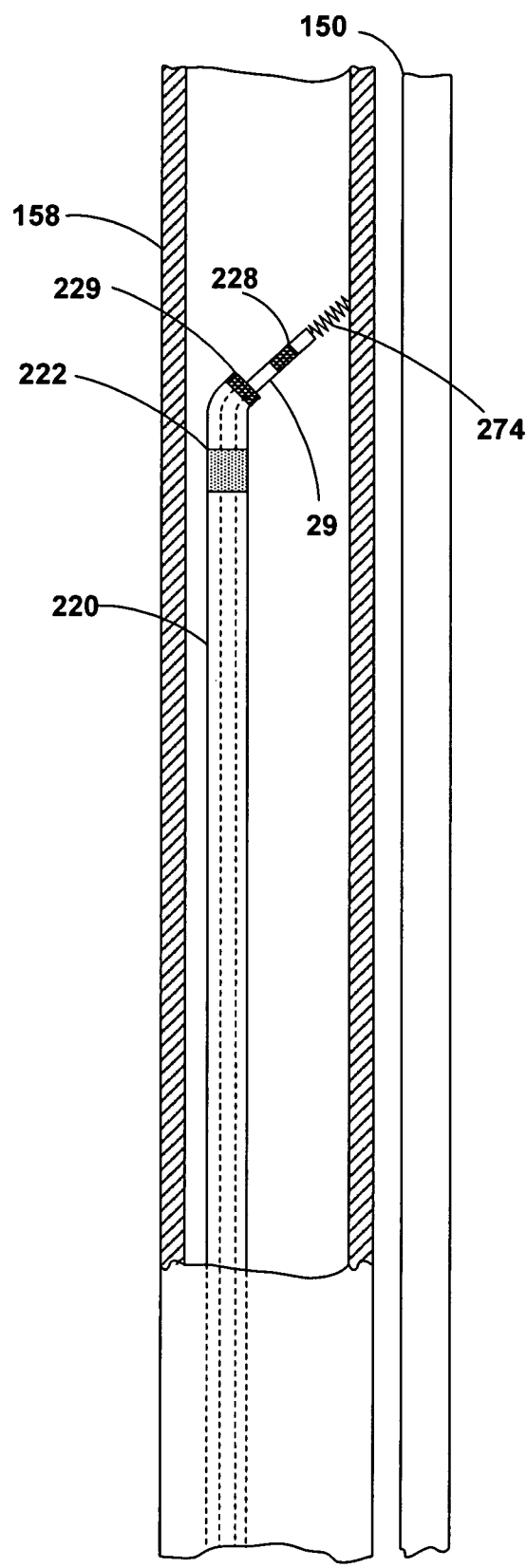
FIG. 13 is a schematic illustration depicting a medical lead placed intravascularly and actively fixed to a wall of the internal jugular vein adjacent a vagus nerve.

In addition to placing lead 29 and electrode 228 intravascularly using deployment member 224 as shown in the examples of FIGS. 9, 11, 12A and 12B, lead 29 and electrode 228 may be advanced from a distal tip of catheter 220 to be actively fixed to the wall of jugular vein 158 as shown in FIG. 13. The arrangement shown in FIG. 13 includes delivery catheter 220, sensor 222, lead 29, electrodes 228 and 229, and active fixation member 274. Sensor 222 and electrode 229 are connected to catheter 220 toward a distal end thereof. Electrode 228 is connected toward a distal end of lead 29. Lead 29 and electrode 228 are received within and advanceable through a lumen of catheter 220 and out of the tip of the catheter to place electrode 228 within vein 158 adjacent vagus nerve 150. Although not shown in FIG. 13, lead 29 may be advanced along and guided by a guide member including, e.g., a guidewire or a stylus.

In FIG. 13, catheter 220 is deployed through internal jugular vein 158 of patient 12 to a target nerve tissue stimulation site. In other examples, catheter 220 may be deployed in other blood vessels within patient 12 including, e.g., carotid artery 160, or the superior or inferior vena cava. Catheter 220 can be any suitable delivery catheter capable of intravenous delivery within patient 12 and adapted to accommodate sensor 222, electrode 229, and lead 29. In some examples, catheter 220 may be flexible or curved to direct the tip of the catheter laterally toward the wall of jugular vein 158. Sensor 222 is connected to the distal end of catheter 220 and is configured to detect the relative position of vagus nerve 150 outside of jugular vein 158. Sensor 222, in general, may be any suitable imaging or guidance system including, e.g., a fiberoptic endoscope, ultrasound imaging system, or any other on-board guidance or imaging system capable of assisting in the positioning of catheter 220 within jugular vein 158 relative to vagus nerve 150 by providing an image of the area adjacent the location of sensor 222 on catheter 220.

Electrode 229 is also connected to a distal end of catheter 220 and may be advanced toward the wall of the lumen of jugular vein 158 to deliver test stimulation pulses to vagus nerve 150 through the wall of vein 158. Electrode 229 may therefore be employed in addition to or in lieu of sensor 222 to detect the relative position of vagus nerve 150 outside of jugular vein 158. During test stimulation of vagus nerve 150, electrode 229 may be connected to a conductor connected, e.g., transcutaneously to an external neurostimulation device that is configured to deliver electrical stimulation to the target nerve tissue, e.g., vagus nerve 150. After electrode 229 is connected to the neurostimulator, the device, either automatically or as partially or completely commanded by a programmer, such as programmer 24, may deliver electrical stimulation therapy to and/or receive sensor feedback from vagus nerve 150.

In the example of FIG. 13, as well as other examples disclosed herein, the efficacy of the electrical stimulation delivered by electrode 229 to vagus nerve 150 may be compared to a threshold efficacy to determine whether or not electrode 229, and thereby catheter 220 is satisfactorily positioned with respect to nerve 150. Efficacy may be measured, in general, by verbal feedback from patient 12, clinician observation of various conditions of patient 12, or sensory feedback from one or more devices including, e.g., ICD 17 shown in FIG. 1A or cardiac therapy module 104 shown in FIG. 4. Various physiological signals may be observed to measure the efficacy of the test stimulation, and thereby the need to reposition catheter 220 and electrode 229 relative vagus nerve 150. For example, to determine the response to stimulation of vagus nerve 150, ECG, heart rate, blood pressure, blood flow, cardiac output, and/or breathing, of patient 12 can be sensed or observed. These and other physiological signals may be detected in a variety of ways including sensing the signals using sense electrodes, pressure sensors, ultrasound sensors, motion sensors or other devices. In other examples, physiological reactions of patient 12 may be observed or measured by, e.g., a clinician. In one example, efficacy may be measured by a sensor including, e.g., an accelerometer that determines if stimulation of the neck muscles or phrenic nerve of patient 12 is occurring with or instead of stimulation of vagus nerve 150. In another example, a pressure sensor arranged coincident with or connected to catheter 220 may measure blood pressure by detecting the pressure within jugular vein 158.

In the event the nerve tissue stimulation meets or exceeds the threshold efficacy, lead 29 and electrode 228 may be chronically deployed by advancing the lead from the tip of catheter 220 within jugular vein 158 toward vagus nerve 150. On the other hand, if the nerve stimulation delivered by electrode 229 does not provide the threshold level of efficacy in relieving the symptoms of patient 12, catheter 220 and electrode 229 may be repositioned within jugular vein 158 to improve location with respect to vagus nerve 150. Generally speaking, catheter 220 and electrode 229 may be repositioned by rotating catheter 220 within jugular vein 158 to different incremental positions until an acceptable position for catheter 220 relative to vagus nerve 150 is determined. After repositioning catheter 220 and electrode 229, the process of stimulating vagus nerve 150 and comparing the efficacy of the nerve stimulation to a threshold efficacy may be repeated until the arrangement of catheter 220 with respect to vagus nerve 150 delivers electrical stimulation therapy that meets or exceeds the threshold efficacy level.

Once catheter 220 is positioned within jugular vein 158 such that electrode 229 delivers stimulation that meets or exceeds the threshold efficacy, lead 29 and electrode 228 may be advanced through a lumen of catheter 220 and out of the tip of the catheter to actively fix lead 29 and electrode 228 to the wall of vein 158 adjacent vagus nerve 150. In FIG. 13, catheter 220 is curved to direct the tip of the catheter laterally toward the wall of jugular vein 158. Connected to a distal end of lead 29 is active fixation member 274, which, in the example of FIG. 13 is a helical coil that is configured to be twisted into the wall of jugular vein 158.

In practice, lead 29, electrode 228, and fixation member 274 may be advanced laterally from the tip of catheter 220 toward the wall of jugular vein 158 adjacent vagus nerve 150. In some examples, lead 29 may be directed toward the wall of vein 158 along a trajectory that is approximately perpendicular to the wall. Active fixation member 274 engages the wall of the lumen of jugular vein 158 by, e.g., twisting lead 29 to screw the helical fixation member into the wall. After actively fixing lead 29 and electrode 228 to the wall of vein 158 adjacent vagus nerve 150, catheter 220 may be removed, after which lead 29 and electrode 228 will lay down along and approximately tangential to the wall of vein 158.

In some examples, active fixation member 274 may be electrically active such that it acts as an electrode in addition to or in lieu of electrode 228. Fixation member 274 may have a variety of lengths and helical pitches. In some examples, fixation member 274 may have a length in the range from and including approximately 0.5 millimeters to and including approximately 2.5 millimeters. In other examples, fixation member 274 may have a length in the range from and including approximately 1 millimeters to and including approximately 2 millimeters. The pitch of the helical coil of active fixation member 274 may also vary in different examples according to this disclosure. In general, in examples in which fixation member 274 is electrically active, it may be desirable to increase the pitch to increase the amount of surface area engaging tissue of the wall of jugular vein 158. In some examples, fixation member 274 may have a helical pitch in the range from and including approximately 0.5842 millimeters to and including approximately 1.016 millimeters.

Figure 14A:
FIGS. 14A-14J are elevation front views of example anchors that may be used alone or in combination to anchor or bias a medical lead and/or electrode placed in accordance with examples disclosed herein.
Figure 14B:
Figure 14C:
Figure 14D:
Figure 14E:
Figure 14F:
Figure 14G:
Figure 14H:
Figure 14I:
Figure 14J:
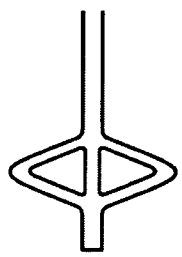

FIGS. 14A-14J are elevation front views of various anchors that may be used alone or in combination to anchor or bias a medical lead and/or electrode within a vessel in accordance with examples disclosed herein. The anchors illustrated in FIGS. 14A-14J may be employed, for example, in a manner as described with reference to anchor portion 230A of guidewire 230 and/or barbs 231 in FIG. 9. In such examples, anchor portion 230A of guidewire 230 and/or barbs 231 may take an alternative form to that shown in FIG. 9 including, e.g., the harpoon shapes of FIGS. 14B and 14C. In another example, a portion of lead 29 may be shaped as shown in FIG. 14A, 14D, or 14F and wedged into jugular vein 158 to anchor the lead and electrode 228 within the vein adjacent vagus nerve 150.

In addition to the intravascular techniques described with reference to FIGS. 9-14, examples according to this disclosure also include techniques employing an expandable and contractible generally cylindrical lead member that is temporarily deployable for testing multiple electrode orientations and combinations before deploying the member for chronic stimulation of target nerve tissue within a patient.

Figure 15:
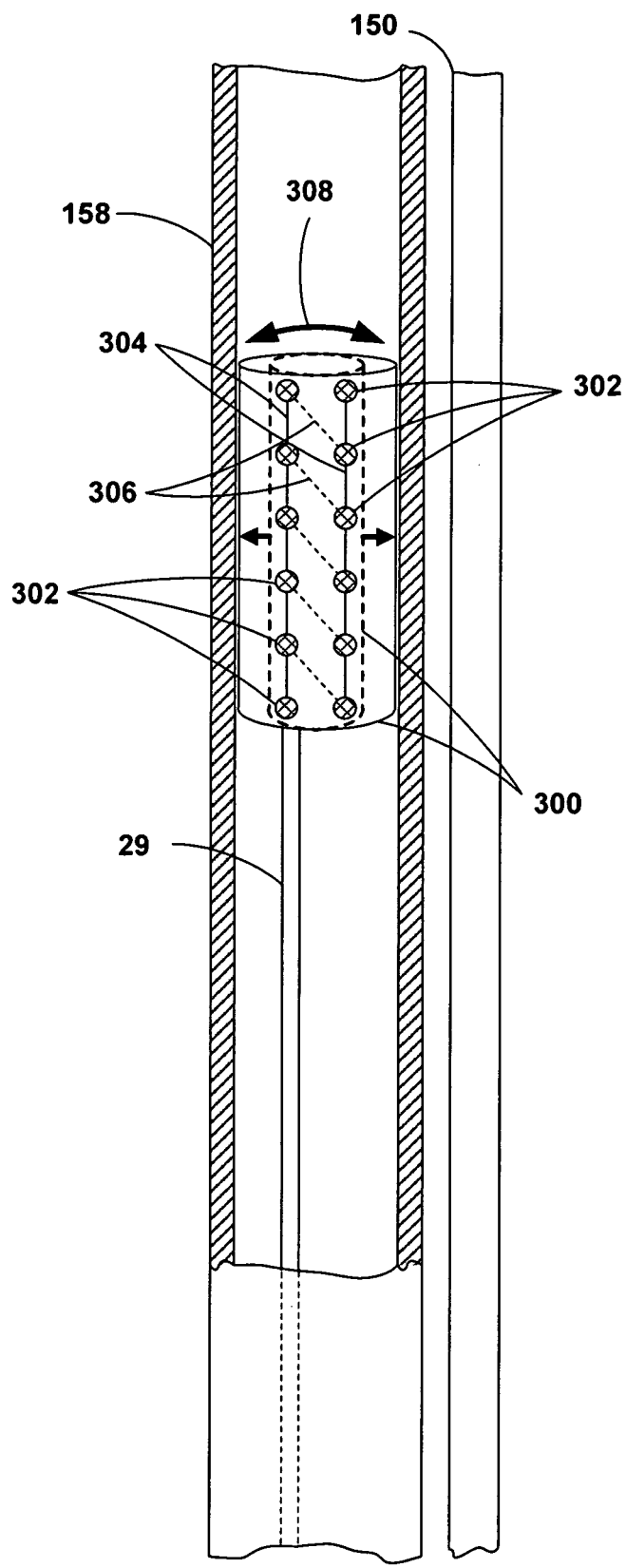
FIG. 15 is a schematic illustration depicting a cylindrical lead member connected to a medical lead placed intravascularly within the internal jugular vein adjacent a vagus nerve.
Figure 16:
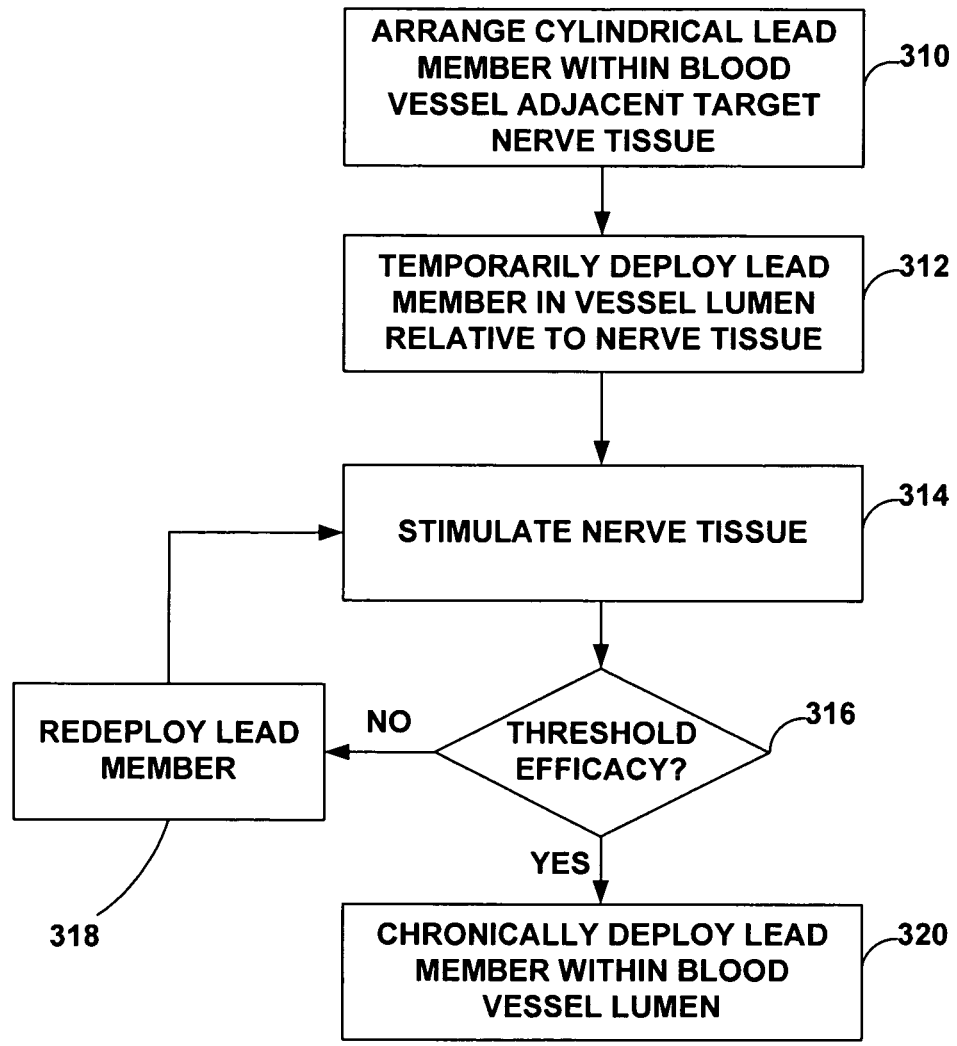
FIG. 16 is a flow chart illustrating an example method of intravascularly placing the cylindrical lead member of FIG. 15.

FIGS. 15 and 16 illustrate examples of intravascular lead placement techniques including a generally cylindrical expandable and contractible lead member in the context of vagal nerve stimulation in a human patient. FIG. 15 is a schematic illustration depicting lead 29 attached to cylindrical lead member 300, both of which are intravascularly placed adjacent vagus nerve 150 within internal jugular vein 158 in patient 12. After or during placement, lead 29 and lead member 300 may be connected to IMD 16 or INS 26 similar to lead 28 shown in FIGS. 1A and 1B respectively. FIG. 16 is a flow chart illustrating an example method of placing lead 29 and cylindrical lead member 300 in accordance with the example of FIG. 15. The example method of FIG. 16 includes arranging a generally cylindrical expandable and contractible lead member within a lumen of a blood vessel adjacent target nerve tissue (310), temporarily deploying the cylindrical lead member within the lumen relative to the nerve tissue (312), energizing one or more electrodes connected to the cylindrical lead member to deliver electrical stimulation from within the blood vessel lumen to the nerve tissue (314), comparing the efficacy of the nerve tissue stimulation to a threshold efficacy (316), and redeploying the cylindrical lead member within the lumen relative to the nerve tissue if the efficacy of the nerve tissue stimulation does not meet or exceed the threshold efficacy (318), or chronically deploying the cylindrical lead member in an expanded state within the lumen if the efficacy of the nerve tissue stimulation meets or exceeds the threshold efficacy (320). One example of the method illustrated in FIG. 16 will be described in the context of the example lead structure shown in FIG. 15.

The arrangement shown in FIG. 15 includes lead member 28, cylindrical lead member 300, and electrodes 302. As will be described in greater detail below, some examples may include additional components for arranging and deploying cylindrical lead member 300 within a blood vessel including, e.g., a delivery catheter and/or a stylus or other active deployment mechanism. Cylindrical lead member 300 is connected to a distal end of lead member 28. Electrodes 302 are connected to an exterior surface of lead member 300 and are arranged in columns 304 parallel to a longitudinal axis of lead member 300. Depending on how electrodes 302 are grouped, they may also be seen in FIG. 15 as arranged in columns 306 that wrap around the exterior surface of lead member 300 oriented at an angle with respect to the longitudinal axis of the cylindrical lead member. In other examples according to this disclosure, lead member 300 may include fewer or more electrodes 302 than shown in the example of FIG. 15. For example, lead member 302 may include more than two columns 306 of electrodes 302 distributed circumferentially around the exterior surface of cylindrical lead member 300. Cylindrical lead member 300 is an expandable and retractable component that may be deployed and redeployed passively or actively within a blood vessel. Lead member 300 is shown schematically in FIG. 15 in a contracted state in dashed lines and in an expanded state in solid lines. As described in greater detail below, cylindrical lead member 300 may be any one of a number of different structures that are capable of active and/or passive deployment and redeployment including, e.g., circular cylindrical members, wire mesh stents, and spiral wire and ribbon members.

In FIG. 15, lead 29 and cylindrical lead member 300 are arranged within the lumen of internal jugular vein 158 adjacent vagus nerve 150. In other examples, lead member 300 may be deployed in other blood vessels within patient 12 including, e.g., carotid artery 160 adjacent vagus nerve 150 or another vein or artery adjacent the target nerve tissue at which stimulation therapy is directed. Cylindrical lead member 300 may be guided to the target nerve tissue site within patient 12 by, e.g., a small transcutaneous incision to gain access to jugular vein 158 and then directed through the vein by, e.g., a delivery catheter to the target site adjacent vagus nerve 150.

After arranging cylindrical lead member 300 within the lumen of jugular vein 158 adjacent vagus nerve 150, lead member 300 may be temporarily deployed within the lumen relative to vagus nerve 150. Vagus nerve 150 is positioned within patient 12 outside of jugular vein 158, which has a generally tubular shape. Upon intravascular implantation of lead member 300 within jugular vein 158, the relative orientation of vagus nerve 150 around the periphery of jugular vein 158 may not be known without, e.g., complete dissection of carotid sheath 156. Deployment of lead member 300 within jugular vein 158 and stimulation of vagus nerve 150 by selected ones of electrodes 302 may initially be somewhat arbitrary with respect to the actual position of vagus nerve 150 without testing or feedback regarding the orientation and combination of electrodes 302 used. Therefore, cylindrical lead member 300 is capable of deployment and redeployment within jugular vein 158 adjacent vagus nerve 150 to test multiple orientations and combinations of electrodes 302 before deploying the lead member for chronic treatment of patient 12.

As indicated in FIG. 15 by arrow 308, lead member 300 is capable of being rotated within jugular vein 158 to vary the orientation of lead member 300, and thereby electrodes 302 within the vein. Lead member 300 may be oriented within jugular vein 158 both by rotating the lead member and also may be, in some examples, temporarily expanded to abut the walls of the lumen of vein 158 as shown in FIG. 15. In addition to orienting and expanding lead member 300, electrodes 302 may be selectively activated in different combinations in a manner similar to that described with reference to FIG. 2. For example, lead 29 and cylindrical lead member 300 may be connected to IMD 16 shown in FIGS. 1A and 2. Neurostimulation therapy module 106 of IMD 16 may include a switching module to selectively couple pairs of electrodes 302 to signal generator 112 and/or sensing module 114 to form different anode-cathode combinations. The switching module may include, e.g., a switch array, switch matrix, multiplexer, or any other type of switching device suitable to selectively couple stimulation energy to selected electrodes. In one example, the switching module may select combinations of electrodes 302 grouped along longitudinal column 304 in FIG. 15. In another example, however, the switching module may select combinations of electrodes 302 grouped along the skewed columns 306. In this manner, deploying lead member 300 within the lumen of jugular vein 158 may include both orienting and expanding lead member 300 and electrodes 302 within the vein, and selecting combinations of electrodes 302 to stimulate (and/or sense nerve signals from) vagus nerve 150. During the placement of lead member 300, lead 29 may be transcutaneously connected to IMD 16 to test the placement of lead member 300 prior to implanting the device within patient 12. In another example, lead 29 may be connected to an external neurostimulation device that is configured to deliver electrical stimulation to vagus nerve 150 while lead member 300 is being positioned relative thereto within vein 158.

After cylindrical lead member 300 and electrodes 302 have been temporarily deployed within jugular vein 158, one or more of the electrodes may be energized to deliver electrical stimulation to vagus nerve 150. During test stimulation of vagus nerve 150, a portion of lead 29 extending away from a distal end to which lead member 300 and electrodes 302 may be connected, e.g., transcutaneously to an external neurostimulation device that is configured to deliver electrical stimulation to the target nerve tissue, e.g., vagus nerve 150 while lead member 300 and electrodes 302 are being positioned relative thereto within vein 158. After cylindrical lead member 300 is placed adjacent vagus nerve 150 and connected to the external neurostimulator, the device, either automatically or as partially or completely commanded by a programmer, such as programmer 24, may deliver electrical stimulation therapy to and/or receive sensor feedback from vagus nerve 150 through one or more of electrodes 302.

In the example of FIGS. 14 and 15, as well as other examples disclosed herein, the efficacy of the electrical stimulation delivered by electrodes 302 to vagus nerve 150 may be compared to a threshold efficacy to determine whether or not cylindrical lead member 300 and electrodes 302 are satisfactorily positioned with respect to nerve 150 and/or an optimal combination of electrodes 302 has been selected to deliver stimulation to the nerve. As described above with reference to FIGS. 9 and 10, efficacy may be measured, in general, by verbal feedback from patient 12, clinician observation of various conditions of patient 12, or sensory feedback from one or more sensors. Various physiological signals may be observed to measure the efficacy of the test stimulation, and thereby the need to reposition lead member 300 relative vagus nerve 150. For example, to determine the response to stimulation of vagus nerve 150, ECG, heart rate, blood pressure, blood flow, cardiac output, and/or breathing, of patient 12 can be sensed or observed.

In the event the nerve tissue stimulation meets or exceeds the threshold efficacy, cylindrical lead member 300, to which electrodes 302 are attached, may be chronically deployed in an expanded state within jugular vein 158 adjacent vagus nerve 150. The orientation of cylindrical lead member 300 and selected combination of electrodes 302 that delivered therapy to patient 12 meeting or exceeding the threshold efficacy may be used to deliver chronic, i.e. long term therapy to the patient. On the other hand, if the nerve stimulation delivered by cylindrical lead member 300 and electrodes 302 does not provide the threshold level of efficacy in treating patient 12, lead member 300 may be redeployed within jugular vein 158 relative to vagus nerve 150. As with the initial temporary deployment, redeploying lead member 300 may include orienting the lead member by rotating within jugular vein 158, as well as selecting one or more combinations of electrodes 302 to stimulate vagus nerve 150. In some examples of redeployment, lead member 300 may also be contracted and then re-expanded to abut the walls of the lumen of jugular vein 158 as shown in FIG. 15. For example, in the event lead member 300 was previous expanded within jugular vein 158, the lead member may need to be contracted in order to be reoriented by rotating it within the vein. After redeploying cylindrical lead member 300, the process of stimulating vagus nerve 150 and comparing the efficacy of the nerve stimulation to a threshold efficacy may be repeated until the arrangement of lead member 300 with respect to vagus nerve 150 delivers electrical stimulation therapy that meets or exceeds the threshold efficacy level.

After determining a placement location that delivers satisfactory treatment efficacy, cylindrical lead member 300, to which electrodes 302 are attached, may be chronically deployed in an expanded state within jugular vein 158 adjacent vagus nerve 150. After chronic deployment of lead member 300, a portion of lead 29 extending away from a distal end toward which lead member 300 is arranged may be guided to connect with, e.g., IMD 16. In one example, lead 29 may be guided intravascularly to an implantation location of IMD 16 within patient 12. In other examples, lead 29 may be tunneled through tissue of patient 12 to be connected to IMD 16. After lead 29 is placed adjacent vagus nerve 150 and connected to IMD 16, IMD 16, either automatically or as partially or completely commanded by programmer 24, may deliver electrical stimulation therapy to and/or receive sensor feedback from vagus nerve 150 through electrodes 302.

Figure 17A:
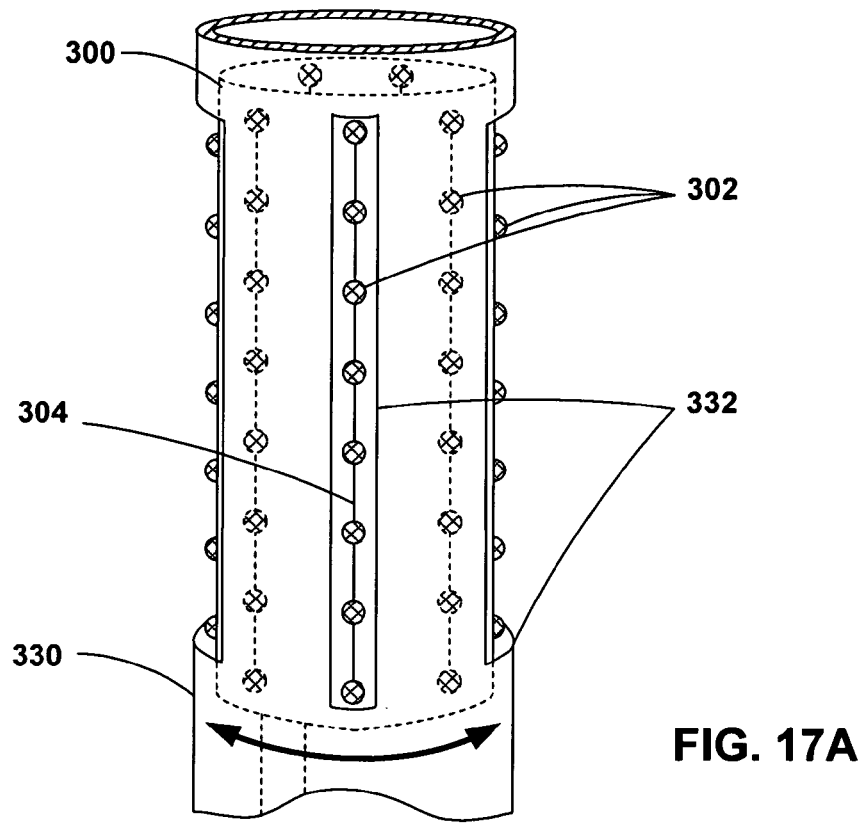
FIGS. 17A and 17B are schematic illustrations of a cylindrical lead member arranged within a delivery catheter.
Figure 17B:
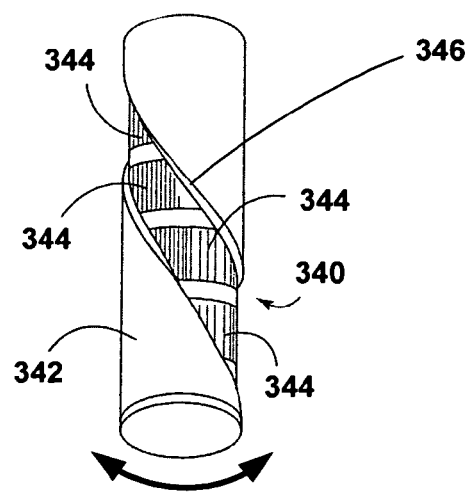

FIGS. 17A and 17B, and 18A-18D show several examples of cylindrical lead member 300 and delivery mechanisms appropriate for use in the example of FIGS. 15 and 15. FIGS. 17A and 17B are schematic illustrations of a cylindrical lead member arranged within a delivery catheter for deploying and redeploying the lead member within jugular vein 158 relative to vagus nerve 150. FIGS. 18A-18D are schematic illustrations of different examples of a cylindrical lead member that is expandable and contractible for deployment and redeployment within vein 158.

Generally speaking, there are several methods by which cylindrical lead member 300 may be temporarily and then chronically deployed within a blood vessel to test various orientations and combinations of electrodes 302 relative to vagus nerve 150. In some examples, cylindrical lead member 300 may be arranged adjacent vagus nerve 150 within a delivery mechanism that allows for the flexible orientation and selection of combinations of electrodes 302 within jugular vein 150 relative to the position of vagus nerve 150. For example, lead member 300 may be arranged within a delivery catheter that accommodates relative movement of the lead member and the catheter to expose different combinations of electrodes 302 oriented in different positions within vein 158 relative to vagus nerve 150. In other examples, cylindrical lead member 300 may be actively expandable and contractible such that the lead member may be expanded within jugular vein 158 and thereafter contracted and re-expanded in a different orientation relative to vagus nerve 150.

FIGS. 17A and 17B are schematic illustrations of a cylindrical lead member arranged within a delivery catheter that accommodates relative movement of the lead member and the catheter to expose different combinations of electrodes 302 oriented in different positions within vein 158 relative to vagus nerve 150. In FIG. 17A, lead 29 and cylindrical lead member 300 connected thereto are arranged within delivery catheter 330. Electrodes 302 are connected to lead member 300 and arranged in columns 304 that are generally parallel to a longitudinal axis of the lead member. Catheter 330 includes a plurality of apertures 332 that are shaped and sized to expose groups of electrodes 302. In the example of FIG. 17A, apertures 332 are generally rectangular slots in catheter 330. However, in other example, apertures 332 may be, e.g., holes arranged to expose one or more of electrodes 302.

In practice, delivery catheter 330 and lead member 300 may be guided intravascularly to a target tissue site through jugular vein 158 adjacent vagus nerve 150. Cylindrical lead member 300 may be oriented within catheter 330 such that select groups of electrodes 302 are exposed by apertures 332. In the example of FIG. 17A, electrodes 302 will be generally exposed in groups arranged along longitudinal columns 304. However, in other examples, apertures 332 may be shaped and oriented to expose one or more electrodes 302 in different groups including, e.g., groups arranged along columns oriented at an angle with respect to a longitudinal axis of lead member 300, such as columns 306 shown in FIG. 15. In any event, after lead member 300 and electrodes 302 are oriented within catheter 330, different combinations of electrodes 302 may deliver electrical stimulation to vagus nerve 150. Cylindrical lead member 300 and/or catheter 330 may be reoriented within jugular vein 158 one or more times to test different orientations and combinations of electrodes 302 until a threshold efficacy is indicated. Thereafter, cylindrical lead member 300 and electrodes 302 may be chronically deployed in an expanded state by, e.g., withdrawing delivery catheter 330 to allow lead member 300 to passively expand to abut the walls of the lumen of jugular vein 158.

In FIG. 17B, cylindrical lead member 340 is arranged within delivery catheter 342. Electrodes 344 are connected to lead member 340. Electrodes 344 are ring electrodes arranged around the exterior surface of and distributed longitudinally along lead member 340. Catheter 342 includes helical aperture 346 that is shaped and sized to expose portions of each of electrodes 340 at different rotational orientations within a blood vessel. In the example of FIG. 17A, apertures 346 is a generally rectangular slot in catheter 342. However, in other examples, catheter 342 may include a series of holes arranged in a helical line to expose different portions of electrodes 344 oriented at different rotational positions.

Similar to the example of FIG. 17A, delivery catheter 342 and lead member 340 may be guided intravascularly to a target tissue site through jugular vein 158 adjacent vagus nerve 150. Cylindrical lead member 340 may be oriented within catheter 342 such that select portions of electrodes 344 are exposed at different rotational orientations with respect to vagus nerve 150. After lead member 340 and electrodes 344 are oriented within catheter 346, different combinations of electrodes 344 may deliver electrical stimulation to vagus nerve 150. Catheter 346 may then be rotated relative to lead member 340 within jugular vein 158 one or more times to test different orientations and combinations of electrodes 344 until a threshold efficacy is indicated.

The catheters shown in FIGS. 17A and 17B may, in some examples, act as permanent components deployed along with cylindrical lead members, instead of temporary delivery components that are used to arrange and deploy the lead members and are thereafter removed. For example, the catheters and the cylindrical lead members may be arranged within a blood vessel such that the catheter abuts and thereby is fixed within the lumen of the blood vessel. In such examples, the cylindrical lead member may be rotated within the catheter to vary electrode orientation and combinations. The lead member may remain in an expanded state abutting a lumen of the catheter from initial implantation until chronic deployment, or, in other examples, may contract to be reoriented and expand to test the new electrode orientation and/or combination. In any event, the catheters may remain deployed along with the cylindrical lead members within the blood vessel for chronic treatment of a patient.

FIGS. 18A-18D are schematic illustrations of different examples of a cylindrical lead member that is expandable and contractible for deployment and redeployment within jugular vein 158 of patient 12. FIGS. 18A and 18B show mesh stent lead member 350 with different electrode configurations, while FIGS. 18C and 18D show two different helical lead members 352 and 354 respectively. In FIGS. 18A and 18B, mesh stent lead member 350 includes a plurality of material segments 356 each of which is pivotally joined at either end to another segment at a vertex. Material segments 356 may be constructed from various biocompatible materials that resists corrosion and degradation from bodily fluids including, e.g., titanium or biologically inert polymers. Generally speaking, mesh stent lead member 350 is expandable and contractible by rotation of material segments 356 with respect to each other at the plurality of vertices at which the segments are pivotally joined. As mesh stent lead member 350 contracts, material segments 356 rotate such that the angle of each segment with respect to a longitudinal axis of lead member 350 decreases, which in turn decreases the diameter and increases the overall length of the lead member. Conversely, as mesh stent lead member 350 expands, material segments 356 rotate such that the angle of each segment with respect to the longitudinal axis of lead member 350 increases, which in turn increases the diameter and decreases the overall length of the lead member. Other examples according to this disclosure may include stent lead members having different configurations than lead member 350 of FIGS. 18A and 18B. For example, in one example, a mesh stent member may include fewer or more material segments pivotally joined at fewer or more vertices to form coarser or finer meshes than mesh stent lead member 350. In another example, a stent lead member may be constructed from a polymer that is expandable to take the shape of the blood vessel in which it is arranged. In still another example, a mesh stent member may include a resorbable material interconnecting some or all of the mesh that would, over a period of time leave only the mesh of material segments and electrodes within the blood vessel of the patient.

FIGS. 18A and 18B illustrate stent lead member 350 with different electrode configurations. In FIG. 18A, electrodes 302 are connected to lead member 350 substantially coincident with the vertices at which material segments 356 are joined. In other examples, only some of the junctions between material segments 356 may include electrodes 302 arranged thereon or about. Electrodes 302, as illustrated in FIG. 18A, may protrude from the exterior surface of lead member 350, or any other cylindrical lead member according to this disclosure. In this manner, electrodes 302 may penetrate the wall of the blood vessel lumen in which lead member 350 is arranged, e.g. jugular vein 158, to assist in fixing the lead member within the vessel. In FIG. 18B, on the other hand, lead 29 is wrapped partially or completely around stent lead member 350 and includes ring electrodes 358 attached thereto. Wrapping lead 29 around lead member 350 along a helical trajectory as shown in FIG. 18B may provide a mechanical advantage for expansion of the lead member, because, in such an orientation, lead 29 may not need to stretch as the overall length of lead member 350 increases.

FIGS. 18C and 18D show two different helical lead members 352 and 354 respectively. Lead member 352 is a helical wire, while lead member 354 is a helical ribbon. Both wire and ribbon helical lead members 352 and 354 include electrodes 302 electrically connected to lead 29 and arranged generally in one or more lines parallel to the helical trajectory of each lead member. Generally speaking, helical lead members 352 and 354 are expandable and contractible by bringing their respective ends 352A, 352B and 354A, 354B closer together or further apart. In the case of helical wire lead member 352, as ends 352A and 352B are brought closer together, individual windings of the helical wire are also brought closer together and the diameter of the helix of lead member 352 expands. Conversely, as ends 352A and 352B are brought further apart, individual windings of the helical wire are also brought further apart and the diameter of the helix of lead member 352 contracts. In the case of helical ribbon lead member 354, as ends 354A and 354B are brought closer together, helical slot 360 closes and the diameter of the helix of lead member 354 expands. Conversely, as ends 354A and 354B are brought further apart, helical slot 360 is opened and the diameter of the helix of lead member 354 contracts.

Cylindrical lead members employed in examples according to this disclosure, in general, may include several additional features. In some examples, a lead member may include a non-conductive material that insulates non-targeted tissue from stimulation pulses delivered by one or more electrodes connected to the lead member or otherwise isolates one or more electrodes from, e.g., other parts of the lead member. In addition to employing electrodes that protrude from the exterior surface of a cylindrical lead member to assist in fixation within a vessel (see, e.g., FIG. 18A), the lead member may include an abrasive or otherwise coarse exterior surface or a drug-eluting coating that promotes tissue growth around the lead member, e.g. promotes fibrosis. Conversely, in other examples, a cylindrical lead member according to this disclosure may include a drug-eluting coating that inhibits tissue growth, such as fibrosis to, e.g., increase the long term period over which the cylindrical member may be redeployed within a blood vessel. Additionally, in some examples, a cylindrical lead member may include a drug-eluting coating that prevents or inhibits stenosis of the blood vessel in which it is arranged. In other examples, the cylindrical lead member may include a number microhooks or small barbs arranged on an exterior surface to hold the lead member in place within the blood vessel.

Cylindrical lead members according to this disclosure may also be deployed and redeployed with the assistance of, e.g. a cup and release plate that receive one end of the lead member and serve to retain the lead member in place when, e.g., a sheath is retracted to temporarily or chronically deploy the lead member in a blood vessel. In some examples, the cup may be relatively deep to encapsulate a large longitudinal length of a proximal end of the lead member that is configured to expand to deploy the lead member. The cup may hold and encapsulate the proximal end of the lead member while a sheath extends over and encapsulates the lead member and the cup prior to deployment and after the sheath is retracted. After the sheath is retracted to partially deploy the lead member, e.g., allow the distal end to expand in the blood vessel, the sheath may then either be extended again to redeploy the cylindrical lead member, or the release plate may be extended to push out and thereby release and deploy the proximal end of the cylindrical member from the cup. Other examples and a more detailed explanation of deployment mechanisms including such cup arrangements are described in U.S. Patent Publication No. 2007/0043420 A1 to Timothy W. Lostetter, filed on Aug. 17, 2005 and entitled "APPARATUS AND METHOD FOR STENT-GRAFT RELEASE USING A CAP," the entire content of which is incorporated herein by this reference.

In some examples, a cylindrical lead member may include an electrical stimulator and, in some cases, need not be coupled to an implantable medical device via a lead. In such examples, the electrical stimulator on, within or attached to the cylindrical lead member may be powered by radio frequency pulses delivered from either an external or a subcutaneously implanted RF transmitter to a receiver unit arranged with the stimulator or cylindrical lead member. In other examples, some part of the stimulator or cylindrical lead member may be composed of a piezoelectric material that can generate current when excited mechanically by ultra sound waves transmitted from an external or implanted source.

Similar to intravascular techniques, transvascular lead placement proximate a target nerve tissue site generally requires minimally invasive surgical techniques because the leads are guided to the site through a blood vessel, e.g., a vein or artery that may be readily accessible, e.g., transcutaneously through a small incision. Unlike intravascular, however, transvacular techniques guide the lead adjacent the target tissue site and then pierce the vessel wall to arrange the lead and electrodes outside of the vessel adjacent the nerve tissue at which therapy is directed. Transvascular lead placement techniques according to this disclosure provide for lead placement relative to the target nerve tissue and neighboring blood vessels to improve the therapeutic effects of electrical stimulation provided to the patient by lead electrodes. Additionally, guided transvascular lead placement as described herein may avoid safety risks of such procedures including, e.g., piercing adjacent vessels, such as an artery. The disclosed transvascular techniques generally include improving lead placement by locating target nerve tissue with a sensor, such as an IVUS imaging system, through a blood vessel adjacent the target tissue. After a placement location is determined, one or more leads including one or more electrodes may be deployed through the vessel wall and anchored to the vessel wall or other tissue near the target nerve tissue.

Transvascular techniques generally include improving lead placement by locating target nerve tissue with a sensor including, e.g., an IVUS imaging system through a blood vessel adjacent the target tissue. After an optimal placement location is determined relative to the nerve tissue with the assistance of the tissue sensor, one or more leads including one or more electrodes may be deployed through the vessel wall and anchored to the vessel wall or other tissue near the target nerve tissue.

Figure 19:
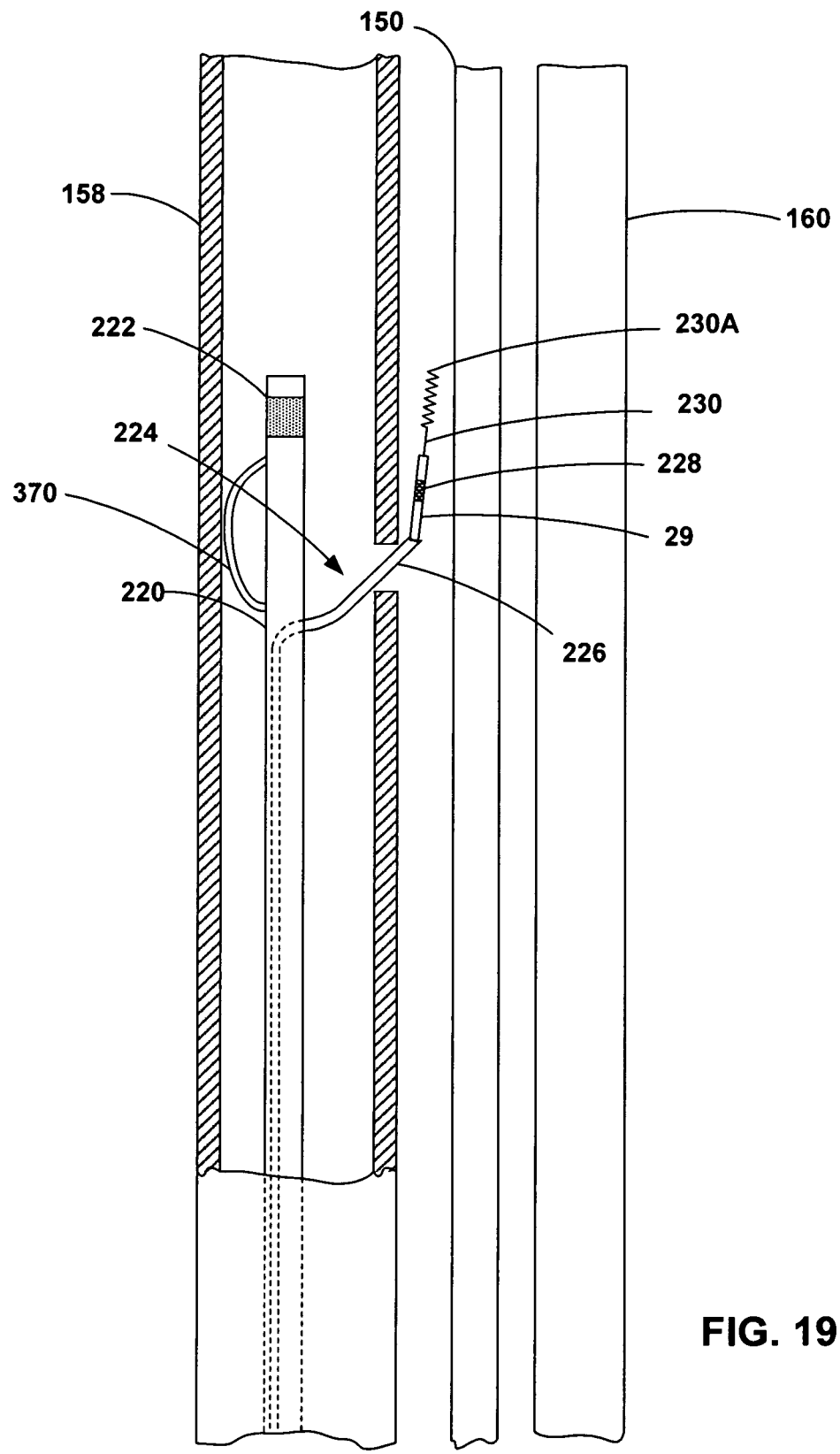
FIG. 19 is a schematic illustration depicting a medical lead placed transvascularly through a wall of the internal jugular toward a vagus nerve.
Figure 20:
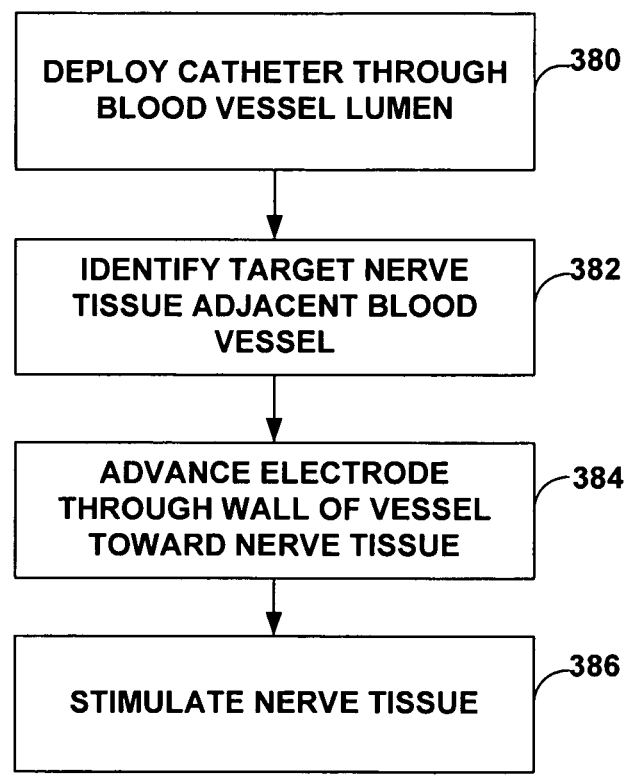
FIG. 20 is a flow chart illustrating an example transvascular lead placement method.

FIGS. 18 and 19 illustrate examples of transvascular lead placement techniques in the context of vagal nerve stimulation in a human patient. FIG. 19 is a schematic illustration depicting lead 29 transvascularly placed adjacent vagus nerve 150 outside of internal jugular vein 158 in patient 12. After or during placement, lead 29 may be connected to IMD 16 or INS 26 similar to lead 28 shown in FIGS. 1A and 1B respectively. FIG. 20 is a flow chart illustrating an example method of placing lead 29 in accordance with the example of FIG. 19. The example method of FIG. 20 includes deploying a delivery catheter through a lumen of a blood vessel to a target nerve tissue site (380), identifying a location of the nerve tissue with respect to the blood vessel with one or more sensors connected to the delivery catheter (382), advancing an electrical stimulation electrode from the catheter through a wall of the blood vessel toward the nerve tissue (384), and energizing the electrode to deliver electrical stimulation to the nerve tissue (386). One example of the method illustrated in FIG. 20 will be described in the context of the example lead placement structure shown in FIG. 19.

The arrangement shown in FIG. 19 includes delivery catheter 220, sensor 222, deployment member 224, and spline 370. Sensor 222 is connected to catheter 220 toward a distal end thereof. Deployment member 224 is extendable and retractable from catheter 220. Spline 370 is also connected to a distal end of catheter 220 and is deployable to stabilize the catheter within jugular vein 158. Sensor 222 is arranged between the distal end of catheter 220 and the location along catheter 220 from which deployment member 224 is extendable and retractable. Deployment member 224 includes tubular member 226, lead 29, electrode 228, and guidewire 230. Guidewire 230 includes anchor portion 230A at a distal end thereof. Electrode 228 is connected toward a distal end of lead 29. Lead 29 and guidewire 230 are received within and advanceable through a lumen of tubular member 226. Lead 29 is advanceable along guidewire 230.

In FIG. 19, catheter 220 is deployed through internal jugular vein 158 of patient 12 to a target nerve tissue stimulation site. In other examples, catheter 220 may be deployed in other blood vessels within patient 12 including, e.g., carotid artery 160, or the superior or inferior vena cava. Catheter 220 can be any suitable delivery catheter capable of intravenous delivery within patient 12 and adapted to accommodate sensor 222 and deployment member 224. Sensor 222 is connected to the distal end of catheter 220 and is configured to detect the position of vagus nerve 150 relative to jugular vein 158. Sensor 222, in general, may be any suitable imaging or guidance system including, e.g., a fiberoptic endoscope, ultrasound imaging system, or any other on-board imaging system capable of positioning catheter 220 to advance electrode 228 through jugular vein 158 toward vagus nerve 150 by providing an image of the area adjacent the location of sensor 222 on catheter 220. In some examples, sensor 222 could be an array of receivers in relationship to a transmitter that provide an image of surrounding tissue and structures including vagus nerve 150 and carotid artery 160. In other examples, sensor 222 may be configured to send or receive signals to or from any of a series of known signal generators including sonic, electromagnetic, light or radiation signals. In still other examples, sensor 222 may be an optical oxygen content sensor that may be used to ensure that lead 29 and electrode 228 are not directed toward, e.g., carotid artery 160 during lead placement. In some examples, sensor 222 may be employed in conjunction with one or more opaque markers viewable with fluoroscopic techniques or with an irrigated lumen that dispenses contrast media to assist in imaging the position of vagus nerve 150 relative to jugular vein 158. In still other examples, sensor 222 may employed in addition to a separate optical oxygen content or venous biomarker sensor that may be used to ensure that lead 29 and electrode 228 are not directed toward, e.g., carotid artery 160 during lead placement. In some such examples, an optical oxygen content or venous biomarker sensor may be connected to deployment member 224 to detect the presence of and reduce the risk of piercing or otherwise damaging carotid artery 160 as deployment member 224 including electrode 228 is advanced through the wall of the lumen of jugular vein 158 toward vagus nerve 150.

In one example, sensor 222 is an intravenous ultrasound ("IVUS") imaging system that is adapted to radiate ultrasonic waves out from sensor 222 to generate a two dimensional image of the tissue and structures surrounding catheter 220 and sensor 222. When activated, sensor 222 may produce an imaging field from ultrasonic waves produced by and radiating radially from catheter 220 and sensor 222 (see, e.g., FIG. 11). The size of the imaging field may vary depending on the particular configuration and capabilities of sensor 222. The tissues and other structures caught within the imaging field of sensor 222 may be distinguished from one another and the relative positioning of the different structures may be discerned. Therefore, in the context of transvacular lead placement, vagus nerve 150, jugular vein 158, and carotid artery 160 may be caught within the imaging field of sensor 222 to detect, e.g., the position of nerve 150 relative to vein 158.

After sensor 222 identifies the location of vagus nerve 150 with respect to jugular vein 158, deployment member 224 including electrode 228 may be advanced through the wall of the lumen of jugular vein 158 toward vagus nerve 150. Deployment member 224, in general, is extendable and retractable from catheter 220 from, e.g., an aperture formed in a sidewall thereof. Deployment member 224 includes tubular member 226, lead 29, electrode 228, and guidewire 230. Tubular member 226 may be any structure including at least one lumen through which various electrode deployment structures including, e.g., lead 29 and guidewire 230 may be advanced to place an electrode outside of vein 158 adjacent vagus nerve 150. In the example of FIG. 19, tubular member 226 may be a needle capable of piercing the wall of the lumen of vein 158 and including a lumen in which lead 29 and guidewire 230 are received and through which the same are advanceable. Electrode 228 is connected to lead 29, which is advanceable along guidewire 230.

With the aid of sensor 222, deployment member 224 is advanced from catheter 220 through jugular vein 158 toward vagus nerve 150. Lead 29, to which electrode 228 is connected, and guidewire 230 may be advanced through a lumen of deployment member 224 to position electrode 228 outside of vein 158 adjacent vagus nerve 150. Guidewire 230 includes anchor portion 230A at a distal end thereof that is configured to anchor deployment member 224, lead 29 and electrode 228, and guidewire 230 to tissue outside of vein 158. In the example of FIG. 19, anchor portion 230A includes guidewire 230 formed in a spiral that is configured to be twisted tissue adjacent vagus nerve 150. Anchor portion 230A can be freed from the tissue by either untwisting guidewire 230, or in the case that guidewire 230 is sufficiently flexible, pulling the wire away from the spiraling anchor portion 230A to effectively unwind and release the anchor from the tissue.

Having deployed catheter 220, detected the location of vagus nerve 150 relative to jugular vein 158, and advanced electrode 228 through vein 158 toward vagus nerve 150, electrical stimulation may be delivered to vagus nerve 150 via electrode 228. A portion of lead 29 extending away from a distal end toward which electrode 228 is arranged may be guided to connect with IMD 16. In one example, lead 29 may be guided intravascularly to an implantation location of IMD 16 within patient 12. In other examples, at least a portion of lead 29 may be tunneled through tissue of patient 12 to be connected to IMD 16. Although the example of FIGS. 18 and 19 is described with reference to implanted medical device 16 arranged within patient 12, examples according to this disclosure also include lead 29 connected transcutaneously to an external medical device that is configured to deliver electrical stimulation to the target nerve tissue, e.g., vagus nerve 150. After lead 29 is placed adjacent vagus nerve 150 outside of jugular vein 158 and connected to IMD 16, IMD 16, either automatically or as partially or completely commanded by programmer 24, may deliver electrical stimulation therapy to and/or receive sensor feedback from vagus nerve 150 through electrode 228.

In the example of FIGS. 18 and 19, as well as other examples disclosed herein, the efficacy of the electrical stimulation delivered by electrode 228 to vagus nerve 150 may be compared to a threshold efficacy to determine whether or not electrode 228 is satisfactorily positioned with respect to nerve 150. Efficacy may be measured, in general, by verbal feedback from patient 12, clinician observation of various conditions of patient 12, or sensory feedback from one or more devices including, e.g., ICD 17 shown in FIG. 1A or cardiac therapy module 104 shown in FIG. 4. For example, to determine the response to stimulation of vagus nerve 150, ECG, heart rate, blood pressure, blood flow, cardiac output, and/or breathing, of patient 12 can be sensed or observed. In another example, efficacy may be measured by a sensor including, e.g., an accelerometer that determines if stimulation of the neck muscles or phrenic nerve of patient 12 is occurring with or instead of stimulation of vagus nerve 150.

Figure 21A:
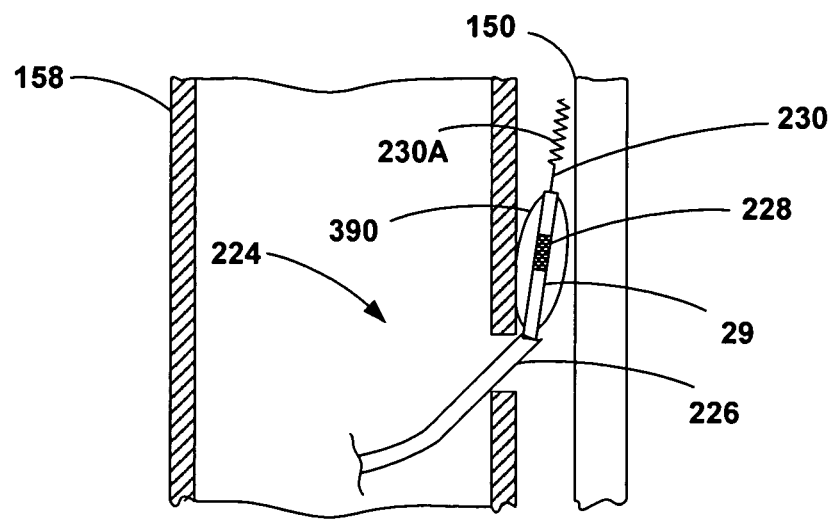
FIGS. 21A-21D show several example deployment members for use in transvascular lead placement methods and systems according to this disclosure.

FIGS. 21A-21D show several alternative examples of deployment member 224 for use in methods and systems according to this disclosure. In general, FIGS. 21A-21D show different arrangements and combinations of anchoring members and electrodes with respect to tubular member 226, lead 29, and guidewire 230 of deployment member 224. In the interest of simplicity, catheter 220 has been omitted from the illustrations of FIGS. 21A and 21B. In FIG. 21A, deployment member 224 is advanced through the lumen wall of jugular vein 158 toward vagus nerve 150 and includes tubular member 226, lead 29, electrode 228, guidewire 230, and expandable member 390. In some examples, it may be desirable or necessary to use expandable member 390 to enlarge the tract along which tubular member 226 and guidewire 230 are advanced through and outside vein 158 prior to placing lead 29 and electrode 228. In one example employing expandable member 390, tubular member 226 and guidewire 230 may be advanced through the lumen wall of jugular vein 158 toward vagus nerve 150. Thereafter, expandable member 390 may be advanced over guidewire 230 and used to enlarge the tract along which lead 29 and electrode 228 will be advanced. The expandable member 390 may, in some examples, be a balloon catheter including, e.g., an angioplasty catheter. Instead of or in addition to expandable member 390, other tract enlarging devices may be employed including, e.g., electrosurgical debulking devices or tissue cutting devices.

In addition to or in lieu of tract enlargement, in some examples, expandable member 390 may provide additional stabilization or biasing of lead 29 or other components of deployment member 224 outside of jugular vein 158 adjacent vagus nerve 150. For example, expandable member 390 may push against the exterior surface of jugular vein 158 as shown in FIG. 21A to bias lead 29 and electrode 228 toward vagus nerve 150. In another example, expandable member 390 may further stabilize the placement of lead 29 and electrode 228 by expanding to apply force on jugular vein 158 and vagus nerve 150.

Figure 21B:
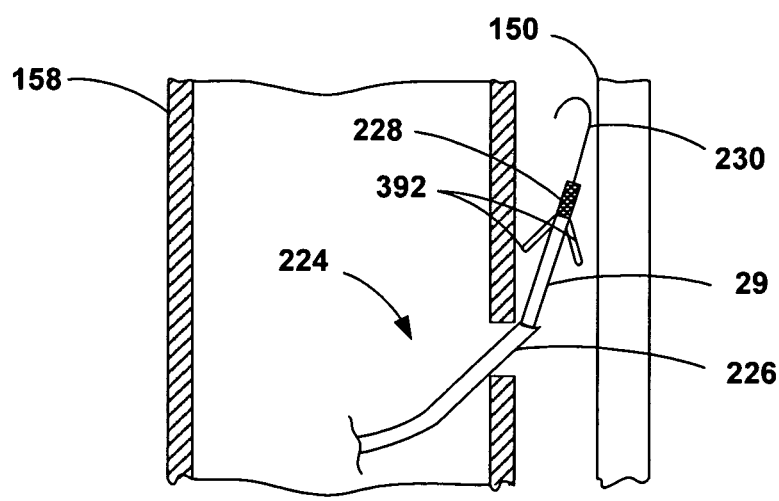

FIG. 21B shows deployment member 224 with anchor 392. In FIG. 21B, deployment member 224 is advanced through the lumen wall of jugular vein 158 toward vagus nerve 150 and includes tubular member 226, lead 29, electrode 228, guidewire 230, and anchor 392. Anchor 392 is connected to lead 29 and is configured to secure lead 29 and thereby electrode 228 to tissue outside of jugular vein 158 adjacent nerve 150. Anchor 392 may be any number of structures that are actively or passively deployable from within tubular member 226 to engage tissue within patient 12. In the example of FIG. 21B, anchor 392 is in the form of passive tines or barbs that protrude from lead 29 and that may engage tissue outside of jugular vein 158 after lead 29 is advanced through and out of tubular member 226. In other examples, anchor 392 may come in different shapes and sizes including, e.g., helical coils, C-shaped members, harpoon-like structures, hooks, expandable or serrated members, and the like. In FIG. 21B, anchor 392 is employed in lieu of anchor portion 230A of guidewire 230. However, in other examples both anchor 392 and anchor portion 230A may be used to securely deploy lead 29 and electrode 228 outside of jugular vein 158 adjacent vagus nerve 150.

The anchors illustrated in FIGS. 14A-14J and described with reference to intravascular lead placement techniques may also be used in transvascular techniques disclosed herein. One or more of the anchors illustrated in FIGS. 14A-14J may be employed, for example, alone or in combination in a manner as described with reference to anchor portion 230A of guidewire 230 in FIG. 19. In such examples, anchor portion 230A of guidewire 230 may take an alternative form to that shown in FIG. 19 including, e.g., the harpoon anchors of FIGS. 14B and 14C. In another example, one of the illustrated anchors of FIGS. 14A-14J may be employed as anchor 392 shown in FIG. 21B.

Figure 21C:
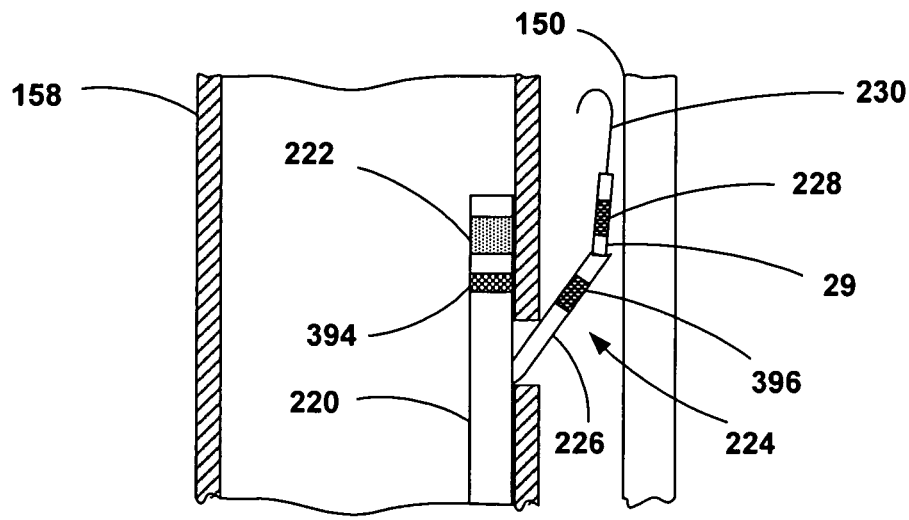

FIG. 21C shows catheter 220 with additional electrode 394 and deployment member 224 with additional electrode 396 connected to tubular member 226. In FIG. 21C, deployment member 224 is advanced through the lumen wall of jugular vein 158 toward vagus nerve 150 and includes tubular member 226, lead 29, electrode 228, guidewire 230, and additional electrodes 394, 396. Although transvascular placement examples of lead 29 have been described herein with reference to a single electrode 228 for simplicity, in practice, lead 29 will commonly include a plurality of electrodes that may be employed in different anode and cathode combinations to stimulate vagus nerve 150 as, e.g., described with reference to electrodes 80-83 in FIG. 2.

Additionally and as illustrated in FIG. 21C, catheter 220 may include electrode 394 in addition to lead electrode 228. In the example of FIG. 21C, deployment member 224 may be advanced through the wall of jugular vein 158 and thereafter used to pull catheter 220 and electrode 394 toward the lumen wall within jugular vein 158. For example, deployment member 224 may include an active or passive anchor (e.g. anchor portion 230A of FIG. 21A, or anchor 392 of FIG. 21B) that fixes deployment member 224 outside of vein 158 adjacent vagus nerve 150. After deployment member 224 is anchored outside of jugular vein 158, catheter 220 may be pulled along deployment member 224 to abut the wall of the lumen of jugular vein 158 as shown in FIG. 21C, thereby positioning electrode 394 within the vein proximate vagus nerve 150.

Deployment member 224 may also include electrodes in addition to lead electrode 228 arranged in different locations and/or connected to different components. In FIG. 21C, electrode 396 is connected to tubular member 226. In some examples, tubular member 226 and electrode 396 may be advanced through the wall of vein 158 toward vagus nerve 150 prior to chronically deploying lead 29 and electrode 228. In such examples, electrode 396 may be used to deliver test stimulation pulses to vagus nerve 150 to determine the efficacy of the placement of deployment member 224 outside of jugular vein 158 with respect to vagus nerve 150. After determining a position of deployment member that provides a threshold efficacy in stimulating vagus nerve 150, lead 29 and guidewire 230 may be advanced through tubular member 226 and lead 29 and electrode 228 may be chronically deployed along the wall of the lumen of jugular vein 158 adjacent vagus nerve 150.

Figure 21D:
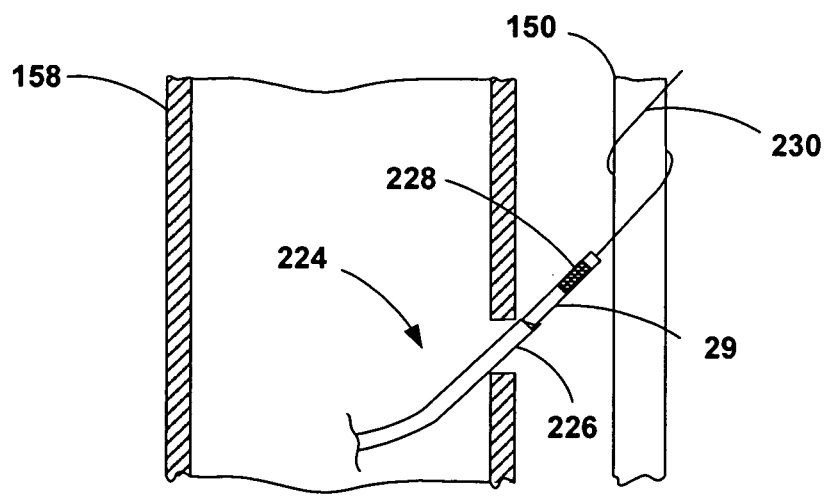

FIG. 21D shows guidewire 230 and lead 29 deployed transvascularly to create a cuff arrangement that wraps around vagus nerve 150. In FIG. 21D, deployment member 224 is advanced through the lumen wall of jugular vein 158 toward vagus nerve 150 and includes tubular member 226, lead 29, electrode 228, and guidewire 230. In some examples, it may be desirable to anchor and/or localize the stimulation field delivered by electrodes connected to lead 29 around the nerve. In one example, a curved member may be deployed from tubular member 226 to loop and thereby create a cuff around vagus nerve 150. The curved member may be, e.g., a tubular needle adapted to receive guidewire 230 and/or lead 29. In the example of FIG. 21D, the curved member is guidewire 230, which is advanced from tubular member 226 of deployment member 224 around vagus nerve 150. After guidewire 230 is arranged around nerve 150, lead 29 and electrode 228 may be advanced along the guidewire to wrap around the nerve.

In certain applications, transvascular lead placement may carry certain inherent risks. In some examples, advancing medical leads from within a lumen of a blood vessel, through a wall of the vessel to place the leads adjacent nerve tissue in an extravascular space may carry the risk of piercing or otherwise damaging other neighboring biological structures including, e.g., other blood vessels. In the context of vagal nerve stimulation/sensing examples disclosed herein, for example, transvascularly placing a lead adjacent vagus nerve 150 may carry the risk of piercing or otherwise causing damage to carotid artery 160 adjacent the nerve and jugular vein 158. Therefore, in some examples according to this disclosure, transvascular lead placement techniques may employ a deployment member part or all of which is constructed from a shape memory material such that the deployment member is configured to pass laterally through a vessel wall and turn outside of the vessel to be arranged longitudinally along the vessel adjacent the target nerve tissue. In this way, the deployment member and other components of the transvascular lead placement apparatus may reduce the risk of advancing too far laterally from the blood vessel and, e.g., piercing an adjacent vessel such as an artery.

Figure 22:
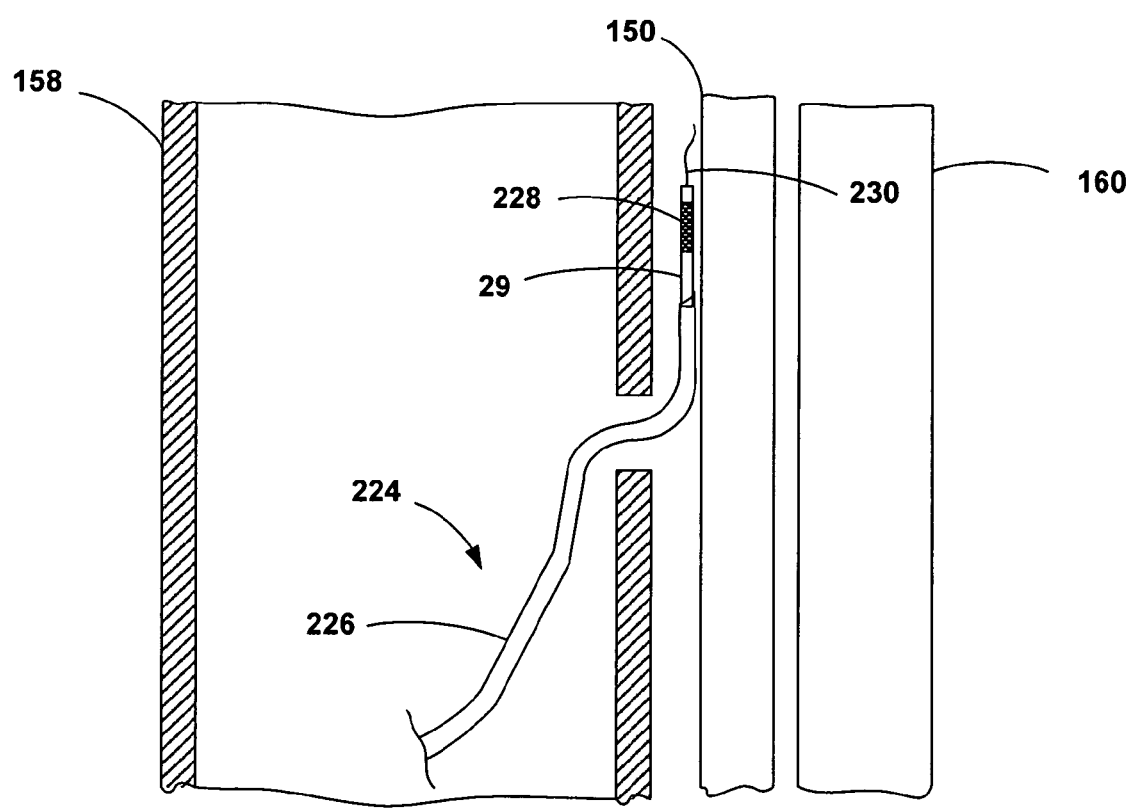
FIG. 22 shows one example of a deployment member that employs a guide member constructed from a shape memory material.

FIG. 22 shows one example of deployment member 224 employing tubular member 226 constructed from a shape memory material. Examples disclosed herein may use a variety of shape memory materials including, e.g., nickel titanium (NiTi) alloys. NiTi is a shape memory alloy, which is sometimes referred to as Nitinol. Other shape-memory alloys may also be used in examples disclosed herein including, e.g., copper tin (CuSn), indium titanium (InTi), and manganese copper (MnCu) alloys. A reversible, solid phase transformation known as martensitic transformation is the physical mechanism that underpins shape memory materials. Generally speaking, shape memory materials form a crystal structure that can undergo a change from one crystal form to another initiated by a temperature change or application of force. Above its transformation temperature, Nitinol, e.g., is superelastic, able to withstand a small amount of deformation when a load is applied and return to its original shape when the load is removed. Below its transformation temperature, it displays the shape memory effect. When it is deformed it will remain in that shape until heated above its transformation temperature, at which time it will return to its original shape. Nitinol is typically composed of approximately 50 to 55.6% nickel by weight. However, small changes in material composition can change the transition temperature of the alloy significantly. As such, Nitinol may or may not be superelastic at room temperature. The flexibility and unique properties of Nitinol to be used in a wide range of temperatures makes it suitable for many applications, particularly in medicine.

In FIG. 22, deployment member 224 includes tubular member 226, lead 29, electrode 228, and guidewire 230. Tubular member 226 may be any structure including at least one lumen through which various electrode deployment structures including, e.g., lead 29 and guidewire 230 may be advanced to place an electrode outside of vein 158 adjacent vagus nerve 150. In the example of FIG. 22, tubular member 226 may be a needle capable of piercing the wall of the lumen of vein 158 and including a lumen in which lead 29 and guidewire 230 are received and through which the same are advanceable. Electrode 228 is connected to lead 29, which is advanceable along guidewire 230.

Deployment member 224 is advanced from catheter 220 through jugular vein 158 toward vagus nerve 150. Lead 29, to which electrode 228 is connected, and guidewire 230 may be advanced through a lumen of deployment member 224 to position electrode 228 outside of vein 158 adjacent vagus nerve 150. In the example of FIG. 22, tubular member 226 is constructed from a shape memory material including, e.g., Nitonol and generally takes an S-shape after being advanced through the lumen of from catheter 220 (shown in FIG. 19) through the wall of jugular vein 158. The material properties and shape of tubular member 226 reduce the risk that the needle, or another component of deployment member 224 will advance too far laterally from jugular vein 158 and, e.g., pierce or otherwise damage carotid artery 160. After tubular member 226 is advanced through the wall of vein 158, guidewire 230 may be deployed and lead 29 and electrode 228 may be advanced along guidewire 230 to arrange electrode 228 adjacent vagus nerve 150.

In other examples according to this disclosure, other components of deployment member 224 may be constructed from a shape memory material. For example, guidewire 230 may, in addition to or in lieu of tubular member 226, be constructed from a shape memory material including, e.g., Nitonol. In some such examples, tubular member 226 of deployment member 224 is advanced from catheter 220 toward vagus nerve 150. Lead 29, to which electrode 228 is connected, and guidewire 230 may be advanced through a lumen of tubular member 226 to position electrode 228 outside of vein 158 adjacent vagus nerve 150. In particular, guidewire 230 is constructed from a shape memory material and generally takes an S-shape to pass out of tubular member 226, through the wall of vein 158, and run longitudinally along and adjacent to vagus nerve 150 outside of vein 158. After guidewire 230 is advanced through the wall of vein 158, lead 29 and electrode 228 may be advanced along guidewire 230 to arrange electrode 228 adjacent vagus nerve 150.

The extra, intra, and transvascular lead placement techniques disclosed herein may benefit, in some examples, from electrode pairs arranged in flanking, non-contacting relationship with the target nerve tissue. In one example, multiple leads are arranged longitudinally on opposing sides of and including electrodes in non-contacting relationship with the target nerve tissue. In another example, a single lead including multiple electrodes is arranged such that at least two of the electrodes are arranged on opposing sides of and in non-contacting relationship with the target nerve tissue. Such flanking, non-contacting electrode arrangements may provide one or more anode and cathode electrode combinations for electrical stimulation across the target nerve tissue without the deleterious effects of tissue contacting techniques, such as may be caused by, e.g., cuff electrodes.

Figure 23A:
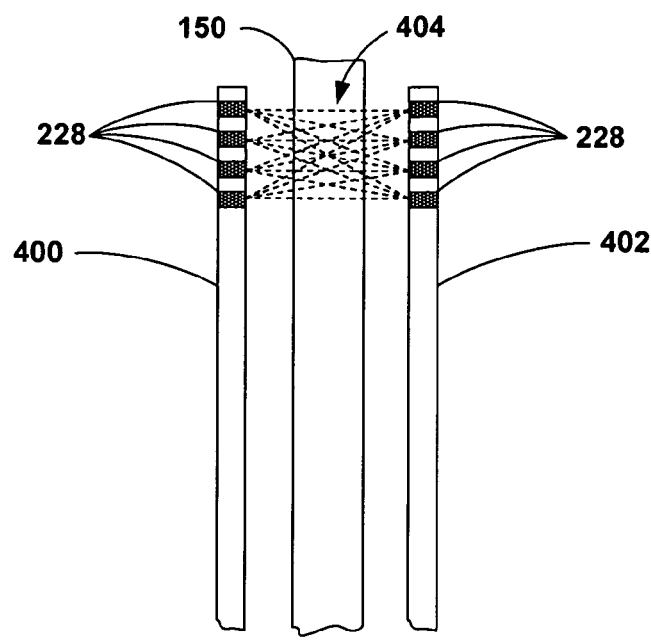
FIGS. 23A and 23B illustrate example arrangements of electrode pairs in flanking, non-contacting relationship with a vagus nerve.
Figure 23B:
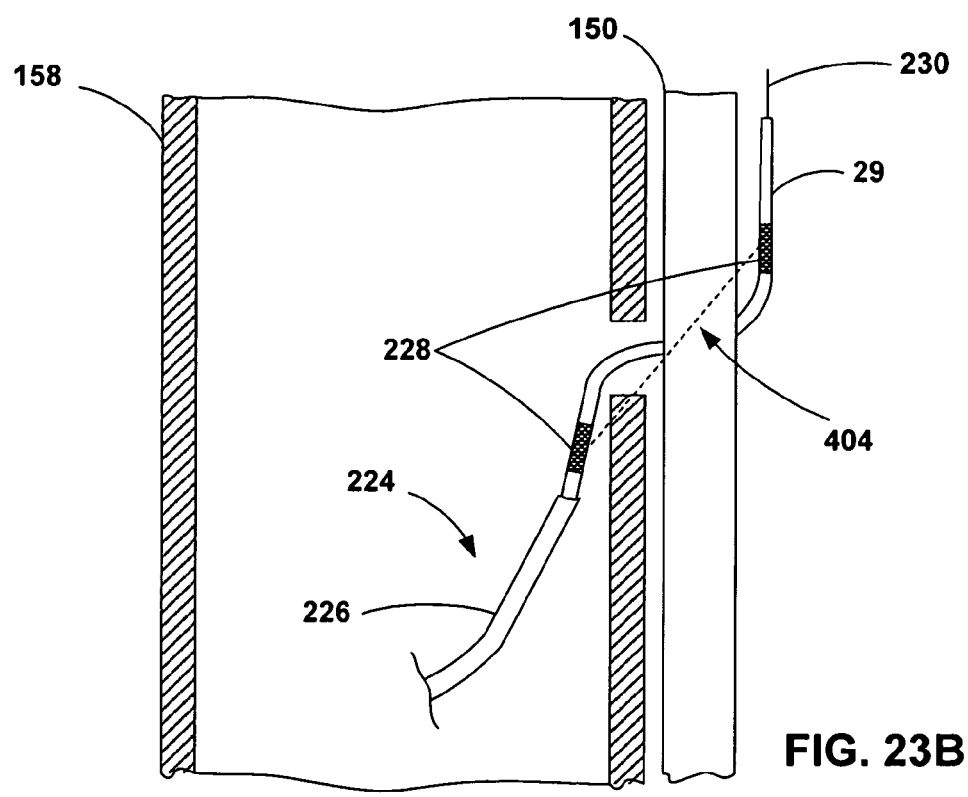

FIGS. 23A and 23B illustrate example arrangements of electrode pairs in flanking, non-contacting relationship with vagus nerve 150. The example of FIG. 23A includes multiple leads and may be applicable to different combinations of intra, extra, and transvascular lead placement techniques disclosed herein. The example of FIG. 23B includes a single lead including a pair of electrodes in flanking, non-contacting relationship with vagus nerve 150. The example of FIG. 23B may be generally applicable to extra and transvascular lead placement techniques according to this disclosure.

The example of FIG. 23A includes leads 400 and 402, and electrodes 228. In FIG. 23A, Lead 400 is arranged longitudinally along one side of vagus nerve 150. Lead 402 is arranged longitudinally along a generally opposing side of vagus nerve 150 across from lead 400. Each of leads 400 and 402 include a plurality of electrodes 228 connected to the distal end of each lead. In the example of FIG. 23A, each lead 400 and 402 includes four electrodes 228. However, in other examples, leads 400, 402 may include fewer or more electrodes and may include different numbers of electrodes. Additionally, although FIG. 23A shows two leads 400, 402, other examples may include more than two leads including, e.g., four or six leads, two of each of which are respectively arranged longitudinally on opposing sides of and including electrodes in non-contacting relationship with vagus nerve 150.

The example leads 400 and 402 shown in FIG. 23A may be placed within patient 12 according to different combinations of intra, extra, and transvascular lead placement techniques disclosed herein. For example, lead 400 may be placed intravscularly within jugular vein 158 adjacent vagus nerve 150, while lead 402 is placed extravascularly within carotid sheath 156. In another example, lead 400 may be placed intravscularly within jugular vein 158 adjacent vagus nerve 150, while lead 402 is placed transvascularly through the wall of vein 158 to an extravascular location adjacent the nerve. In still another example, both leads 400 and 402 may be placed extravascularly within carotid sheath 156 adjacent vagus nerve 150. Similarly, both leads 400 and 402 may be placed transvascularly through the wall of vein 158 to an extravascular location adjacent vagus nerve 150.

Pairs of electrodes 228 from leads 400, 402 may be employed to provide one or more anode/cathode combinations for electrical stimulation across vagus nerve 150. The neurostimulator or other device to which leads 400, 402 are connected may include a switching module as described with reference to neurostimulation module 106 of IMD 16 in FIG. 2. The switching module may selectively couple pairs of electrodes 228 to a signal generator and/or sensing module to form different anode-cathode combinations as indicated by dashed electrical field lines 404 in FIG. 23A. The switching module may include, e.g., a switch array, switch matrix, multiplexer, or any other type of switching device suitable to selectively couple stimulation energy to selected electrodes.

The example of FIG. 23B shows deployment member 224 that is configured to be advanced and retracted from, e.g., a delivery catheter (not shown in FIG. 23B) through the wall of jugular vein 158 toward vagus nerve 150. Deployment member 224 includes tubular member 226, lead 29, and a pair of electrodes 228. Tubular member 226 may be any structure including at least one lumen through which various electrode deployment structures including, e.g., lead 29 and a guide member may be advanced to place an electrodes 228 in flanking, non-contacting relationship with vagus nerve 150. Electrodes 228 are connected to lead 29, which is advanceable through tubular member along, e.g., a guide wire or stylus. In the example of FIG. 23B, lead 29 includes two electrodes 228. However, in other examples, lead 29 may include more electrodes including, e.g., four or six electrodes arranged in opposing pairs with respect to vagus nerve 150.

Deployment member 224 is advanced through jugular vein 158 toward vagus nerve 150. Lead 29, to which electrodes 228 are connected, may be advanced through a lumen of tubular member 226 to position one electrode 228 inside jugular vein 158 and one electrode 228 outside of vein 158 such that the two electrodes 228 flank vagus nerve 150 as shown in FIG. 23B. In the example of FIG. 23B, lead 29 and electrodes 228 may be guided along, e.g., a guidewire that is constructed from a shape memory material as described with reference to FIG. 22. Although the example of FIG. 23B illustrates lead 29 and electrodes 228 placed transvascularly, other examples may include lead 29 placed extravascularly adjacent vagus nerve 150 in carotid sheath 156. After lead 29 and electrodes 228 are placed with respect to vagus nerve 150, the pair of electrodes may be employed to provide electrical stimulation across vagus nerve 150. In some examples, the neurostimulator or other device to which lead 29 is connected may include a signal generator and/or sensing module to couple and energize electrodes 228 in anode-cathode combinations to stimulate vagus nerve 150 as indicated by dashed electrical field line 404 in FIG. 23B.

Examples according to this disclosure generally provide medical lead placement proximate nerve tissue within a patient for electrical stimulation of the tissue without the use of potentially deleterious electrode configurations including e.g., cuff electrodes. Techniques disclosed herein also generally provide flexible placement techniques and structures by employing one or more temporary lead placements and stimulation tests, prior to chronically placing the leads within the patient for nerve tissue stimulation. Furthermore, techniques according to this disclosure are adapted to enable minimally invasive introduction of the medical leads into the patient. Implantable electrical stimulation systems and methods in accordance with this disclosure may be used to deliver therapy to patients suffering from conditions that range from chronic pain, tremor, Parkinson's disease, and epilepsy, to urinary or fecal incontinence, sexual dysfunction, obesity, spasticity, and gastroparesis. Specific types of electrical stimulation therapies for treating such conditions include, e.g., cardiac pacing, neurostimulation, muscle stimulation, or the like.

Various examples have been described in this disclosure. These and other examples are within the scope of the following claims.

The invention claimed is:

1. A delivery system for deploying an implantable medical lead in a lumen of a blood vessel for stimulation of extravascular nerve tissue that is located adjacent to the blood vessel, via at least one electrode of the lead, the system comprising:
   an intravascular delivery catheter including a distal end, an aperture formed in a sidewall thereof to allow transverse passage out from the catheter, and a sensor located between the distal end and the aperture, the sensor adapted to radiate ultrasonic waves in order locate the extravascular nerve tissue, when the distal end of the catheter is inserted in the blood vessel lumen;
   a tubular member extendable and retractable from the catheter, via the aperture, the tubular member having a lumen configured to receive the implantable lead for advancing the lead out from the catheter and into the blood vessel lumen, when the tubular member is extended from the catheter;
   and
   a guidewire, along which the lead is advanceable, when the lead is received in the lumen of the tubular member, the guidewire being received within the lumen of the tubular member and advanceable therein, the guidewire including an anchor portion, the anchor portion being located at a distal end of the guidewire and distal to the lead, when the lead is advanced along the guidewire, the anchor portion being configured to temporarily anchor the guidewire to the wall of the blood vessel lumen, when the lead is advanced thereover and out from the catheter.

2. The system of claim 1, wherein the tubular member further includes an electrode.

3. The system of claim 1, wherein the nerve tissue comprises one of a vagus nerve, a hypoglossal nerve, a nerve plexus, nerve ganglia, and a vascular baroreceptor.

4. A method for deploying, for chronic implant, an implantable medical lead to an intravascular location, the lead including at least one electrode for delivering stimulation to extravascular nerve tissue from the intravascular location, and the method comprising:
   deploying a delivery catheter through a lumen of a blood vessel to position a sensor of the catheter at a location in proximity to the nerve tissue, the sensor being located in proximity to a distal end of the catheter, between the distal end of the catheter and an aperture formed in a sidewall of the catheter;
   activating the positioned sensor of the catheter to generate an image of an area adjacent the distal end of the catheter and outside of the blood vessel, the image showing a position of the extravascular nerve tissue relative to the blood vessel;
   identifying the nerve tissue in the image generated by the activated sensor;
   rotating the catheter, after identifying the nerve tissue in the image, to orient the aperture of the catheter toward the identified nerve tissue;

advancing the at least one electrode of the lead out from the oriented aperture of the catheter and toward the identified nerve tissue by advancing the lead over a guidewire, the guidewire being received in a lumen of a tubular member that extends out from the oriented aperture;

actively fixing the advanced electrode to a wall of the blood vessel lumen that is adjacent the identified nerve tissue;

energizing the fixed electrode to deliver stimulation; and comparing an efficacy of the delivered stimulation to a threshold efficacy.

5. The method of claim 4, wherein actively fixing the electrode to the blood vessel wall comprises screwing a helical wire into the wall.

6. The method of claim 4, wherein the nerve tissue comprises one of a vagus nerve, a hypoglossal nerve, a nerve plexus, nerve ganglia, and a vascular baroreceptor.

7. The system of claim 1, wherein the anchor portion of the guidewire is formed in a spiral that is configured to be twisted into the lumen, when the guidewire is extended from the catheter.

8. The method of claim 4, further comprising twisting a distal end of the guidewire into the wall of the blood vessel lumen to temporarily anchor the guidewire.

9. The method of claim 4, further comprising delivering test stimulation pulses via an electrode of the tubular member, prior to advancing the at least one electrode of the lead.

* * * * *